United States Patent
Cismowski et al.

(10) Patent No.: US 6,746,852 B1
(45) Date of Patent: Jun. 8, 2004

(54) AGS PROTEINS AND NUCLEIC ACID MOLECULES AND USES THEREOF

(75) Inventors: Mary Cismowski, White Plains, NY (US); Emir Duzic, Nanuet, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 09/439,410

(22) Filed: Nov. 11, 1999

Related U.S. Application Data

(63) Continuation-in-part of application No. PCT/US99/10151, filed on May 7, 1999.
(60) Provisional application No. 60/084,842, filed on May 8, 1998, and provisional application No. 60/103,355, filed on Oct. 7, 1998.

(30) Foreign Application Priority Data

May 7, 1999 (WO) ............................... PCT/US99/10151

(51) Int. Cl.$^7$ ................. C07H 21/00; C12N 15/09; C12N 15/67
(52) U.S. Cl. ................. 435/69.1; 435/252.3; 435/254.2; 435/325; 435/455; 435/320.1; 536/23.5; 536/24.1; 536/23.1
(58) Field of Search .................... 536/23.1, 24.1, 536/23.5; 514/44; 424/93.2, 93.21; 435/320.1, 70.1, 169.1, 8, 325, 455, 471, 254.2, 252.3, 410

(56) References Cited

U.S. PATENT DOCUMENTS

| | | | |
|---|---|---|---|
| 4,613,572 A | 9/1986 | MacKay et al. | 435/253 |
| 4,736,866 A | 4/1988 | Leder et al. | 800/1 |
| 4,870,009 A | 9/1989 | Evans et al. | 435/70 |
| 4,873,191 A | 10/1989 | Wagner et al. | 435/172.3 |
| 4,873,316 A | 10/1989 | Meade et al. | 530/412 |
| 4,987,071 A | 1/1991 | Cech et al. | 435/91 |
| 5,096,815 A | 3/1992 | Ladner et al. | 435/69.1 |
| 5,116,742 A | 5/1992 | Cech et al. | 435/91 |
| 5,223,409 A | 6/1993 | Ladner et al. | 435/69.1 |
| 5,270,181 A | 12/1993 | McCoy et al. | 435/69.7 |
| 5,283,317 A | 2/1994 | Saifer et al. | 528/405 |
| 5,482,835 A | 1/1996 | King et al. | 435/6 |
| 5,654,145 A * | 8/1997 | Fukuda | 435/6 |
| 6,462,177 B1 * | 10/2002 | Yen | 530/350 |

FOREIGN PATENT DOCUMENTS

| | | |
|---|---|---|
| EP | 0264166 | 4/1987 |
| WO | WO 9002909 | 3/1990 |
| WO | WO 9011354 | 10/1990 |
| WO | WO 9101140 | 2/1991 |
| WO | WO 9304169 | 3/1993 |
| WO | WO 9410300 | 5/1994 |
| WO | WO 9413802 | 6/1994 |
| WO | WO 9423025 | 10/1994 |
| WO | WO 9918211 | 4/1999 |

OTHER PUBLICATIONS

Chiu et al., Optimizing energy potentials for success in protein tertiary structure prediction, 1998, Folding & Design, vol. 3, pp. 223–228.*

Kemppainen et al., Dexamethasone rapidly induces a novel Ras superfamily member–related gene in AtT–20 cells, 1998, The Journal Of Biological Chemistry, vol. 273, pp. 3129–3131.*

Ngo et al., Computational complexity, protein structure prediction, and the levinthal paradox, 1994, The Protein Folding Problem And Tertiary Structure Prediction, pp. 492–494.*

Verma et al., Gene therapy–promises, problems and prospects, 1997, Nature, vol. 389, pp. 239–242.*

Anderson, Human gene therapy, 1998, Nature, vol. 392, pp. 25–30.*

Mountain, Gene therapy: the first decade, 2000, Tibtech, vol. 18, pp. 119–128.*

Bradley, A., (1987) "Production And Analysis of Chimaeric Mice", *Teratocarcinomas and Embryonic Stem Cells: A Practical Approach* pp. 113–151.

Camper and Tilghman, (1989) "Postnatal Repression of the ∝–fetoprotein Gene Is Enhancer Independent", *Genes and Development* 3:537–546.

Gautier et al., (1987) "∝–DNA IV: ∝–Anomeric Tetrathymidylates Covalently Linked to Intercalating Oxazolopyridocarbazole" *Nucleic Acids. Research* 15:6625–6641.

Haseloff and Gerlach, (1988) "Simple RNA Enzymes with New and Highly Specific Endoribonuclease Activities", *Nature* 334:585–591.

Alton and Vapnek, (1979) "Nucleotide Sequence Analysis of The Chloramphenicol Resistance Transposon Tn9", *Nature* 282: 864–869.

Amann et al., (1988) "Tightly Regulated Tac Promoter Vectors Useful For The Expression of Unfused and Fused Proteins In *Escherichia coli*", *Gene* 69:301–315.

Appeltauer and Achstetter, (1989) "Hormone–induced Expression of The Chs1 Gene From *Saccharomyces cerevisiae*", *European Journal of Biochemistry* 181:243–247.

Arkin and Yourvan, (1992) "An Algorithm For Protein Engineering: Simulations of Recursive Ensemble Mutagenesis", *Proceedings of The Natural Academy of Sciences* 89:7811–7815.

(List continued on next page.)

*Primary Examiner*—Scott D. Priebe
*Assistant Examiner*—Brian Whiteman
(74) *Attorney, Agent, or Firm*—John P. White; Cooper & Dunham LLP

(57) ABSTRACT

The invention provides isolated AGS nucleic acid molecules, recombinant expression vectors containing a nucleic acid molecule of the invention, including AGS specific promoters, host cells into which the expression vectors have been introduced, and a process of transcribing or expressing a heterologous sequence by culturing the host cells under appropriate conditions.

10 Claims, 14 Drawing Sheets

OTHER PUBLICATIONS

Baldari, et al., (1987) "A Novel Leader Peptide Which Allows Efficient Secretion of a Fragment of Human Interleukin 1β in Saccharomyces cerevisiae", *The Embo Journal* 6:229–234.

Banerji et al., (1983) "A Lymphocyte–Specific Cellular Enhancer Is Located Downstream of the Joining Region in Immunoglobulin Heavy Chain Genes", *Cell* 33:729–740.

Barbas et al., (1992) "Semisynthetic Combinatorial Antibody Libraries: a Chemical Solution to the Diversity Problem", *Proceedings of The National Academy Sciences* 89:4457–4461.

Bardwell et al., (1994) "Signal Propagation and Regulation in the Mating Pheromone Response Pathway of the Yeast Saccharomyces cerevisiae", *Developmental Biology* 166:363–379.

Bartel et al., (1993) "Elimination of False Positives That Arise in Using the Two–Hybrid System", *Biotechniques*, 14: 920–924.

Bartel, D. and Szostak, J.W., (1993) "Isolation of New Ribozymes from a Large Pool of Random Sequences", *Science* 261:1411–1418.

Berman and Gilman, (1998) "Mammalisn RGS Proteins: Barbarians at The Gate", *The Journal of Biological Chemistry* 273: 1269–1272.

Bourne et al., (1991) "The GTPase superfamily: Conserved Structure and Molecular Mechanism", *Nature* 349: 117–127.

Bradley, A., (1991) "Modifying the Mammalian Genome by Gene Targeting", *Current Opinion in Biotechnology* 2:823–829.

Byrne and Ruddle, (1989) "Multiplex Gene Regulation: A Two–tiered Approach to Transgene Regulation in Transgenic Mice", *Proceedings of The National Academy of Sciences* 86:5473–5477.

Calame and Eaton, (1998) "Transcriptional Controlling Elements in the Immunoglobulin and T Cell Receptor Loci", *Advances in Immunology* 43:235–275.

Chen et al., (1997) "Characterization of a Novel Mammalian Rgs Protein That Binds to Gα Proteins and Inhibits Pheromone Signaling in Yeast", *The Journal of Bilogical Chemistry* 272: 8679–8685.

Chirgwin et al., (1979) "Isolation of Biologically Active Ribonucleic Acid from Sources Enriched in Ribonuclease", *Biochemistry* 18: 5294–5299.

Cismowski et al., (1998) "A Yeast–based Approach to Functional Cloning of Novel Mammalian Proteins in the G–protein Signaling Pathway", *Archives of Pharmacology* 358: 8679–8685, Abstract only.

Clackson et al., (1991) "Making Antibody Fragments Using Phage Display Libraries", *Nature* 352:624–628.

Cull et al., (1992) "Screening for Receptor Ligands Using Large Libraries of Peptides Linked to the C Terminus of the Lac Repressor", *Proceedings of the National Academy of Sciences* 89: 1865–1869.

Cwirla et al., (1990) "Peptides on Phage: A Vast Library of Peptides for Identifying Ligands", *Proceedings of the National Academy of Sciences* 87: 6378–6382.

Daunt et al., (1997) "Subtype–Specific Intracellular Trafficking of a2–Andrenergic Receptors", *Molecular Pharmacology* 51: 711–720.

Delgrave et al., (1993) "Recursive Ensemble Mutagenesis" *Protein Engineering* 6(3):327–331.

Del Villar, K. et al., (1996) C–terminal Motifs Found in Ras–superfamily G–proteins: Caax and C–seven Motifs, *Biochemical Society Transactions* 24: 709–713.

DeWet et al., (1987) "Firefly Luciferase Gene: Structure and Expression in Mammalian Cells", *Molecular and Cellular Biology* 7: 725–737.

Druey et al., (1996) "Inhibition of G–Protein–Mediated Map Kinase Activation by a New Mammalian Gene Family", *Nature* 379: 742–746.

Edlund et al., (1985) "Cell–Specific Expression of the Rat Insulin Gene: Evidence for Role of Two Distinct 5' Flanking Elements", *Science* 230:912–916.

Foster et al., (1996) "Identification of a Novel Human Rho Protein with Unusual Properties: Gtpase Deficiency and in Vivo Farnesylation", *Molecular and Cellular Biology* 16: 2689–2699.

Gottesman, S., (1990) "Minimizing Proteolysis in *Escherichia coli*: Genetic Solutions", *Gene Expression Technology* 119–128.

Griffiths et al., (1993) "Human Anti–self Antiboides With High Specificity From Phage Display Libraries", *The EMBO Journal* 12:725–734.

Hagen et al., (1991) "Pheromone Response Elements Are Necessary and Sufficient for Basal and Pheromone–Induced Transcription of the FUS1 Gene of *Saccharomyces cerevisiae*", *Molecular and Cellular Biology* 11:2952.

Helene, C., (1991) "The Anti–gene Strategy: Control of Gene Expression by Triplex–forming–oligonucleotides", *Anticancer Drug Design* 6(6):569–84.

Helene, C. et al., (1992) "Control of Gene Expression by Triple Helix–Forming Oligonucleotides", *Annals of the New York Academy Sciences* 660:27–36.

Houghten et al., (1992) "The Use of Synthetic Peptide Combinatorial Libraries for the Identification of Bioactive Peptides", *Biotechniques* 13: 412–421.

Inoue et al., (1987) "Synthesis and Hybridization Studies on Two Complementary Nona(2'–O–methyl)Ribonucleotides", *Nucleic Acids Research* 16:6131–6148.

Inoue et al., (1987) "Sequence–dependent Hydrolysis of RHA Using Modified Oligonucleotide Splints and R Nase H", *FEBS Letters* 215:327–330.

Iwabuchi et al., (1993) "Use of the Two–hybrid System to Identify the Domain of P53 Involved in Oligomerization", *Oncogene* 8: 1693–1696.

Kang et al., (1990) "Effects of Expression of Mammalian Galpha and Hybrid Mammalian Yeast Galpha Proteins on the Yeast Pheromones Response Signal Traduction Pathway", *Molecular and Cellular Biology* 10: 2582–2590.

Kaufman et al., (1987) "Translational Efficiency of Polycistronic Mrnas and Their Utilization to Express Heterologous Genes in Mammalian Cells", *The EMBO Journal* 6:187–195.

Kemppainen et al., (1998) "Dexamethasone Rapidly Induces a Novel Ras Superfamily Member–related Gene in Att–20 Cells", *The Journal of Biological Chemistry* 273: 3129–3131.

Kessel and Gruss, (1990) "Murine Developmental Control Genes", *Science* 249:374–379.

Kurjan, (1993) "The Pheromone Response Pathway In *Saccharomyces cerevisiae*" *Annual Review of Genetics* 27:147–179.

Kurjan and Herskowitz, (1982) "Structure of a Yeast Pheromone Gene (MFα): A Putative α–Factor Precursor Contains Four Tandem Copies of Mature α–Factor", *Cell* 30:933–943.

Lam et al., (1991) "A New Type of Synthetic Peptide Library for Identifying Ligand–binding Activity", *Nature* 354: 82–84.

Lam, Kit S., (1997) "Application of Combinatorial Library Methods in Cancer Research and Drug Discovery", *Anticancer Drug Design* 12: 145–167.

Lee, E. et al., (1992) "The G226a Mutant of Gs–alpha Highlights the requirement for Dissociation of G Protein Subunits", *The Journal of Biological Chemistry* 267: 1212–1218.

Li, E. et al., (1992) "Targeted Mutation of the DNA Methyltransferase Gene Results in Embryonic Lethality", *Cell* 69:915.

Li et al., (1998) "Substitutions in the Pheromone–Responsive $G_\beta$ Beta Protein of *Saccharomyces cerevisiae* Confer a Defect in Recovery from Pheromone Treatment", *Genetics* 148: 947–961.

Logan, J. et al., (1995) "Cationic Lipids For Reporter Gene and CFTR Transfer to Rat Pulmonary Epithelium", *Gene Therapy*, 2:38–49.

Luckow and Summers, (1989) "High Level Expression of Nonfused Foreign Genes with *Autographa californica* Nuclear Polyhedrosis Virus Expression Vectors", *Virology* 170:31–39.

Madura et al., (1993) "N–recognin/Ubc2 Interactions in the N–end Rule Pathway", *The Journal of Biological Chemistry* 268:12046–12054.

Magee and Newman, (1992) "The Role of Lipid Anchors for Small G Proteins in Membrane Traficking", *Trends in Cell Biology* 2: 318–323.

Maher, L.J., (1992) "DNA Triple–Helix Formation: An Approach to Artificial Gene Repressors?", *BioEssays* 14(12):807–15.

Marks et al., (1992) "Molecular Evolution of Proteins on Filamentous Phage", *The Journal of Biological Chemistry* 267:16007–16010.

Marra et al., (1998) "The WashU–HHMI Mouse EST Project", *EMEST* 3: Gen Bank Accession No. AA790463.

Neer, E. J., (1995) "Heterotrimeric G Proteins Organizers of Transmembrane Signals", *Cell* 80 ; 249–257.

Nobes, et al., (1998) "A New Member of the Rho Family, Rnd1, Promotes Disassembly of Actin Filaments Structures and Loss of Cell Adhesion", *The Journal of Cell Biology* 141: 187–197.

Odagaki, et al., (1998) "Receptor–mediated and Receptor–independent Activation of G–proteins in Rat Brain Membranes" *Life Sciences* 62: 1537–1541.

O'Gorman et al., (1991) "Recombinant–Mediated Gene Activation and Site–Specific Integration in Mammalian Cells", *Science* 251:1351–1355.

Okamoto et al., (1995) "Ligand–dependent G Protein Coupling Function of Amloid Transmembrane Receptor" *The Journal of Biological Chemistry* 270: 4205–4208.

Pinkert et al., (1987) "An Album in Enhancer Located 10 kb Upstream Functions Along With Its Promoter to Direct Efficient, Liver–specific Expression in Transgenic Mice", *Genes and Development* 1:268–277.

Queen and Baltimore, (1983) "Immoglobulin Gene Transcription Is Activated by Downstream Sequence Elements", *Cell* 33:741–748.

Rens–Domiano and Hamm., (1995) "Structural and Functional Relationships of Heterotrimeric G–proteins", *FASEB Journal* 9: 1059–1066.

Sapperstein et al., (1994) "Nucleotide Sequence of the Yeast STE14 Gene, Which Encodes Farnesylcysteine Carboxyl Methyltransferase, and Demonstration of its Essential Role in a–Factor Export", *Molecular and Cellular Biology* 14: 1438–1449.

Sato et al., (1996) "Characterization of a G–protein Activator in the Neuroblastoma–Glioma Cell Hybrid NG108–15", *The Journal of Biological Chemistry* 271: 30052–30060.

Schultz et al., (1987) "Expression and Secretion in Yeast of a 400–kDa Envelope Glycoprotein from Epstein–Barr Virus", *Gene* 54:113–123).

Scott and Smith, (1990) "Searching for Peptide Ligands with an Epitope Library", *Science* 249: 386–390.

Seed, B., (1987) "An Lfa–3 CDNA a Phospholipid–linked Membrane Protein Homologous to its Receptor CD2", *Nature* 329:840.

Sheng et al., (1990) "The Regulation an Function of c–fos and Other Immediate Early Genes in the Nervous System", *Neuron* 4: 477–485.

Sikorski and Hieter, (1989) "A System of Shuttle Vectors and Yeast Host Strains Designed for Efficient Manipulation of DNA in *Saccharomyces cerevisiae*", *Genetics* 122:19.

Simon et al., (1991) "Diversity of G Proteins in Signal Transduction", *Science* 252: 802–808.

Simonsen et al., (1991) "Cloning by Function: Expression Cloning in Mammalian Cells", *Trends Pharmacol. Sci.* 15: 437–441.

Smith et al., (1983) "Production of Human Beta Interferon in Insect Cells Infected with a Baculovirus Expression Vector", *Mol. Cell Biol.* 3:2156–2165).

Smith, D.B. and Johnson, K.S., (1988) "Single–step Purification of Poypeptides Expressed in *Escherichia coli* as Fusions with Glutathione S–transferase" *Gene* 67:31–40.

Stevenson et al., (1992) "Constitutive Mutants of the Protein Kinase STE11 Activate the Yeast Pheromone Response Pathway in the Absence of the G Protein", *Genes and Development* 6: 1293–1304.

Stevenson et al., (1995) "Mutation of RGA1, Which Encodes Putative GTPase–activating Protein for the Polarity–establishment Protein Cdc42p, Activates the Pheromone–response Pathway in the Yeast *Saccharomyces cerevisiae*", *Genes and Development* 9: 2949–2963.

Strittmatter et al., (1993) "GAP–43 Augments G Protein-coupled Receptor Transduction in *Xenopus Laevis oocytes*", *Proceedings of the National Academy of Sciences* 90: 5327–5331.

Studier et al., (1990) "Use of T7 RNA Polymers to Direct Expression of Cloned Genes", *Gene Expression Technology* 185:60–89.

Takesono et al., (1999) "Stimulus Input to Heterotimeric G–protein Signalling Pathways", *FASEB Journal* 13: A796 Abstract only.

Thomas, K.R. and Capecchi, M. R., (1987) "Site–Directed Mutagenesis by Gene Targeting in Mouse Embryo–Derived Stem Cells", *Cell* 51:503–512.

Toh et al., (1989) "Isolation and Characterization of a Rat Liver Alkaline Phosphatase Gene", *European Journal of Biochemistry* 182: 231–238.

Valencia et al., (1991) "The ras Protein Family Evolutionary Tree and Role of Conserved Amino Acids", *Biochemistry* 30: 4637–4648.

Wada et al., (1992) "Codon Usage Tabulated from the GenBank Genetic Sequence Data", *Nucleic Acids Research* 20:2111–2118.

Whitney et al., (1998) "A Genome–wide Functional Assay of Signal Transduction in Living Mammalian Cells", *Nature Biotechnology* 16: 1329–1333.

Wilmut, I. et al., (1997) "Viable Offspring from Fetal Adult Mammalian Cells", *Nature* 385:810–813.

Winoto and Baltimore, (1989) "A Novel, Inductible and T Cell–specific Enhancer Located at the 3' End of the T Cell Receptor $\alpha$ Locus" *The EMBO Journal* 8:729–733.

Zervos et al., (1993) "Msi1, a Protein That Specifically Interacts with Max to Bind Myc–Max Recognition Sites", *Cell* 72: 223–232.

* cited by examiner

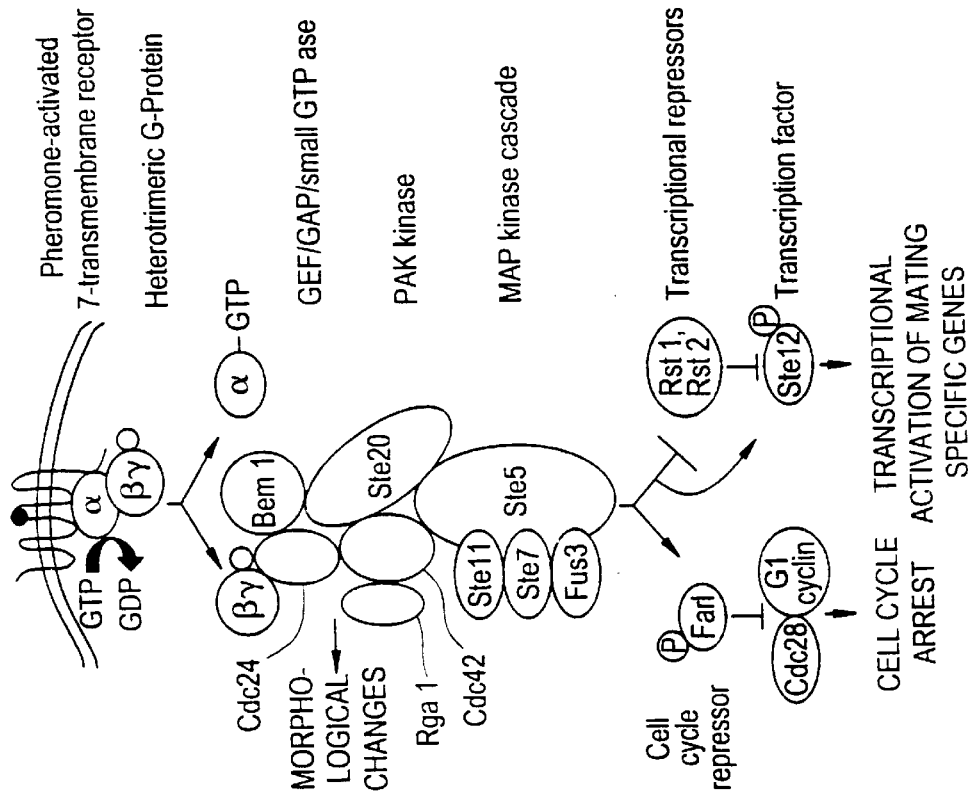
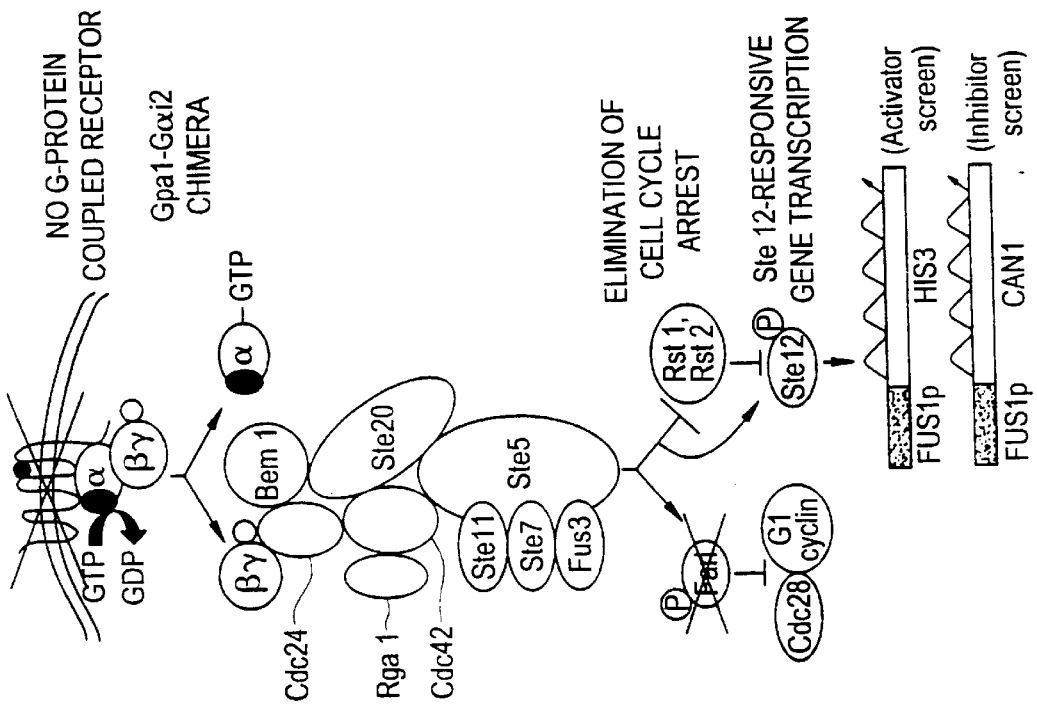

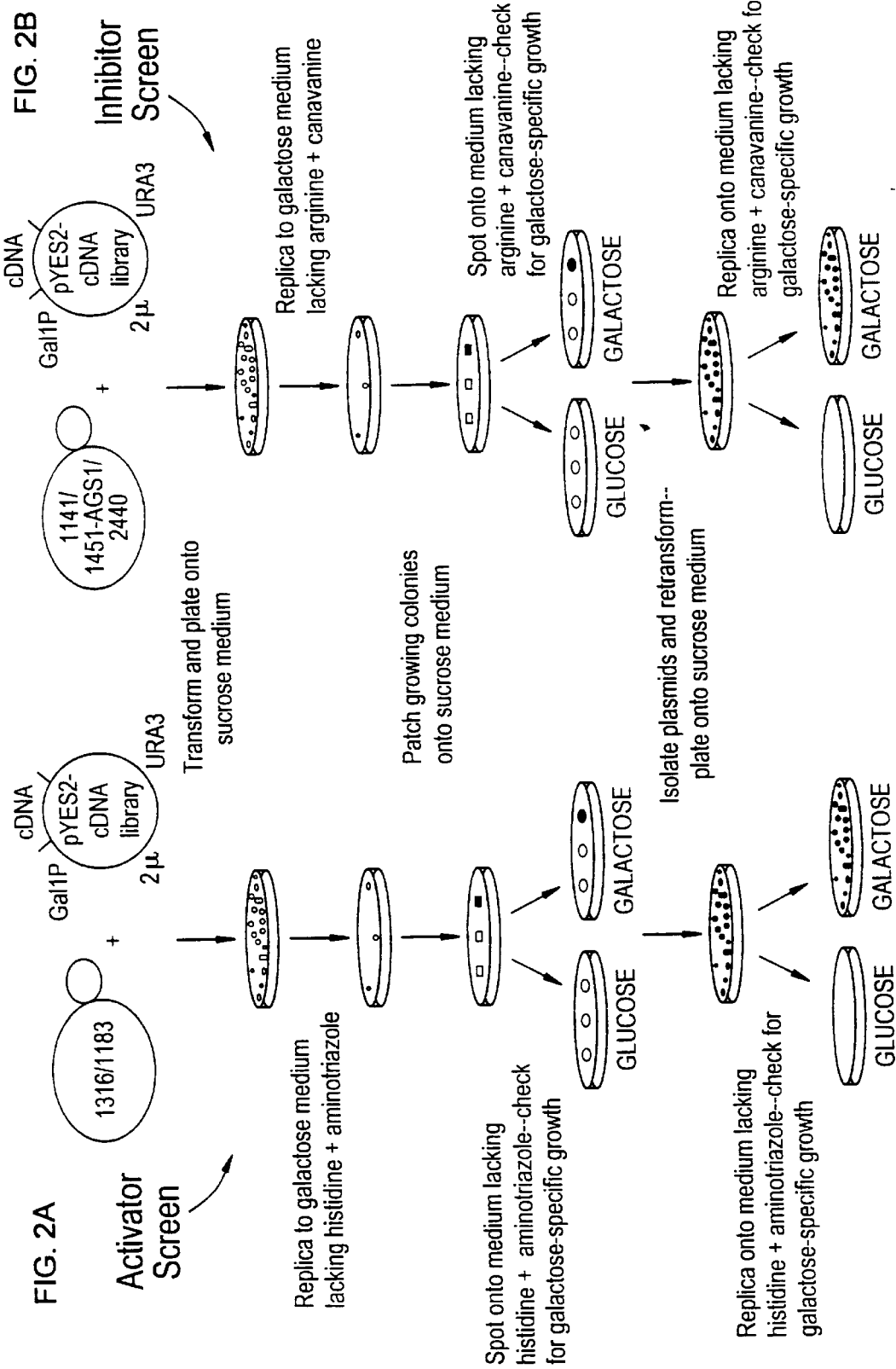

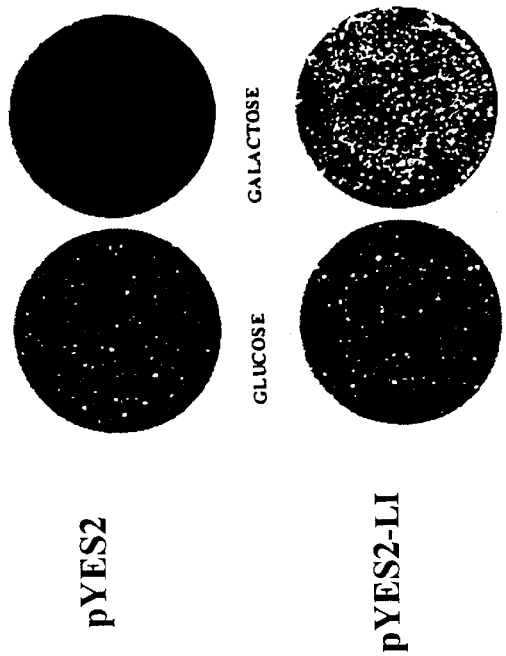
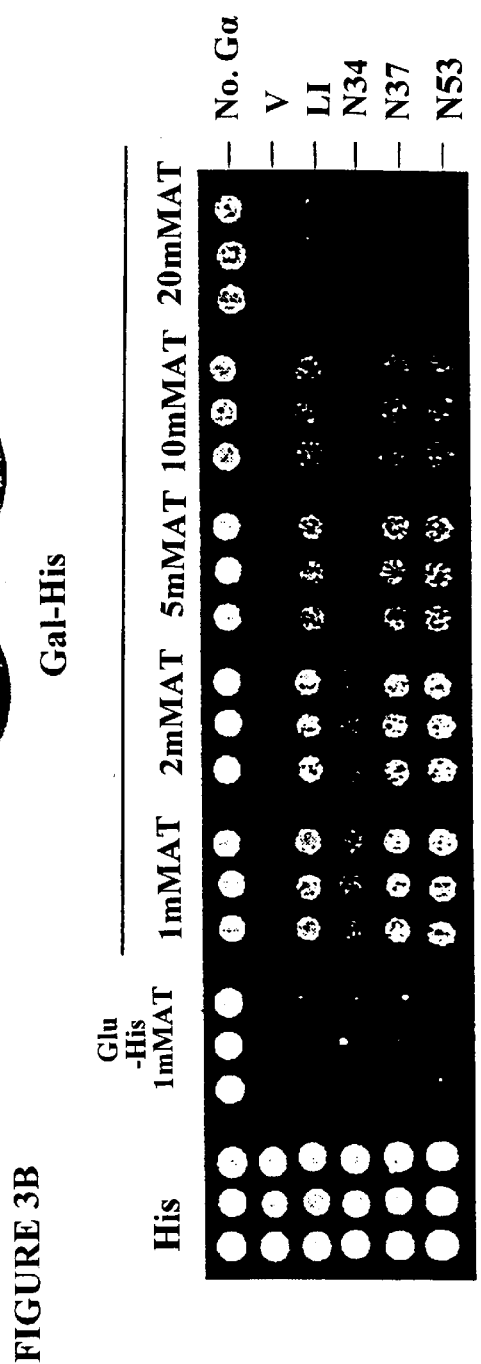
FIGURE 3A
FIGURE 3B

FIG. 3C-1

```
         10         20         30         40         50         60
ATGAAACTGG CCGCGATGAT CAAGAAGATG TGCCCGAGCG ACTCGGAGCT GAGTATCCCG   60
GCCAAGAACT GCTATCGCAT GGTCATCCTC GGCTCGTCCA AGGTGGGCAA GACGGCCATC  120
GTGTCGCGCT TCCTCACCGG CCGCTTCGAG GACGCCTACA CGCCTACCAT CGAGGACTTC  180
CACCGCAAGT TCTACTCCAT CCGGGGCGAG GTCTACCAGC TCGACATCCT CGACACGTCC  240
GGCAACCACC CGTTCCCCGC CATGCGGCGC CTCTCCATCC TCACAGGAGA CGTTTTCATC  300

310        320        330        340        350        360
CTGGTGTTCA GTCTGGACAA CCGCGACTCC TTCGAGGAGG TGCAGCGGCT CAGGCAGCAG  360
ATCCTCGACA CCAAGTCTTG CCTCAAGAAC AAAACCAAGG AGAACGTTGA CGTGCCCCTG  420
GTCATCTGCG GCAACAAGGG TGACCGCGAC TTCTACCGCG AGGTGGACCA GCGCGAGATC  480
GAGCAGCTGG TGGGCGACGA CCCCCAGCGC TGCGCCTACT TCGAGATCTC GGCCAAGAAG  540
AACAGCAGCC TGGACCAGAT GTTCCGGCGG CTCTTCGCCA TGGCCAAGCT GCCCAGCGAG  600

610        620        630        640        650        660
ATGAGCCCAG ACCTGCACCG CAAGGTCTCG GTGCAGTACT GCGACGTGCT GCACAAGAAG  660
GCGCTGCGGA ACAAGAAGCT GCTGCGGGCC GGCAGCGGGC GCGGCGGCGG CGACCCGGGC  720
GACGCCTTTG GCATCGTGGC ACCCTTCGCG CGCCGGCCCA GCGTACACAG CGACCTCATG  780
TACATCCCGC AGAAGGCCAG CGCCGGGAGC CAGGCCAAGG ACAAGGAGCG CTGGTCATC   840
AGCTAG  846
```

FIG. 3C-2

```
MKLAAMIKKMCPSDSELSIP AKNCYRMVILGSSKVGKTAI      40
                              *
VSRFLTGRFEDAYTPTIEDF HRKFYSIRGEVYQLDILDTS      80
                                       *
GNHPFPAMRRLSILTGDVFI LVFSLDNRDSFEEVQRLRQQ     120
  *
ILDTKSCLKNKTKENVDVPL VICGNKGDRDFYREVDQREI     160

EQLVGDDPQRCAYFEISAKK NSSLDQMFRALFAMAKLPSE     200

MSPDLHRKVSVQYCDVLHKK ALRNKKLLRAGSGGGGGDPG     240

DAFGIVAPFARRESVHSDLM YIREKASAGSQAKDKERCVI S   281
```

FIG. 5C

TAAGAAGTTGTACTTAAAGCGGAGGAGCTAAGCCACCTGCCAAAATGTGCAAAGACTTGCAGCTTTGCCCCACTCATGCTGGAAAGGGCCCAAGGAGAT
                                  M   C   K   G   L   A   A   L   P   H   S   C   L   E   R   A   K   E   I
TAAGATCAAGTTGGGAATTCTCTCCAGAAGCCAGATCAGTTGGTGACCTTGTCATTCCGTACAATGAGAAGCCAGAGAAACCAGCCAAGACCCAGAAA
  K   G   L   A   A   L   P   H   S   C   L   E   R   A   K   E   I
ACCTCGCTGACGAGGCCCTGCAGTGGCGTGATTCCTGACAACAACTGCAGAACAACTATGACTTGCCAGTTTCAAAGTTTCCTGAAGTCTGAAT
  K   I   K   L   G   I   L   L   Q   K   P   D   S   V   G   D   L   V   I   P   Y   N   E   K   P   K   P   A   K   T   Q   K
TCAGTGAGGAAAACCTTGAGTTCTGGATTGCCTGTGAGGATTACAAGAAGATCAAGTCCCCTGCCAAGATGGCTGAGAAGGCAAAGCAAATTTATGAAGA
  T   S   L   D   E   A   L   Q   W   R   D   S   L   D   K   L   L   Q   N   N   Y   G   L   A   S   F   K   S   F   L   K   S   E
ATTCATTCAAACGGAGCCTCCTAAAGAGGTCAATATTGACCACTTCACTAAGGACATCACTATGAAGAACCTGGTGGAACCTTCCCTGAGCAGCTTTGAC
  F   E   E   N   L   E   F   W   I   A   C   E   D   Y   K   K   I   K   S   P   A   K   M   A   E   K   A   K   Q   I   Y   E
ATGGCCCAGAAAAGAATCATGCCCTGAGTTCTCTGCCTCGCTTTGTGCGCTCTGAGTTTTATCAGGAGTTAATCAAGTAGTAATTTAGCC
  F   I   Q   T   E   A   P   K   E   V   N   I   D   H   F   T   K   D   I   T   M   K   N   L   V   E   P   S   L   S   S   F   D
AGGCTATGAAATCATCCTGTGAGTTATTCCTCCATAATAACCCTGCATTTCCCACAGCAGCTTTGCTCAGTGATACCCA
  M   A   Q   K   R   I   H   A   L   M   E   K   D   S   L   P   R   F   V   R   S   E   F   Y   Q   E   L   I   K
CATGGGAAAAATCCCAGGGGATGTTGCTTACTCTTTTGCCCACACTGCTTTGGATACTATCTACTGTCCGAAGGCCTTCTTTCCCCACTCAATTCTTC
CTGCCCCTGTTATTAATTAAGATATCTTCAGCTTGTCAGTCAGACCCAATCAGAATCACAGAAAATCCTGCTAAGGCAAGAAATATAAGACAAGACTAT
GATATCAATGAATGTGGGTTAAGTAATAATAGATTTCCAGCTAAATTGGTCTAAAAAGAATATTAAGTGTGACAGACCTATTCAAAGGAGCTTAATTGAT
CTCACTTGTTTTAGTTCTGATCCAGGAGATCACCCCTCTAATTATTTCTGAACTTGGTTAATAAAGTTTATAAGATTTTTATGAAGCAGCCACTGTAT
GATATTTTAAGCAAATGTTATTTAAAATATTGATCCTTCCCTTGACCACCTTCATGTTAGTTGGGTATTATAATAAGAGATACAACCATGAATATA
TTATGTTTATACAAATCAATCTGAACACAATTCATAAGATTCTCTTTTATACCTTCCACTGGCCCCCTCCACCTGCCCATAGTCACCAAATTCTG
TTTAAATCAATGACCTAAGATCAACAACATGAAGTATTTATAAATGTATTTATGCTAGACTGTGGGTCAAATGTTCCATTTCAAATTATTTAGAA
TTCTTATGAGTTTAAAATTTGTAAATTTCTAAATCAATCATGTAAAATGAAACTGTTCTCTCCACCTAAATATCAAGATGGCTA
TATGCTAAAAGAGAAAATATGGTCAAGTCTAAAATGGCTATTGTCCTATGATGCTATTATCATAGACTAATGACATTTATCTTCAAAACACCAAATTG
TCTTTAGAAAAATTAATGTGATTACAGAGTGAGAGGCCTTCAGTGAGACACTTTTAAGGTACACTGCATTTGCAAAAAAAAAAAAAAAA

FIGURE 7A

```
                    PM1                                          G1                    PM2
C-HA-RAS1   ----------MTEYKLVVVGAGGVGKSALTIQLIQNHFVDEYDPTIEDS
RALA        ------MAANKPRGQNSLALHKVIMVGSGGVGKSALTLQFMYDEFVEDYEPTKADS
RAB-1A      ---------MSSMNPEYDYLFKLLLIGDSGVGKCLLLRFADDTYTESYISTIGVD
RHOHP1      -----MTAAQAAGEEAPPGVRSVKVVLVGDGGCGKTSLLMVFADGAFPESYTPTVFER
CDC42       -----------------MQTIKCVVVGDGAVGKTCLLISYTTNKFPSEYVPTVFDN
RAC2        -----------------MQAIKCVVVGDGAVGKTCLLISYTTNAFPGEYIPTVFDN
ARL1        ------MGGFFSSIFSSLFGTREMRILILGLDGAGKTTILYRLQVGEVVTTI-PTIGFN
RND3/RHOE   ----------MDPNQNVKCKIVVVGDSQCGKTALLHVFAKDCFPENYVPTVFEN
AGS1        MKLAAMIKKMCPSDSELSIPAKNCYRMVILGSSKVGKTAIVSRFLTGRFEDAYTPTIEDF

PM3
C-HA-RAS1   YRKQ-VVIDGETCLLDILDTAGQEEYSAMRDQYMRTGEGFLCVFAINNTKSFEDIHQYRE
RALA        YRKK-VVLDGEEVQIDILDTAGQEDYAAIRDNYFRSGEGFLCVFSITEMESFAATADFRE
RAB-1A      FKIRTIELDGKTIKLQIWDTAGQERFRTITSSYYRGAHGIIVVYDVTDQESFNNVKQ-WL
RHOHP1      YMVN-LQVKGKPVHLHIWDTAGQDDYDRLRPLFYPDASVLLCFDVTSPNSFDNIFNRWY
CDC42       YAVT-VMIGGEPYTLGLFDTAGQEDYDRLRPLSYPQTDVFLVCFSVVSPSSFENVKEKWV
RAC2        YSAN-VMVDSKPVNLGLWDTAGQEDYDRLRPLSYPQTDVFLICFSLVSPASYENVRAKWF
ARL1        VET------VTYKNLKFQVWDLGGQTSIRPYWRCYYSNTDAVIYVVDSCDRDRIGISKSELV
RND3/RHOE   YTAS-FEIDTQRIELSLWDTSGSPYYDNVRPLSYPDSDAVLICFDISRPETLDSVLKKWK
AGS1        HRKF-YSIRGEVYQLDILDTSGNHPFPAMRRLSILTGDVFILVFSLDNRDSFEEVQRLRQ
```

FIGURE 7B

```
                      G2
C-HA-RAS1   QIKRVKD--------SDDVPMVLVGNKCDLAA-------------RTVESRQAQDLARS
RALA        QILRVKE--------DENVPFLLVGNKSDLEDK-------------RQVSVEEAKNRAEQ
RAB-1A      QEIDRYA--------SENVNKLLVGNKCDLTTK-------------KVVDYTTAKEFADS
RHOHP1      PEVNHF---------CKKVPIIVVGCKTDLRKDKSLVNKLRRNGLEPVTYHRGQEMARSV
CDC42       PEITHH---------CPKTPFLLVGTQIDLRDDPSTIEKLAKNKQKPITPETAEKLARDL
RAC2        PEVRHH---------CPSTPIILVGTKLDLRDDKDTIEKLKEKKLAPITYPQGLALAKEI
ARL1        AMLEEE---------LRKAILVVFANKQDMEQAMTSSEMANSLGLPALKDRK--------
RND3/RHOE   GEIQEF---------CPNTKMLLVGCKSDLRTDVSTLVELSNHRQTPVSYDQGANMAKQI
AGS1        QILDTKSCLKNKTKENVDVPLVICGNKGD-RDFY------------REVDQREIEQLVGD

G3
C-HA-RAS1   YG---IPYIETSAKTRQG-VEDAFYTLVREIR----------------------------
RALA        WN---VNIVETSAKTRAN-VDKVFFDLMREIR----------------------------
RAB-1A      LG---IPFLETSAKNATN-VEQSFMTMAAEIK----------------------------
RHOHP1      GA---VAYLECSARLHDN-VHAVFQEAAEVAL----------------------------
CDC42       KA---VKYVECSALTQRG-LKNVFDEAILAAL----------------------------
RAC2        DS---VRYLECSALTQRG-LKTVFDEAIRAVL----------------------------
ARL1        -----WQIFKTSATKGTG-LDEAMEWLVETLKSRQ-------------------------
RND3/RHOE   GA---ATYIECSALQSENSVRDIF----HVATLAC-------------------VNKTNKVKRNK
AGS1        DPQRCAYFEISAKKNSS--LDQMFRALFAMAKLPSEMSPDLHRKVSVQYCDVLHKKALRNKK

C-HA-RAS1   ----------------QHKLRKLNPPDESGPGCMSCKCVLS
RALA        ----------------ARRMEDSKEKNGKKKRKSLAKRIRERCCIL
RAB-1A      -KRMGPGATAGGA---
RHOHP1      ----------------EKSNVKIQSTPVKQAGGCC
CDC42       ----------------SSRGRNFWRRITQGFCVVT
RAC2        ----------------EPPETQPKRKCCIF
ARL1        ----------------CPQPTRQQKRACSLL
RND3/RHOE   SQRA-----------TKRISHMPSRP---------ELSAVATDLRKDKAKSCTVM
AGS1        LLRAGSGGGGGDPGDAFGIVAPFARRPSVHSDLMYIREKASAGSQAKDKERCVIS
```

FIG. 8

|          | P REGION         | G' REGION         |
|----------|------------------|-------------------|
| RhoE/Rnd3 | KIVVVGDSQCGKTALL | LSLWDTSGSPYYD     |
| Rnd2     | KIVVVGDAECGKTALL | LNMWDTSGSSYYD     |
| Rnd1     | KLVLVGDVQCGKTAML | LSLWDTSGSPYYD     |
| RhoA     | KLVIVGDGACGKTCLL | LALWDTAGQEDYD     |
| RhoB     | KLVVVGDGACGKTCLL | LALWDTAGQEDYD     |
| Cdc42    | KCVVVGDGAVGKTCLL | LGLFDTAGQEDYD     |
| Rac1     | KCVVVGDGAVGKTCLL | LGLWDTAGQEDYD     |
| H-ras    | KLVVVGAGGVGKSALT | LDILDTAGQEEYD     |
| AGS      | 26 RMVILGSSKVGKTAIV | LDILDTSGNHPFP 86 |
|          | *                | * *               |

FIGURE 9A

```
GGATCCACGG GGCGGATGGT TCTGTGAGTT GCGAGTTGTT CCTGTTTGTC TTCCAGCCCC    60
CAGTCCTCCC CGGCCACTCT GATTAGCCAG CCTAGGGTAG GGCCTGGCAT AAAGTCACAC   120
AGGCAAACCC CAGAAGAAGG AAAAAGGGCA CCTGCATGAA CAAAGAGCTG GGTGGCAGAG   180
GCTGCACCGG GGTAAGACTT CCTTCATGCA GTTGGGAGTC CGCCCATGTG GGGACATCAG   240
GAGATGCCAC CCCACAGAAT TGGTGGCTAG GCTGTCCTGG GTGTGGCCGA GAGAGGCCTG   300
ATCCCAGTGC TTCTTTCATT CTGGTCCTTT CTGAAATGGC TTGGATTTTT AAAAAACCAT   360
GAGCATTTAT TACTTTTGTA ATAAAAGGAA AGAGATGCCC TTTTAAAAGA AAAGACGAGG   420
GCGGAAACAA GGAAGTTGGC TTGCTGCTTG AGGAGTAAAG TCCCAGAGGC CACCTCCTTG   480
ACAGGAGGCG CTCTGGGGCA TTCAGAATGG GAATGGCAGG TGGGCCTGGG TCTTCACAAC   540
CCAGCATCCG TAGGGCAGAC GGCCATGCAC AGATGGTACC AGGAATCACT GTGGCTGAGG   600
ACACAGGCTA GATCAGTGCC TGCCAGTGTC ATGTTCCTGA TTTAAGGGGC CAGCCTGGAC   660
ACTGACCAGG GGAGAGCTGG GCTGTGATCC TTGACCCTCG GCCCTCCAC TCATATCAAA    720
TGGACCCTCT TGGGACTAGA GCCCCAGGAG GCAATGGCTG TGTGGGGTCC ACCTTCACTA   780
TAGCCCTGGC CATCAGTCAT CCCAAGTTAG AGCCCGGCTG CCCATGCAGT GCCGCTGTGG   840
GAGGCACAGG AAGGCGGTGC TCAGTCTGAA GGTGGTTCAG GTCCGTACCT TAACTGAGCC   900
CCCCCATGTA CCCTCAACTG GCTCCTTTAT GCAGTGAACA CCCTGCACCA CTGCAGCCCT   960
ATATCCAGGG CTGCGACTCA GTTCCTTCTC CCCTTCTCCC AGACTCTGGC AGACATACCT  1020
CAGATGGGGG CAGGAACCAA GAATGGCGGG GCTCCAGCCC CAGCTAGCCT GTCGGATAAC  1080
TGCTGCATAA GTGACACCAG GAATCAGAGC CAGGCCAGGG CCACTGATGA GCCCTTGGAT  1140
GCTCACTGTG TGATGCGTGC ATTTGAAATA TCTGACAGTA AGAGTGAGGC CTGGGAGAGA  1200
TGCAGGGACT CTGAGGATGG GGGCCAAGCT GGGCTGAGAA ACAAGTTAGT GGTGTCCTGC  1260
AGCAGCCCCT ACAGCAAGTG CCAGCGTGGG AGGGAGGTGG GTAGGCATGG GGTGGGTGGT  1320
ATGGCACTCA CAGCACTGCC TGCAGACCAC CACCACCTGA CAGCTGGGCC GGTGGTGCCA  1380
GCTAATGGCT CCCTAGTTTT CTCGTAAGTC AGACGTGGCC AAAGCAAAAC ACTGAGCACA  1440
CAGGTTGCCT TGAGGAGCAG TGACTGCCTC AAGAGCTCAG GGCTGAGGAG CTGGCTCCAG  1500
ACAGCCTGTT GCCAATGTTC AGCAACATCA CCCCACTCCT GGTTACTGAT CGACCTGGTG  1560
TGCTCTTGAG AGTACCCCCA CCAGGCCTCA TGGGTCAATA CTACTGTTAT TGTTGCTATT  1620
GTTATTACCA GGCCCCGCCC TCCTAAAGCA TTTGCATATT TTCATCCTTA ATCACAGAAC  1680
CAGAATCAGT ATCTTCCAGA AGAGAAAACT GAGGCCCAGG AGAAAGCAAG AGGCTGTGCT  1740
GTGCTCCCAG GGCCTTCCTG GGCTCGCTGT GGCTTTGAGC TCCAGGTCTC TCAGCTAGAC  1800
AATGAGAACG TCGGCCCACG CGCGGCACAG TAAAAGCCCA AAATGCTATG ATGGACGGGG  1860
TGGGCCGCTG GCTGCAGAGC CCTCCATACC ACAGAGCATC TCTGGCTGGG AGAAAGGAGC  1920
AGGCTGAGGC CTGCAGCAGA GCGCGGGGTT GGGGACCGCT CCTGTTGGGC CCCAGCAAGG  1980
CGCCCTGAGA CCCCTGCTCC ATCCCTGCCG CTCCCCACCC GCCTGCTCCT AGCCTCTGTT  2040
CTAGCTCTGC CCGCGGCGGC CACAGCCTCC CCGAGCCGCC GGCCGGGCCC TCTGCTGCCC  2100
TCTGGCGGCC CGAGCGCGCG GTGCCGAGCT CCGCGCCTGA GGCCTGAAA CCCCGCGTCC   2160
GCCCGGCGGT CGCCTCCCGG GAACAAGAGC CCGGCTGGGG ACCGGAGCGG AAGGGGGCTG  2220
GGGCTGGGGC TGTGCTCTGA GGACTGCAAT ATACGGTCCG CGCAAGCACT CAGCAAACGC  2280
TGCTGCGCTT ACTGGGTTAC TTACTAGATT CCTATTCTCT GGGGAAACTG AGAACCAAAG  2340
AAAATAAGAG TACGCGCGCG GGAGGTGCAG GAATGGGGGT CCTTGCCCGA AGTCGCAGAG  2400
GGACAGGGGC ACCGCCGGGA CCAGAACCCC GACGCCCTG CGGCCGCCGA GCCCGCGGCA   2460
GTGGAAAAGC GGAGTCCGAG CGCCTCCAGC CTCAGCCCGA CCCTGGACTG CTCCCCCCAG  2520
CCCCCGCGCC CAGAGAGCAG GAGCCCGGCA GCGGGTGACG AGGTCGCCGG GACTGGGAGC  2580
CGGTGCGGGG GAGGCGGGCC CCGCGGGGCG TGACGCACCG AGCTGGGAGG GCCGGGGCGG  2640
GGCAGCCGAG CAGGCTGCAT ATAAGGGCGG CGGCCGGGCG CCAAAGCCAG AGCAAGCGGC  2700
CTGTGCCCAG ATCCTGGAG AACCCCAGCC GAGCCCAGCC TAGCCCGAGC CCAGCCCGAG   2760
CGGAGCCGGA GCCCCAAGCC CGAGCCGCGC CCAGCCCGAG CAGAGCCCTC CAGCCGCTCA  2820
CCCCGCGTGC CACCCCAGCG ACCCTCAGCC GCTCTCTGCC CTTCTCTCGG CCCCGCGCCC  2880
GCCCTCGCGG CCCCTCTGCC CAATGAAACT GGCCGCGATG ATCAAGAAGA TGTGCCCGAG  2940
CGACTCGGAG CTGAGTATCC CGGCCAAGAA CTGCTATCGC ATGGTCATCC TCGGCTCGTC  3000
CAAGGTGGGC AAGACGGCCA TCGTGTCGCG CTTCCTCACC GGCCGCTTCG AGGACGCCTA  3060
CACGCCTACC ATCGAGGACT TCCACCGCAA GTTCTACTCC ATCCGCGGCG AGGTCTACCA  3120
GCTCGACATC CTCGACACGT CCGGCAACCA CCCGTTCCCC GCCATGCGGC GCCTCTCCAT  3180
CCTCACAGGT GAGCCGGGGG CCGGGCAGGT GCGGGAGGGA AGGGCGGGGA ACCCTCGGCC  3240
```

FIGURE 9B

```
AGGGCGCCCC GCGAGCGCCG GTCCGGCTGC CGCGCGCCGA GTAGTGGCT TCGGCGTTAG 3300
AGAGGCTAGC GCGCCCCGCG CGGCCTCAAA GTCAGCCCGA CTTGTCCCCT GGGCGGCCAC 3360
CCTCACCTTC TCCTTTTCTG CTCTCTGTGC CCCCTCTAGG AGACGTTTTC ATCCTGGTGT 3420
TCAGTCTGGA CAACCGCGAC TCCTTCGAGG AGGTGCAGCG GCTCAGGCAG CAGATCCTCG 3480
ACACCAAGTC TTGCCTCAAG AACAAACCA AGGAGAACGT GGACGTGCCC CTGGTCATCT 3540
GCGGCAACAA GGGTGACCGC GACTTCTACC GCGAGGTGGA CCAGCGCGAG ATCGAGCAGC 3600
TGGTGGGCGA CGACCCCCAG CGCTGCGCCT ACTTCGAGAT CTCGGCCAAG AAGAACAGCA 3660
GCTGGACCA GATGTTCCGC GCGCTCTTCG CCATGCCCAA GCTGCCCAGC GAGATGAGCC 3720
CAGACCTGCA CCGCAAGTTC TCGGTGCAGT ACTGCGACGT GCTGCACAAG AAGGCGTGC 3780
GGAACAAGAA GCTGCTGCGG CCCGGCAGCG GCGGCGGCGG CGGCGACCCG GGCGACGCCT 3840
TTGGCATCGT GGCACCCTTC GCGCACCCGGC CCAGCCGTACA CAGCGACTTC ATGTACATCC 3900
GCGAGAAGGC CAGCGCCGGC AGCCAGGCCA AGGACAAGGA GCGCTGCGTC ATCAGCTAGG 3960
AGCCCCGCCG CGCTGGCGAC ACAACCTAAG GAGGACCTTT TTGTTAAGTC AAATCCAACG 4020
GCCGGTGCG CCCCAGGCCG GGAGCGCGCG TGGACTGGCG TCTCCCCTCC CGGCGATCCG 4080
CCCCCAGCAC TGGGGAGGCG CCACTGAACC GGTCATCTGC TCCGAAGGA 4140
AAGAGAACGG GCCAAGACTG GGACTATTCC TCCCCCCGG AGGCCCGCCA 4200
CCCCCATAAC TTTGGAGCG AGGGCCCAGC CGAGGTGGA TTTATCTTCT CAAAGACTTA 4260
AGAGTGAGCG CGGGGTGGGG GAGGGATGTG AAGTTATCCA GCCTCTGCTA GGCTTCAAGA 4320
AACCGTCATG CCCGCTTGAG GGTCAGGACC CACGGGCAT TATCTTGTCT GTGATTCCGG 4380
GTGCTGTGA CAGCCGGTAG AGCCTCTGCC CTCCCGAAAC TAAGCGGGGG GGCGTGGGTC 4440
AAATCATAGC CAAGTGACTT GTTTACATGT GAGTGAAACT GCACAAAGGA ACACAAAACA 4500
AAACTTGCAC TTTAACGGTA GTTCCGGTGT CAACATGACT CTTTATTTGG CCTTACCCAG 4560
GTGTTTATAC TGTGTGTGTG TGAGGTCTTT AAAGTTATTG GTTTTTTTTT TTTTTTAATA 4620
TACAATAAAA TAATTTAAAA TGGAAAACCG GTTTTTTTTT TTTTTTTTTTTT TTTTTTTGC 4680
TTTTAGAGAT GGCTGGAGTG GGGAAGGGTG GGGAGAAGGA AAGGGCTGGG CTTTGACTTA 4740
GGTGGAACTA GAACTTACCT TCCCCAGAAC TGGAAAATAA CCCTGGCCTT CTGAAGGCAG 4800
CTTCAGCTGC CAGAAAAGCC CCAGATGCCT GGGCATCTA TGTAGGGGAT GGTTCCCTAG 4860
AAAACCGGGA AGAATATAAA GGATTTCAGG GTCTCCCCTG GAGATGAACT CTTTCTAGCC 4920
ATCCACCCGC TTAATTTTCT TGGGTTAGA TGACAAAAGG CCTCATTTTC TGAGAGAATG 4980
TTCTGAATTC                                                       4990
```

AGS PROTEINS AND NUCLEIC ACID MOLECULES AND USES THEREOF

This application is a continuation-in-part of PCT International Application No. PCT/US99/10151 filed May 7, 1999 and claims the benefit of U.S. Provisional Application No. 60/084,842, filed May 8, 1998 and U.S. Provisional Application No. 60/103,355, filed, Oct. 7, 1998.

Throughout this application, various publications are referenced by author and date. Full citations for these publications may be found throughout the specification. The disclosures of these publications in their entireties are hereby incorporated by reference into this application in order to more fully describe the state of the art as known to those skilled therein as of the date of the invention described and claimed herein.

BACKGROUND OF THE INVENTION

Heterotrimeric G protein-mediated signal transduction is a tightly regulated event. All known G protein-coupled receptor (GPCR) mediated signaling pathways rely on multiple regulatory mechanisms in order to prevent inappropriate induction of the signal and to facilitate recovery during chronic stimulation (Gilman (1987) *Ann. Rev. Biochem.* 56:615–649, reviewed in Simon et al. (1991) *Science* 252:802–808; Conklin and Bourne (1993) *Cell* 73:631–641; Neer (1995) *Cell* 80:249–257; Rens-Domiano and Hamm (1995) *FASEB J.* 9:1059–1066). These regulatory mechanisms function at every level of the signaling cascade. Regulation of GPCR activation is believed to involve phosphorylation of the receptor C-terminus and subsequent receptor internalization (Palczewski and Benkovic (1991) *Trends Biol. Sci.* 16:387–391; Goodman et al. (1996) *Nature* 383:447–450; Chen and Konopka (1996) *Mol. Cell. Biol.* 16:247–257), though this does not appear to be a universal mechanism (Daunt et al. (1997) *Mol. Pharm.* 51:711–720). Known mechanisms of regulation of signal transduction at the level of the heterotrimeric G protein include receptor-mediated facilitation of GTP/GDP exchange on $G\alpha$ (reviewed in Simon et al. (1991) *Science* 252:802–808; Conklin and Bourne (1993) *Cell* 73:631–641; Neer (1995) *Cell* 80:249–257; Rens-Domiano and Hamm (1995) *FASEB J.* 9:1059–1066) and enhancement of the intrinsic GTPase activity of $G\alpha$ proteins by RGS-like proteins (reviewed in Berman and Gilman (1998) *J. Biol. Chem.* 273:1269–1272). Activation of PAKs, serine/threonine kinases that transduce signals from heterotrimeric G proteins to the MAP kinase cascade, has been shown to occur through interaction with either the small G proteins Cdc42 and Rac, or through interaction with heterotrimeric G proteins (reviewed in Sells and Chernoff (1997) *Trends Cell Biol.* 7:162–167). GPCR-coupled MAP kinase cascades and their downstream transcription factors, in turn, are regulated through phosphorylation/dephosphorylation cycles that may or may not require small G proteins (reviewed in Cobb and Goldsmith (1995) *J. Biol. Chem.* 270:14843–14846). (Strittmatter et al. (1993) *Proc. Nat'l Acad. Sci., USA* 90:5327–5331; Okamoto et al. (1995) *J. Biol. Chem.* 27:4205–4208; Sato et al. (1996) *J. Biol. Chem.* 271:30052–30060) and non-protein activtors (summarized in Odagaki et al. (1998) *Life Sciences* 62:1537–1541.

Even with the identification of these diverse regulatory systems, an in-depth understanding of the temporal and spatial regulation of GPCR mediated signaling remains elusive. In fact, cellular variations in the efficiency and/or specificity of coupling observed for many specific receptor-heterotrimeric G protein complexes suggest the presence of additional unidentified, cell-specific regulators of the signaling process.

SUMMARY OF THE INVENTION

In an attempt to identify novel factors involved in regulating signaling through GPCR-mediated signal transduction pathways, a screening system was devised in the yeast *Saccharomyces cerevisiae* designed to identify receptor-independent activators of the pheromone response pathway. These functional screens can be designed to target not only specific regulatory pathways in yeast, but also an introduced mammalian component or components. Yeast strains containing an intact signal transduction cascade but lacking a functional GPCR were made conditional for growth upon either pheromone pathway activation (activator screen) or pheromone pathway inactivation (inhibitor screen). In addition, the activator yeast strain carries an integrated FUS1p-HIS3 construct, making histidine prototrophy conditional upon pheromone pathway activation. The inhibitor yeast strain carries an episomal FUS1p-CAN1 construct. Adult human liver cDNAs expressed in a yeast vector under control of a galactose-inducible promoter were introduced into these strain, and those cDNAs that conferred growth in a galactose- and insert-dependent fashion were identified. Provided herein is the characterization of one member of these activator cDNAs, encoding a protein of 281 amino acids with significant homology to ras-related G proteins and containing alterations in conserved amino acids consistent with a deficiency in GTP hydrolysis activity (i.e., a constitutively active form of ras-related G protein). Genetic epistasis tests in yeast were consistent with this activator functioning at the level of the heterotrimeric G-protein and facilitating GTP exchange on the chimeric $G\alpha i2$. This protein is referred to herein as Activator of G protein Signaling, or "AGS", or AGS1-AGS1 also shows $G\alpha$ selectivity, as measured by constructs, and tissue specific expression, as measured by Northern blot analysis. A cDNA product identified from the inhibitor screen encodes a previously identified regulator of G-protein signaling, human RGS5.

In one embodiment, an isolated nucleic acid molecule of the present invention encodes an AGS protein (e.g., the nucleic acid molecule has a nucleotide sequence having at least 86% homology with the nucleotide sequence of SEQ ID NO:1 or the complement thereof).

In another embodiment, an isolated nucleic acid molecule of the present invention has a nucleotide sequence having at least 90% homology with the nucleotide sequence of SEQ ID NO:1 or SEQ ID NO:3, or the complement of SEQ ID NO:1 or SEQ ID NO:3.

In yet another embodiment, the isolated nucleic acid molecule has the nucleotide sequence of SEQ ID NO:1, or the complement thereof.

In another embodiment, the isolated nucleic acid molecule has the nucleotide sequence of SEQ ID NO:3, or the complement thereof.

In yet another embodiment, an isolated nucleic acid molecule of the present invention encodes a protein that activates G protein-coupled signal transduction in a G protein-coupled receptor independent manner.

In another embodiment, an isolated nucleic acid molecule of the present invention has a nucleotide sequence which encodes a protein having an amino acid sequence at least 97% identical to the amino acid sequence of SEQ ID NO:2. In another embodiment, the isolated nucleic acid molecule encodes a protein having the amino acid sequence of SEQ ID NO:2.

In yet another embodiment, an isolated nucleic acid molecule of the present invention encodes a protein which activates G protein-coupled signal transduction in a G protein-coupled receptor independent manner.

The present invention also provides vectors including nucleic acid sequences which encode all or a portion of an AGS protein as well as host cells including such vectors.

The invention further provides methods for producing an AGS protein including culturing host cells which express an AGS protein.

The invention also provides transgenic animals which contain cells carrying a transgene encoding AGS protein.

In another embodiment, the present invention provides isolated AGS proteins (e.g., an isolated AGS protein having an amino acid sequence at least 97% homology with the amino acid sequence of SEQ ID NO:2.)

In another embodiment, the protein has the amino acid sequence of SEQ ID NO:2.

The present invention also provides fusion proteins having at least a portion of an AGS protein operatively linked to a non-AGS polypeptide as well as antibodies that specifically bind to an AGS protein (e.g., monoclonal or polyclonal antibodies).

The invention further provides pharmaceutical compositions including AGS proteins or AGS-antibodies.

The present invention further provides methods for identifying compounds that modulate cellular signal transduction.

In one embodiment, the method includes the steps of (a) contacting a cell that expresses an AGS protein with a test compound; (b) determining the effect of the test compound on the activity of the AGS protein; and (c) identifying the test compound as a modulator of signal transduction based on the ability of the compound to modulate the activity of the AGS protein in the cell.

In another embodiment, the AGS proteins utilized in the subject methods have an amino acid sequence which is at least 97% identical to SEQ ID NO:2 and stimulates G protein activity in a receptor-independent manner.

In yet another embodiment, the AGS protein used in the subject methods has the amino acid sequence of SEQ ID NO:2.

In yet another embodiment, the compound identified by the above method is a nucleic acid encoding a polypeptide capable of inhibiting the activity of the AGS protein.

In still another embodiment, the above method further comprises a nucleic acid encoding an inhibitor of the AGS protein.

In a preferred embodiment, the above method is suitable for identifying a test compound capable of modulating the activity of the AGS protein by modulating the inhibitor of the AGS protein.

In a preferred embodiment, cells used in the screening methods of the present invention have been engineered to express the AGS protein. Preferred cells for use in the screening methods are yeast cells.

In another preferred embodiment, the yeast cells have further been engineered to express a G protein α subunit, a chimeric G protein α subunit, or a Gpa1-Gαi2 chimeric G protein a subunit.

The activity of a test compound on a cell-associated activity (e.g., a G-protein mediated activity) can be determined by monitoring a pheromone response pathway in the yeast cells (e.g., by measuring the activity of a pheromone responsive promoter in the yeast cells), by monitoring the ability of the test compound to bind to the AGS protein, or by monitoring the ability of the test compound to modulate the interaction of the AGS protein with a target molecule (e.g., a G protein).

The present invention further provides methods for modulating G protein-coupled signal transduction in a cell (e.g., by contacting a cell with an agent which modulates AGS protein activity or AGS nucleic acid expression).

Methods for treating a subject having a disorder characterized by aberrant AGS protein activity or nucleic acid expression are also provided as well as methods for detecting the presence of AGS in a biological sample.

The present invention also provides an isolated nucleic acid molecules comprising a promotor and a heterologous sequence, wherein the promotor sequence comprises nucleic acids 1–2710 or nucleic acid 1–2709 of SEQ ID NO:73 and their analogues thereof.

The present invention also provides a nucleic acid construct comprising nucleotides which correspond to a promotor, the sequence of which is at least 90% homologous to that of nucleotides 1–2710 as set forth in SEQ ID NO:73.

The present invention also provides a method of transcribing the heterologous sequence from the promoter comprising culturing the host cells which contain said heterologous sequence and said promotor under conditions that result in transcription of said heterologous sequence from the promoter and harvesting said heterologous sequence from said host cells.

This invention further provide a method of determining whether a compound is a modulator of protein biosynthesis specifically transcriptionally modulates the AGS1 gene which comprises (a) contacting a sample which contains a predefined number of cells with a predetermined concentration of the chemical to be tested, each cell comprising a DNA construct consisting essentially of in 5' to 3' order (i) a modulatable transcriptional regulatory sequence of the AGS1 gene, (ii) a promoter, and (iii) a reporter gene which expresses a polypeptide that produces a detectable signal, coupled to, and under the control of, the promoter, under conditions wherein the chemical if capable of acting as a transcriptional modulator of the AGS1 gene, causes a detectable signal to be produced by the polypeptide expressed by the reporter gene; (b) quantitatively determining the amount of the signal produced in (a); and (c) comparing the signal determined in (b) with the signal produced and detected in the absence of any compound being tested or with the signal produced and detected upon contacting the sample in (a) with other compounds, thereby identifying the test compound as one which causes a change in the detectable signal produced by the polypeptide expressed by the reporter gene, and determining whether the test compound specifically transcriptionally modulates expression of the AGS1 gene.

Other features and advantages of the invention will be apparent from the following detailed description and claims.

BRIEF DESCRIPTION OF THE FIGURES

FIG. 1A depicts a diagram (panel A) of the yeast pheromone response pathway with major signaling components, as determined by either functional analysis or sequence homology, are indicated. Signal outputs are denoted in capital letters. Though all of the currently recognized signaling components are indicated, no attempt has been made to portray all of the genetically of biochemically identified protein-protein interactions (Abbr. indicated are: α, Gpa1; β, Ste4; γ, Ste18; P, phosphorylation).

FIG. 1B depicts modifications made to the pheromone response pathway (Panel B) for the Activator screen (i.e., strains CY1316/1183) and the Inhibitor screen (e.g., strains CY1141/1451-AGS1/2440).

FIG. 2A depicts the major steps in carrying out the yeast Activator screen (left panel).

FIG. 2B depicts the major steps in carrying out the yeast inhibitor screen (right panel).

FIG. 3A depicts the growth phenotype of a representative activator. Plasmid pYES2 or cDNA library plasmid pYES-L1 was transformed into CY1316/1183 and plated onto sucrose medium. Transformants were replica-plated onto glucose and galactose media lacking histidine and containing 1 mM aminotriazole (AT). Plates were grown at 30° for 2 days prior to photography.

FIG. 3B depicts the relative strength of pathway activation. Approximately 3000 cells each of three independent isolates of CY1316/1183 carrying either pYES2 (V), pYES2-L1 (L1), pYES2-N34 (N34), pYES2-N37 (N37) or pYES2-N53 (N53 were spotted onto non-selective medium (+His) and glucose (Glu) or galactose (Gal) medium lacking histidine (–His) and containing the indicated amounts of AT.

FIGS. 3C-1 and 3C-2 depict the coding region of the cDNA sequence and predicted amino acid sequence of human AGS. The nucleotide sequence corresponds to SEQ ID NO:1. The amino acid sequence corresponds to SEQ ID NO:2. The composite insert region of cDNA clone pYES2-L1 is available from GenBank, Accession No. #AF069506. Consensus sequences for ras-like G proteins (Valencia, et al. (1991) Biochemistry 30:4637) are underlined. Regions unique to AGS1 are indicated in italics. Three residues that are normally conserved in ras-like G proteins but divergent in AGS1 and Rnd1-3 (Nobes, et al. (1998) J. Cell Biol. 141:187) are indicated with asterisks below the residue. These divergent residues were shown to confer GTPase deficiency in Rnd1.

FIG. 5C depicts the DNA sequence (SEQ ID NO:24) and translation of the insert region of cDNA clone pYES2-L15, encoding human RGS5 (SEQ ID NO:25). Putative start and stop codons are underlines. This sequence has been submitted to GenBank.

FIGS. 7A and 7B depicts the alignment of AGS with representatives of all major classes of small G proteins in humans (SEQ ID NOS: 74-117) indicating that AGS is likely to be the founding member of a novel class of small G proteins in humans.

FIG. 8 depicts the alignment of residues in the P region and in the G' region of various small G proteins (SEQ ID NOS:55–72). Asterisks indicate the location of three highly conserved residues that are altered in AGS, Rnd1, Rnd2, and Rnd3. Numbers indicate the positions of the amino acid sequence of AGS.

FIGS. 9A and 9B depict the DNA sequence of a 4990 bp BamHI-EcoRI genomic fragment containing the human AGS1 coding region, shown in bold. The nucleotide sequence corresponds to SEQ ID NO:73.

DETAILED DESCRIPTION OF THE INVENTION

Figure 4A:
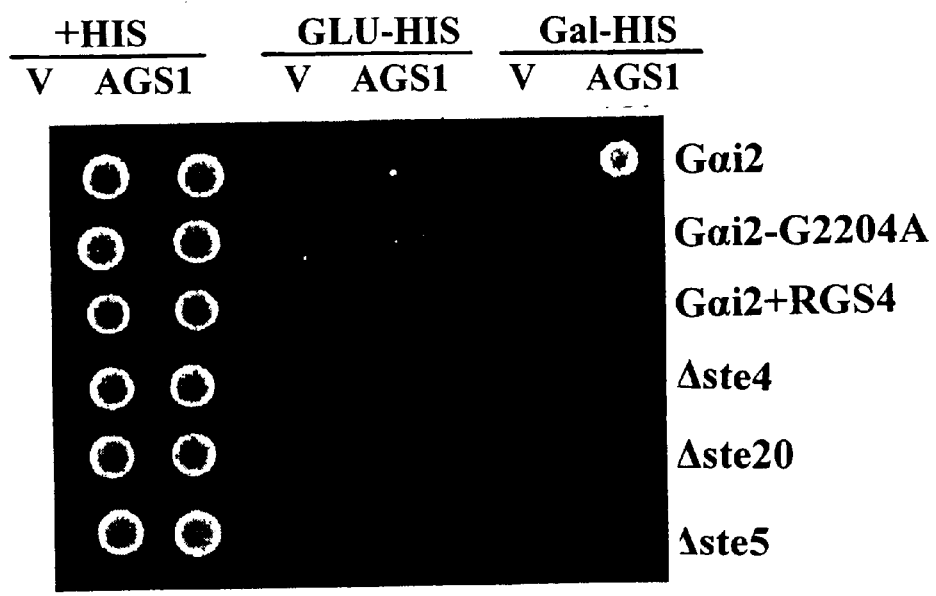
FIG. 4A depicts the epistasis analysis of clone L1 (AGS1) pYES2 or pYES-L1 transformants of strain CY1316/1183 (Gαi2) and its derivatives were spotted onto non-selective medium (+His) and selective glucose (Glu) and galactose (Gal) medium lacking histidine (–His) and containing 1 mM aminotriazole. Plates were grown 2 days at 30° C. prior to photographing. Gαi2-G204A, CY1316/1183 with glyine-204 of Gpa1-Gαi2 changed to alanine; Gαi2+RGS4, CY1316/1183 carrying a high-copy plasmid expressing human RG4; Δste4, CY1316/1183 carrying a genomic deletion of STE4; Δste20, CY1316/1183 carring a genomic deletion of STE20; Δste5, CY1316/1183 carrying a genomic deletion of STE5.
Figure 4B:
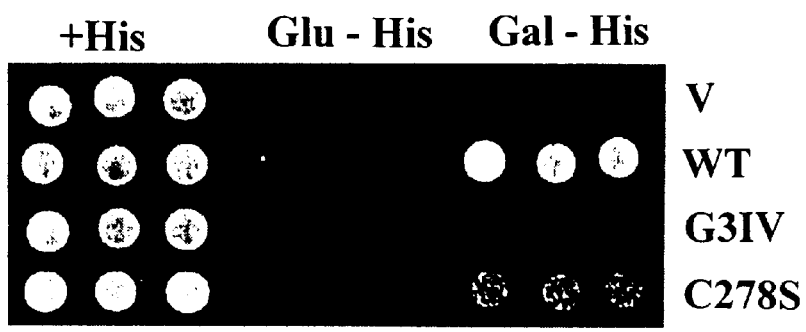
FIG. 4B depicts the growth analysis for AGS1 mutants.
Figure 5A:
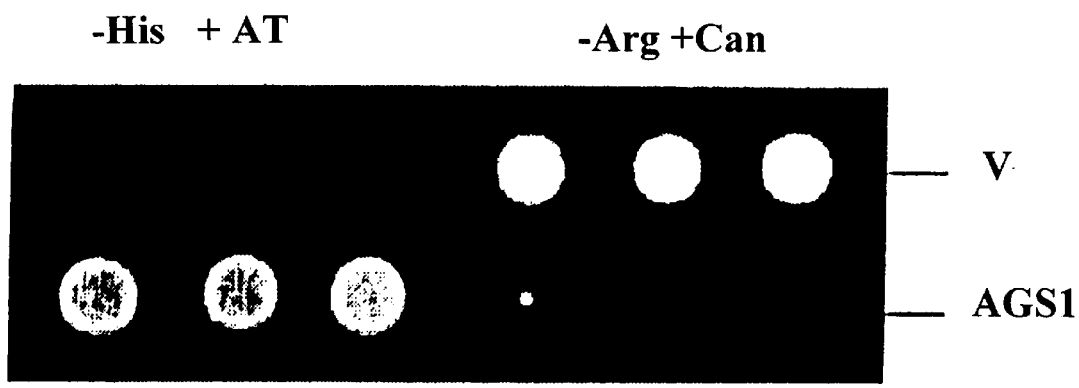
FIG. 5A depicts the pheromone pathway inhibitor screen. Growth phenotypes of screening strain. Approximately 3000 cells each of three independent isolates CY1141/1451/2440 and CY1141/1451-AGS1/2440 were spotted onto glucose medium lacking histidine and containing 2 mM AT and onto glucose medium lacking arginine and containing 200 μg/ml canavanine.
Figure 5B:
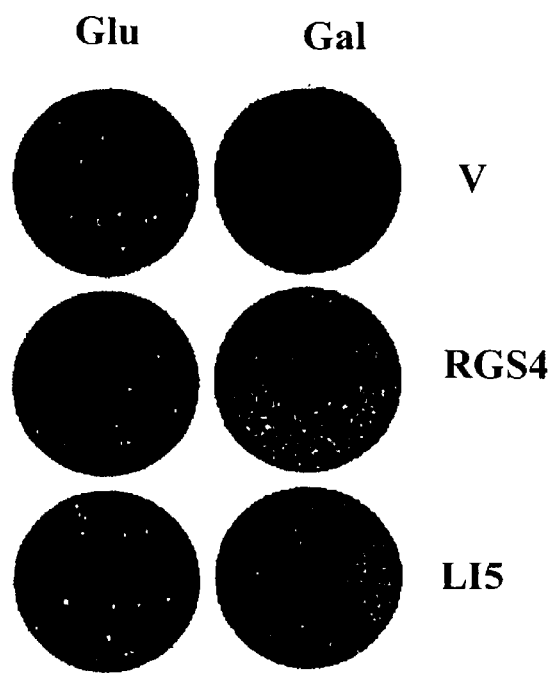
FIG. 5B depicts the pheromone pathway inhibitor screen. Growth phenotype of the isolated pheromone pathway inhibitor. Plasmids pYES2, pYES2-RGS4, and the cDNA library plasmid pYES2-L15 were transformed into CY1141/1451-AGS1/2440 and plated onto sucrose medium. Transformants were replica-plated onto glucose and galactose media lacking arginine and containing 200 μg/ml canavanine. Plates were grown at 30° C. for 2 days prior to photography.
Figure 6A:
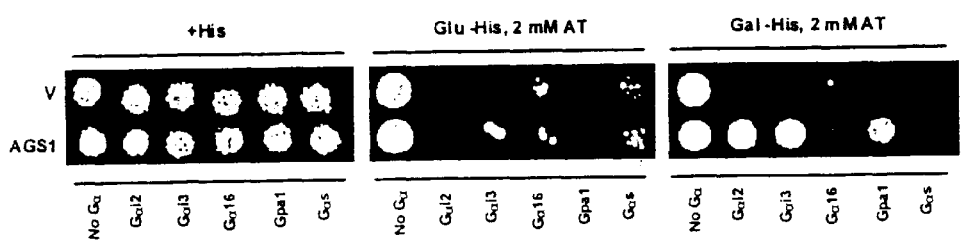
FIG. 6A depicts the Gα selectivity profile of AGS1. Growth phenotype of pYES2-AGS1 in different Gα backgrounds. Approximately 2000 cells each of indicated Gα integrant strans carring either pYES2 (V) or pYES2-AGS1 (AGS1) were spotted onto non-selective medium (+His) and selective glucose (Glu) or galactose (Gal) medium lacking histidine (–His) and containing 2 mM AT. Plates were grown for 2days at 30° C. prior to photographing.
Figure 6B:
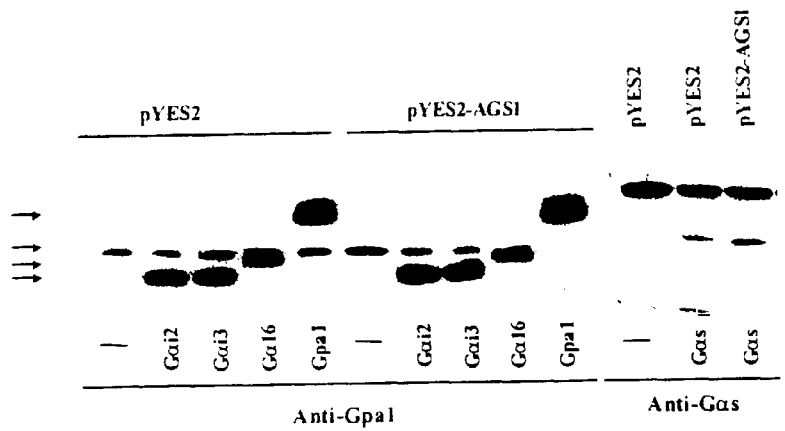
FIG. 6B depicts the Gα selectivity profile of AGS1. Expression levels of integrated Gα constructs. Yeast cultures carrying either pYES2 or pYES2-Ags1 were grown in galactose medium and equivalent amounts of isolated crude membranes were electrophoresed on 10% SDS-polyacrylamide gels for immunoblot anaylsis as described in Experimental protocol. Polyclonal antiserum against Gpa1 was used to detect all Gpa1 chimera and polyclonal antiserum against Gαs was used to detect rat Gαs.-, no Gα;Gαi2, integrated GPA1 (1-41)-Gαi2;Gαi3, integrated GPA1 (1-41)-Gαi3; Gα16, integrated GPA1(1-41)-Gα16 (S270P); Gpa1, integrated full-length GPA1; Gαs, integrated Gαs (E10k). Arrows indicate the position of Gα proteins. Molecular weight standards (in kilodaltons) are shown.

The present invention is based on the discovery of nucleic acid and protein molecules, referred to herein as Activator of G protein Signaling ("AGS") proteins and nucleic acid molecules, which play a role in or function in G protein-mediated signal transduction in the absence of receptor stimulation. These molecules were identified using an assay of the invention that employs yeast-based functional screens using the pheromone response pathway. In part, the assay relies on the observation that a G-protein coupled receptor (GPCR) signaling pathway is required for mating in haploid yeast. Moreover, there is functional redundancy between this pathway and the mammalian GPCR signaling pathway and all of the major signaling components and regulatory systems in GPCR-mediated signal transduction in mammalian systems appears to be conserved in the yeast pheromone response pathway (FIG. 1a) (Kurjan (1993) Annu. Rev. Genet. 27:147–179; Bardwell et al., Dev. Biol. 166:363–379). Thus, this assay can be used to search for mammalian regulators of this system. Normally, upon receptor activation by pheromone, the GPCR associated heterotrimeric G-protein undergoes subunit dissociation into GTP-bound activated Gα (Gpa1) and Gβγ (Ste4/Ste18). Free Gβγ dimer then transduces a signal through a p21-activated kinase (Ste20) to a MAP kinase cascade, leading to the transcriptional activation of mating-specific genes by the transcription factor Ste12, as well as Far1-mediated growth arrest in the $G_1$ phase of the cell cycle. For the screening assay of the present inventions, the pheromone response pathway was engineered to create yeast strains that could be made conditional for growth upon either pheromone pathway activation or suppression (FIG. 1b). Using these strains, functional screens were developed to identify mammalian cDNAs whose expression either activates or down-regulates the yeast pheromone response pathway independent of the presence of receptor. A human AGS cDNA was isolated in a functional cloning screen in yeast based upon its ability to activate G protein signaling in a manner independent of G protein-coupled receptor stimulation. Genetic evidence (described in detail in Examples 1–3) indicates that this AGS-dependent activation occurs at the level of the heterotrimeric G protein. Thus, in one embodiment, the AGS molecules stimulate the activity of one or more G proteins involved in a G protein-mediated signal transduction pathway, e.g., a pheromone response cascade in yeast, to thereby activate G protein-mediated signal transduction independent of G protein coupled receptor stimulation. In a preferred embodiment, the AGS molecules of the present invention stimulate the activity of one or more G proteins involved in a G protein-mediated signal transduction pathway, such that G protein coupled receptor-mediated signal transduction is amplified. In a particularly preferred embodiment, the AGS molecules are capable of modulating the activity of Gα subunits, such as a mammalian Gαi2 subunit or a chimeric Gα subunit comprising a portion of the yeast Gpa1 protein (e.g., the amino-terminal 41 amino acids) linked to a mammalian Gαi2 subunit.

Since the AGS proteins of the invention can function in activation of the pheromone response cascade in yeast cells, and potentially modulate the MEK pathway in mammalian cells, the AGS molecules of the present invention can be used in methods for identifying antagonists of G protein signaling, either receptor-dependent or receptor independent, in screening assays in host cells, such as mammalian or yeast host cells.

A particularly preferred AGS nucleic acid and protein, depicted in FIG. 8 (and shown in SEQ ID NO:1 and SEQ ID NO:2, respectively), is isolated from human cells. FIG. 8 depicts the nucleotide sequence of the coding region of an AGS cDNA which was isolated from a human liver cDNA library. An AGS cDNA nucleotide sequence that includes 5' and 3' untranslated regions is shown in SEQ ID NO:3. The cDNA sequence encodes a predicted protein which is 281 amino acid residues in length and which exhibits homology to ras-related G proteins. The AGS protein also contains alterations in amino acids that typically are conserved among ras-related G proteins that are consistent with AGS having a deficiency in GTP hydrolysis activity.

The AGS proteins of the invention contain several motifs characteristic of Ras superfamily members, including the phosphate/magnesium binding regions GXXXXGK(S/T) (SEQ ID NO:18) (the P-loop) and DXXG (SEQ ID NO:19) (the G' region), as well as the guanine base binding loops NKXD (SEQ ID NO:20) and EXSAK (SEQ ID NO:21) (Bourne et al. (1991) Nature 349:117–127; Valencia et al. (1991) Biochemistry 30:4637–4648). Additionally, the motif regions G-1 through G-5, characteristic of GTPases (Bourne et al. (1991) Nature 349:117–127), are present in AGS. Moreover, the C-terminal region of AGS has a typical CAAX (SEQ ID NO:22) motif (Bourne et al. (1991) Nature 349:117–127; Valencia et al. (1991) Biochemistry 30:4637–4648; Del Villar et al. (1996) Biochem. Soc. Trans. 24:709–713). The CAAX motif is immediately preceded by a basic region QAKDKER (SEQ ID NO:23), thought to be important in anchoring ras-like G proteins to the phospholipid bilayer (Magee and Newman (1992) Trends Cell Biol. 2:318–323).

Various aspects of the invention are described in further detail in the following subsections:

I. Isolated Nucleic Acid Molecules

One aspect of the invention pertains to isolated nucleic acid molecules that encode an AGS protein or biologically active portion thereof, as well as nucleic acid fragments sufficient for use as hybridization probes to identify AGS-encoding nucleic acid (e.g., AGS mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (e.g., sequences located at the 5' and 3' ends of the nucleic acid) in the genomic DNA of the organism from which the nucleic acid is derived. For example, in various embodiments, the isolated AGS nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO:1 or SEQ ID NO:3, or a portion thereof, can be isolated using standard molecular biology techniques and the sequence information provided herein. For example, a human AGS cDNA can be isolated from a human liver cDNA library using all or portion of SEQ ID NO:1 or SEQ ID NO:3 as a hybridization probe and standard hybridization techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989). Moreover, a nucleic acid molecule encompassing all or a portion of SEQ ID NO:1 or SEQ ID NO:3 can be isolated by the polymerase chain reaction using oligonucleotide primers designed based upon the sequence of SEQ ID NO:1 or SEQ ID NO:3. For example, mRNA can be isolated from liver cells (e.g., by the guanidinium-thiocyanate extraction procedure of Chirgwin et al. (1979) Biochemistry 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1 or SEQ ID NO:3. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an AGS nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the coding region of an AGS cDNA isolated from human liver cells. Another preferred AGS cDNA sequence is shown in SEQ ID NO:3, which includes 5' and 3' untranslated regions. This cDNA comprises sequences encoding the AGS protein (e.g., "the coding region", from nucleotides 154 to 999), as well as 5' untranslated sequences (nucleotides 7 to 153) and 3' untranslated sequences (nucleotides 1000 to 1801).

In another preferred embodiment, an isolated nucleic acid molecule of the invention comprises a nucleic acid molecule which is a complement of the nucleotide sequence shown in SEQ ID NO:1 or SEQ ID NO:3, or a portion of any of these nucleotide sequences. A nucleic acid molecule which is the complement of the nucleotide sequence shown in SEQ ID NO:1 or SEQ ID NO:3 is one which has a nucleotide sequence that directly pairs with that of SEQ ID NO:1 or SEQ ID NO:3, according to the rules of Watson and Crick base pairing, wherein A pairs with T and G pairs with C. For example, the complement of the sequence 5' GGATGC 3' would be 3' CCTACG 5" (which, written in the standard 5' to 3' direction, would be 5' GCATCC 3').

In still another preferred embodiment, an isolated nucleic acid molecule of the invention comprises a nucleotide sequence which is at least 60%, preferably at least 70%, more preferably at 80%, and even more preferably at least 90%, or 95%, or 96%, or 97%, or 98%, or 99% homologous to the nucleotide sequence shown in SEQ ID NO:1 or SEQ ID NO:3, or a portion of any of these nucleotide sequences. In an additional preferred embodiment, an isolated nucleic acid molecule of the invention comprises a nucleotide sequence which hybridizes, e.g., hybridizes under stringent conditions, to the nucleotide sequence shown in SEQ ID NO:1 or SEQ ID NO:3, or a portion of any of these nucleotide sequences.

Moreover, the nucleic acid molecule of the invention can comprise only a portion of the coding region of SEQ ID NO:1 or SEQ ID NO:3, for example a fragment which can be used as a probe or primer or a fragment encoding a biologically active portion of an AGS protein. The nucleotide sequence determined from the cloning of the AGS genes from a mammal, e.g., humans, allows for the generation of probes and primers designed for use in identifying and/or cloning AGS homologues in other cell types, e.g. from other tissues, as well as AGS homologues from other mammals, e.g., mice, rats, etc. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of SEQ ID NO:1 or SEQ ID NO:3 sense, an anti-sense sequence of SEQ ID NO:1 or SEQ ID NO:3, or naturally occurring mutants thereof. Primers based on the nucleotide sequence in SEQ ID NO:1 or SEQ ID NO:3 can be used in PCR reactions to clone AGS homologues. Probes based on the AGS nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress an AGS protein, such as by measuring a level of an AGS-encoding nucleic acid in a sample of cells from a subject e.g., detecting AGS mRNA levels or determining whether a genomic AGS gene has been mutated or deleted.

In one embodiment, the nucleic acid molecule of the invention encodes a protein or portion thereof which includes an amino acid sequence which is sufficiently homologous to an amino acid sequence of SEQ ID NO:2 such that the protein or portion thereof maintains the ability to modulate a G-protein mediated response in a cell. As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO:2) amino acid residues to an amino acid sequence of SEQ ID NO:2 such that the protein or portion thereof is able to modulate a G-protein mediated response in a cell. In another embodiment, the protein is at least 60%, preferably at least 70%, more preferably at least 80%, more preferably at least 90% and most preferably at least 95%, or 96%, or 97%, or 98%, or 99% homologous to the entire amino acid sequence of SEQ ID NO:2.

Portions of proteins encoded by the AGS nucleic acid molecule of the invention are preferably biologically active portions of the AGS protein. As used herein, the term "biologically active portion of AGS" is intended to include a portion, e.g., a domain/motif, of AGS that has one or more of the following activities: 1) it can interact with (e.g., bind to) a G protein; 2) it can modulate the activity of a G protein; 3) it can interact with (e.g., bind to) a G protein target molecule; 4) it can modulate the activity of a G protein target molecule; 5) it can modulate a G protein-mediated response in a cell, independent of G protein-coupled receptor activation; and 6) it can augment G protein-coupled receptor signaling by modulating a G protein-mediated response in a cell. Standard binding assays, e.g., immunoprecipitations, yeast two-hybrid assays, and in vitro column binding assays, as described herein, can be performed to determine the ability of an AGS protein or a biologically active portion thereof to interact with (e.g., bind to) a G protein. To determine whether an AGS protein or biologically active portion thereof can modulate G-protein mediated response in a cell, the AGS protein or biologically active portion thereof can be introduced into a cell (e.g., transformed or transfected) which has been engineered to grow only in the presence of an AGS protein or biologically active portion thereof, e.g., yeast cell strain 1316/1183 (described in the Examples) and the ability of the AGS protein or biologically active portion thereof to facilitate growth determined. Alternatively, a cell can be transformed or transfected with a G-protein mediated signal transduction responsive reporter construct (e.g., FUS1-luciferase) which responds to G-protein mediated signaling by expressing luciferase, and a nucleic acid encoding the AGS protein or biologically active portion thereof. The cells can be harvested and lysed and reporter activity, e.g., luciferase activity, can be measured and compared to reporter activity in a control cell. Examples of control cells include cells which include the G-protein mediated signal transduction responsive reporter construct. An alteration in reporter activity in the cells which include nucleic acid encoding the AGS protein, as compared to reporter activity in the cells without nucleic acid encoding the AGS protein is indicative of a modulation of a G-protein mediated response in the cell.

In addition to the AGS nucleotide sequences shown in SEQ ID NO:1 and SEQ ID NO:3, it will be appreciated by those skilled in the art that DNA sequence polymorphisms that lead to changes in the amino acid sequences of AGS may exist within a population. Such genetic polymorphism in the AGS gene may exist among individuals within a population due to natural allelic variation. As used herein, the terms "gene" and "recombinant gene" refer to nucleic acid molecules comprising an open reading frame encoding an AGS protein, preferably a mammalian AGS protein. Such natural allelic variations can typically result in 1–5% variance in the nucleotide sequence of the AGS gene. Any and all such nucleotide variations and resulting amino acid polymorphisms in AGS that are the result of natural allelic variation and that do not alter the functional activity of AGS are intended to be within the scope of the invention. Moreover, nucleic acid molecules encoding AGS proteins from other species, and thus which have a nucleotide sequence which differs from the sequence of SEQ ID NO:1 or SEQ ID NO:3, are intended to be within the scope of the invention. For example, non-human homologues of the AGS cDNAs of the invention can be isolated based on their homology to the AGS nucleic acid disclosed herein using the human cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1 or SEQ ID NO:3. In other embodiments, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 or SEQ ID NO:3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human AGS.

In addition to naturally-occurring allelic variants of the AGS sequences that may exist in the population, the skilled artisan will further appreciate that changes can be introduced by mutation into the nucleotide sequence of SEQ ID NO:1 or SEQ ID NO:3, thereby leading to changes in the amino acid sequence of the encoded AGS proteins, without altering the functional activity of the AGS proteins. For example, nucleotide substitutions leading to amino acid substitutions at "non-essential" amino acid residues can be made in the sequence of SEQ ID NO:1 or SEQ ID NO:3. A "non-essential" amino acid residue is a residue that can be altered from the wild-type sequences of AGS (e.g., the sequence of SEQ ID NO:2) without altering the activity of AGS, whereas an "essential" amino acid residue is required for AGS activity. For example, conserved amino acid residues in the following motifs that are conserved among Ras family members are most likely important for the activity of an AGS protein and are thus essential residues of AGS: the phosphate/magnesium binding regions GXXXXGK(S/T) (SEQ ID NO:18) (the P-loop) and DXXG (SEQ ID NO:19), the guanine base binding loops NKXD (SEQ ID NO:20) and EXSAK (SEQ ID NO:21), the motif regions G-1 through G-5, characteristic of GTPases, and the C-terminal CAAX (SEQ ID NO:22) motif. Other amino acid residues, however, (e.g., those that are not conserved or only semi-conserved family of ras-related small G proteins) may not be essential for activity and thus are likely to be amenable to alteration without altering AGS activity.

Accordingly, another aspect of the invention pertains to nucleic acid molecules encoding AGS proteins that contain changes in amino acid residues that are not essential for AGS activity. Such AGS proteins differ in amino acid sequence from SEQ ID NO:2, yet retain at least one of the AGS activities described herein. In one embodiment, the isolated nucleic acid molecule comprises a nucleotide sequence encoding a protein, wherein the protein comprises an amino acid sequence at least about 60% homologous to the amino acid sequence of SEQ ID NO:2, and is capable of modulating a G-protein mediated response in a cell. Preferably, the protein encoded by the nucleic acid molecule is at least about 70% homologous to SEQ ID NO:2, more preferably at least about 80–85% homologous, even more preferably at least about 90–95% homologous, and most preferably at least about 95, 96, 97, 98, or 99% homologous to SEQ ID NO:2.

To determine the percent homology of two amino acid sequences or of two nucleic acids, the sequences are aligned for optimal comparison purposes (e.g., gaps can be introduced in the sequence of a first or second sequence for optimal alignment). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (e.g., as used herein amino acid or nucleic acid "homology" is equivalent to amino acid or nucleic acid "identity"). The percent homology between the two sequences is a function of the number of identical positions shared by the sequences (e.g., % homology=# of identical positions/total # of positions×100). This number can be modified if using a alignment algorithm which allows for gaps. Alternatively, a percent similarity between two sequences can be determined wherein a non-identical pair of, for example, amino acids sharing a position are evolutionary conserved. Such a comparison can be made utilizing an algorithm which relies on a residue weight table, for example, a PAM residue weight table (e.g., PAM 120 or PAM 150) or a BLOSUM weight residue table (e.g. BLOSUM 62).

The comparison of sequences and determination of percent homology between two sequences can be accomplished using a mathematical algorithm. A preferred, non-limiting example of a mathematical algorithm utilized for the comparison of sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. BLAST nucleotide searches can be performed with the NBLAST program, score=100, wordlength=12 to obtain nucleotide sequences homologous to AGS nucleic acid molecules of the invention. BLAST protein searches can be performed with the XBLAST program, score=50, wordlength=3 to obtain amino acid sequences homologous to ANTIKINE protein molecules of the invention. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Another preferred, non-limiting example of a mathematical algorithm utilized for the alignment of protein sequences is the Lipman-Pearson algorithm (Lipman and Pearson (1985) Science 227:1435–1441). When using the Lipman-Pearson algorithm, a PAM250 weight residue table, a gap length penalty of 12, a gap penalty of 4, and a Ktuple of 2 can be used. A preferred, non-limiting example of a mathematical algorithm utilized for the alignment of nucleic acid sequences is the Wilbur-Lipman algorithm (Wilbur and Lipman (1983) Proc. Natl. Acad. Sci. USA 80:726–730). When using the Wilbur-Lipman algorithm, a window of 20, gap penalty of 3, Ktuple of 3 can be used. Both the Lipman-Pearson algorithm and the Wilbur-Lipman algorithm are incorporated, for example, into the MEGALIGN program (e.g., version 3.1.7) which is part of the DNASTAR sequence analysis software package. Alternatively, a PAM 250 residue weight Table, a GAP penalty of 10, and a GAP length penalty of 10 can be used. Another preferred, non-limiting example of a mathematical algorithm utilized for the comparison of sequences is the algorithm of Wilbur-Lipmann which is part of MegAlign* sequence alignment software. When utilizing the Wilbur-Lipmann algorithm, a K-tuple of 1, a GAP penalty of 3, a window of 5, and diagonals saved set to=5 can be used. Multiple alignment can be performed using the Clustal algorithm.

An isolated nucleic acid molecule encoding an AGS protein homologous to the protein of SEQ ID NO:2 can be created by introducing one or more nucleotide substitutions, additions or deletions into the nucleotide sequence of SEQ ID NO:1 or SEQ ID NO:3, such that one or more amino acid substitutions, additions or deletions are introduced into the encoded protein. Mutations can be introduced into SEQ ID NO:1 or SEQ ID NO:3, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an AGS protein is preferably replaced with another amino acid residue from the same side chain family. Alternatively, in another embodiment, mutations can be introduced randomly along all or part of an AGS coding sequence, such as by saturation mutagenesis, and the resultant mutants can be screened for an AGS activity described herein to identify mutants that retain AGS activity. Following mutagenesis of SEQ ID NO:1 or SEQ ID NO:3, the encoded protein can be expressed recombinantly and the activity of the protein can be determined using, for example, assays described herein.

In addition to the nucleic acid molecules encoding AGS proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire AGS coding strand, or to only a portion thereof. In one embodiment, an antisense nucleic acid molecule is antisense to a "coding region" of the coding strand of a nucleotide sequence encoding an AGS protein. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding AGS. The term "noncoding region" refers to 5' and 3' sequences which flank the coding region that are not translated into amino acids (e.g., also referred to as 5' and 3' untranslated regions).

Given the coding strand sequences encoding AGS proteins disclosed herein (e.g., SEQ ID NO:1 and SEQ ID NO:3), antisense nucleic acids of the invention can be designed according to the rules of Watson and Crick base pairing. The antisense nucleic acid molecule can be complementary to the entire coding region of an AGS mRNA, but more preferably is an oligonucleotide which is antisense to only a portion of the coding or noncoding region of an AGS mRNA. For example, the antisense oligonucleotide can be complementary to the region surrounding the translation start site of an AGS mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Alternatively, the antisense nucleic acid can be produced biologically using an expression vector into which a nucleic acid has been subcloned in an antisense orientation (e.g., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an AGS protein to thereby inhibit expression of the protein, e.g., by inhibiting transcription and/or translation. An example of a route of administration of an antisense nucleic acid molecule of the invention includes direct injection at a tissue site. Alternatively, an antisense nucleic acid molecule can be modified to target selected cells and then administered systemically. e.g. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave AGS mRNA transcripts to thereby inhibit translation of AGS mRNAs. A ribozyme having specificity for an AGS-encoding nucleic acid can be designed based upon the nucleotide sequence of an AGS cDNA disclosed herein. (see, e.g., Cech et al. U.S. Pat. No. 4,987,071 and Cech et al. U.S. Pat. No. 5,116,742). Alternatively, AGS mRNA can be used to select a catalytic RNA having a specific ribonuclease activity from a pool of RNA molecules. (see, e.g., Bartel, D. and Szostak, J. W. (1993) *Science* 261:1411–1418).

Alternatively, AGS gene expression can be inhibited by targeting nucleotide sequences complementary to the regulatory region of an AGS gene (e.g., an AGS promoter and/or enhancer) to form triple helical structures that prevent transcription of an AGS gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

This invention also provide an isolated nucleic acid comprising nucleotides which correspond to a promotor, the sequence of which is at least 90% homologous to that of nucleotides 1–2710 as set forth in SEQ ID NO:73.

In one embodiment of the isolated nucleic acid, the promotor has a sequence which is at least 95% homologous to that of nucleotides 1–2710 as set forth in SEQ ID NO:73.

In another embodiment of the isolated nucleic acid, the promotor has a sequence which is at least 99% homologous to that of nucleotides 1–2710 as set forth in SEQ ID NO:73.

In another embodiment of the isolated nucleic acid, the promotor has a sequence as that of nucleotides 1–2710 of SEQ ID NO:73.

This invention also provide an isolated nucleic acid comprising a coding sequence which is at least 90% homologous to that of nucleotides 2711–3955 of SEQ ID NO:73.

In one embodiment of the isolated nucleic acid, the coding sequence comprises a sequence which is at least 95% homologous to that of nucleotides 2711–3955 of SEQ ID NO:73.

In another embodiment of the isolated nucleic acid, the coding sequence comprises a sequence which is at least 99% homologous to that of nucleotides 2711–3955 of SEQ ID NO:73.

In another embodiment of the isolated nucleic acid, the coding sequence comprises a sequence as that of nucleotides 2711–3955 of SEQ ID NO:73.

This invention further provides an isolated nucleic acid comprising nucleotides having a sequence which is at least 90% homologous to the sequence set forth in SEQ ID NO:73.

In one embodiment of the isolated nucleic acid, the nucleotides have a sequence which is at least 95% homologous to the sequence set forth in SEQ ID NO:73.

In another embodiment of the isolated nucleic acid, the nucleotides have a sequence which is at least 99% homologous to the sequence set forth in SEQ ID NO:73.

In another embodiment of the isolated nucleic acid, the nucleotides have a sequence as set forth in SEQ ID NO:73.

This invention further provides a nucleic acid construct comprising a promotor having a sequence of nucleotides 1–2720 as set forth in SEQ ID NO:73, which is operably linked to a heterologous sequence.

In one embodiment of the nucleic acid construct, the heterologous sequence is a coding sequence.

In another embodiment of the nucleic acid construct, the heterologous sequence encodes a reporter molecule.

In another embodiment of the nucleic acid construct, the coding sequence is a luciferase reporter molecule.

In another embodiment of the nucleic acid construct, the nucleic acid construct further comprises nucleotides 3956–4990 as set forth in SEQ ID NO:73, wherein nucleotide 3956 is linked to the 3' end of said heterologous sequence.

This invention also provides an isolated host cell comprising the nucleic acid construct which comprises a promotor having a sequence of nucleotides 1–2720 as set forth in SEQ ID NO:73, which is operably linked to a heterologous sequence.

This invention also provides a method of transcribing the heterologous sequence from the promoter, comprising culturing the host cells under conditions that result in transcription of said heterologous sequence from the promoter and harvesting said heterologous sequence from said host cells.

In one embodiment of the method, the heterologous sequence is a coding sequence; wherein said host cell is cultured under conditions that result in expression of the encoded peptide or polypeptide product.

In one embodiment of the method, the method further comprises detection of transcription of the heterologous sequence.

In one embodiment of the method, the method further comprises detection of expression of the encoded peptide or polypeptide products.

This invention further provides a method of determining whether a compound is a modulator of protein biosynthesis specifically transcriptionally modulates the AGS1 gene which comprises:

(a) contacting a sample which contains a predefined number of cells with a predetermined concentration of the chemical to be tested, each cell comprising a DNA construct consisting essentially of in 5' to 3' order
  (i) a modulatable transcriptional regulatory sequence of the AGS1 gene,
  (ii) a promoter, and
  (iii) a reporter gene which expresses a polypeptide that produces a detectable signal, coupled to, and under the control of, the promoter, under conditions wherein the chemical if capable of acting as a transcriptional modulator of the AGS1 gene, causes a detectable signal to be produced by the polypeptide expressed by the reporter gene;

(b) quantitatively determining the amount of the signal produced in (a); and (c) comparing the signal determined in (b) with the signal produced and detected in the absence of any compound being tested or with the signal produced and detected upon contacting the sample in (a) with other compounds, thereby identifying the test compound as one which causes a change in the detectable signal produced by the polypeptide expressed by the reporter gene, and determining whether the test compound specifically transcriptionally modulates expression of the AGS1 gene.

In one embodiment of the method, the compound is a chemical compound.

In another embodiment of the method, the compound is not previously known to be a modulator of protein biosynthesis specifically transcriptionally modulates the AGS1 gene.

This invention also provides unknown compounds identified by the method.

This invention further provide an isolated nucleic acid molecule comprising a promotor and a heterologous sequence, wherein the promotor sequence comprises nucleic acids 1–2709 of SEQ ID NO:73.

II. Recombinant Expression Vectors and Host Cells

Another aspect of the invention pertains to vectors, preferably expression vectors, containing a nucleic acid encoding an AGS protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses) as well as baculoviral vectors, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., AGS proteins, mutant forms of AGS proteins, fusion proteins, etc.).

Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of an AGS protein is cloned into a PGEX expression vector to create a vector encoding a fusion protein comprising, from the N-terminus to the C-terminus, GST-thrombin cleavage site-AGS protein. The fusion protein can be purified by affinity chromatography using glutathione-agarose resin. Recombinant AGS protein unfused to GST can be recovered by cleavage of the fusion protein with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, an AGS expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, an AGS protein can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165), pBlueBacHis2 (Invitrogen Corporation, San Diego, Calif.), and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pcDNA3.1/His (Invitrogen Corporation, San Diego, Calif.), pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to an AGS mRNA. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. A host cell can be any prokaryotic or eukaryotic cell. For example, AGS protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding AGS or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (e.g., express) an AGS protein. Accordingly, the invention further provides methods for producing AGS proteins using the host cells of the invention. In one embodiment, the method comprises culturing the host cell of invention (into which a recombinant expression vector encoding an AGS protein has been introduced) in a suitable medium until AGS protein is produced. In another embodiment, the method further comprises isolating AGS protein from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as cardiovascular disorders and proliferative disorders. For example, in one embodiment, a host cell of the invention is a fertilized oocyte or an embryonic stem cell into which AGS-coding sequences have been introduced. Such host cells can then be used to create non-human transgenic animals in which exogenous AGS sequences have been introduced into their genome or homologous recombinant animals in which endogenous AGS sequences have been altered. Such animals are useful for studying the function and/or activity of AGS and for identifying and/or evaluating modulators of AGS activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous AGS gene has been altered by homologous recombination between the endogenous gene and an exogenous DNA molecule introduced into a cell of the animal, e.g., an embryonic cell of the animal, prior to development of the animal.

A transgenic animal of the invention can be created by introducing AGS-encoding nucleic acid into the male pronuclei of a fertilized oocyte, e.g., by microinjection, retroviral infection, and allowing the oocyte to develop in a pseudopregnant female foster animal. The AGS cDNA sequence of SEQ ID NO:1 can be used as a transgene. Alternatively, a non-human homologue of the AGS genes can be isolated based on hybridization to the AGS cDNA (e.g., hybridization to SEQ ID NO:1, described further in subsection I above) and used as a transgene. Intronic sequences and polyadenylation signals can also be included in the transgene to increase the efficiency of expression of the transgene. A tissue-specific regulatory sequence(s) can be operably linked to an AGS transgene to direct expression of AGS protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an AGS transgene in its genome and/or expression of AGS mRNA in tissues or cells of the animals. A transgenic founder animal can then be used to breed additional animals carrying the transgene. Moreover, transgenic animals carrying a transgene encoding AGS can further be bred to other transgenic animals carrying other transgenes.

To create a homologous recombinant animal, a vector is prepared which contains at least a portion of an AGS gene into which a deletion, addition or substitution has been introduced to thereby alter, e.g., functionally disrupt, the AGS gene. The AGS gene can be a human gene (e.g., SEQ ID NO:1), but more preferably, is a nonhuman homologue of a human AGS gene (e.g., a murine homologue). For example, a mouse AGS gene can be used to construct a homologous recombination vector suitable for altering an endogenous AGS gene in the mouse genome. In a preferred embodiment, the vector is designed such that, upon homologous recombination, the endogenous AGS gene is functionally disrupted (e.g., no longer encodes a functional protein; also referred to as a "knock out" vector). Alternatively, the vector can be designed such that, upon homologous recombination, the endogenous AGS gene is mutated or otherwise altered but still encodes functional protein (e.g., the upstream regulatory region can be altered to thereby alter the expression of the endogenous AGS protein). In the homologous recombination vector, the altered portion of the AGS gene is flanked at its 5' and 3' ends by additional nucleic acid of the AGS gene to allow for homologous recombination to occur between the exogenous AGS gene carried by the vector and an endogenous AGS gene in an embryonic stem cell. The additional flanking AGS nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced AGS gene has homologously recombined with the endogenous AGS gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhumans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Clones of the nonhuman transgenic animals described herein can also be produced according to the methods described in Wilmut, I. et al. (1997) *Nature* 385:810–813.

III. Isolated AGS Proteins and Anti-AGS Antibodies

Another aspect of the invention pertains to isolated AGS proteins, and biologically active portions thereof, as well as peptide fragments suitable for use as immunogens to raise anti-AGS antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of AGS protein in which the protein is separated from cellular components of the cells in which it is naturally or recombinantly produced. In one embodiment, the language "substantially free of cellular material" includes preparations of AGS protein having less than about 30% (by dry weight) of non-AGS protein (also referred to herein as a "contaminating protein"), more preferably less than about 20% of non-AGS protein, still more preferably less than about 10% of non-AGS protein, and most preferably less than about 5% non-AGS protein. When the AGS protein or biologically active portion thereof is recombinantly produced, it is also preferably substantially free of culture medium, e.g., culture medium represents less than about 20%, more preferably less than about 10%, and most preferably less than about 5% of the volume of the protein preparation. The language "substantially free of chemical precursors or other chemicals" includes preparations of AGS protein in which the protein is separated from chemical precursors or other chemicals which are involved in the synthesis of the protein.

In one embodiment, the language "substantially free of chemical precursors or other chemicals" includes preparations of AGS protein having less than about 30% (by dry weight) of chemical precursors or non-AGS chemicals, more preferably less than about 20% chemical precursors or non-AGS chemicals, still more preferably less than about 10% chemical precursors or non-AGS chemicals, and most preferably less than about 5% chemical precursors or non-AGS chemicals. In preferred embodiments, isolated proteins or biologically active portions thereof lack contaminating proteins from the same animal from which the AGS protein is derived. Typically, such proteins are produced by recombinant expression of, for example, a human AGS protein in a nonhuman cell.

An isolated AGS protein or a portion thereof of the invention can modulate a G-protein mediated response in a cell. In preferred embodiments, the protein or portion thereof comprises an amino acid sequence which is sufficiently homologous to an amino acid sequence of SEQ ID NO:2 such that the protein or portion thereof maintains the ability to modulate a G-protein mediated response in a cell. The portion of the protein is preferably a biologically active portion as described herein. In another preferred embodiment, the AGS protein has an amino acid sequence shown in SEQ ID NO:2. In yet another preferred embodiment, the AGS protein has an amino acid sequence which is encoded by a nucleotide sequence which hybridizes, e.g., hybridizes under stringent conditions, to the nucleotide sequence of SEQ ID NO:1 or SEQ ID NO:3. In still another preferred embodiment, the AGS protein has an amino acid sequence which is encoded by a nucleotide sequence that is at least 60%, preferably at least 70%, more preferably at least 80%, and even more preferably at least 90%, or 95%, or 96%, or 97%, or 98%, or 99% homologous to the nucleotide sequence of SEQ ID NO:1 or SEQ ID NO:3. The preferred AGS proteins of the present invention also preferably possess at least one of the AGS activities described herein. For example, a preferred AGS protein of the present invention includes an amino acid sequence encoded by a nucleotide sequence which hybridizes, e.g., hybridizes under stringent conditions, to the nucleotide sequence SEQ ID NO:1 or SEQ ID NO:3 and which can modulate a G-protein mediated response in a cell.

In other embodiments, the AGS protein is substantially homologous to the amino acid sequence of SEQ ID NO:2 and retains the functional activity of the protein of SEQ ID NO:2 yet differs in amino acid sequence due to natural allelic variation or mutagenesis, as described in detail in subsection I above. Accordingly, in another embodiment, the AGS protein is a protein which comprises an amino acid sequence which is at least 60%, preferably at least 80%, and more preferably at least 86%, or 88%, or 90%, and most preferably at least 95%, or 96%, or 97%, or 98%, or 99% homologous to the entire amino acid sequence of SEQ ID NO:2 and which has at least one of the AGS activities described herein. In other embodiments, the invention pertains to a full length human protein which is substantially homologous to the entire amino acid sequence of SEQ ID NO:2.

Biologically active portions of the AGS protein include peptides comprising amino acid sequences derived from the amino acid sequence of the AGS protein, e.g., the amino acid sequence shown in SEQ ID NO:2 or the amino acid sequence of a protein homologous to the AGS protein, which include less amino acids than the full length AGS protein or the full length protein which is homologous to the AGS protein, and exhibit at least one activity of the AGS protein. Typically, biologically active portions (peptides, e.g., peptides which are, for example, 5, 10, 15, 20, 30, 35, 36, 37, 38, 39, 40, 50, 100 or more amino acids in length) comprise a domain or motif, with at least one activity of the AGS protein. In a preferred embodiment, the biologically active portion of the protein includes a motif selected from the following: the phosphate/magnesium binding regions GXXXXGK(S/T) (SEQ ID NO:18) (the P-loop) and DXXG (SEQ ID NO:19), the guanine base binding loops NKXD (SEQ ID NO:20) and EXSAK (SEQ ID NO:21) the motif regions G-1 through G-5, characteristic of GTPases, the C-terminal CAAX (SEQ ID NO:22) motif, and/or the QAKDKER motif (SEQ ID NO:23) and can modulate the activity of a G-protein. Moreover, other biologically active portions, in which other regions of the protein are deleted, can be prepared by recombinant techniques and evaluated for one or more of the activities described herein. Preferably, the biologically active portions of the AGS protein include one or more selected domains/motifs or portions thereof having biological activity.

AGS proteins are preferably produced by recombinant DNA techniques. For example, a nucleic acid molecule encoding the protein is cloned into an expression vector (as described above), the expression vector is introduced into a host cell (as described above) and the AGS protein is expressed in the host cell. The AGS protein can then be isolated from the cells by an appropriate purification scheme using standard protein purification techniques. Alternative to recombinant expression, an AGS protein, polypeptide, or peptide can be synthesized chemically using standard peptide synthesis techniques. Moreover, native AGS protein can be isolated from cells, for example using an anti-AGS antibody (described further below).

The invention also provides AGS chimeric or fusion proteins. As used herein, an AGS "chimeric protein" or "fusion protein" comprises an AGS polypeptide operatively linked to a non-AGS polypeptide. An "AGS polypeptide" refers to a polypeptide having an amino acid sequence corresponding to AGS, whereas a "non-AGS polypeptide" refers to a polypeptide having an amino acid sequence corresponding to a protein which is not substantially homologous to the AGS protein, e.g., a protein which is different from the AGS protein and which is derived from the same or a different organism. Within the fusion protein, the term "operatively linked" is intended to indicate that the AGS polypeptide and the non-AGS polypeptide are fused in-frame to each other. The non-AGS polypeptide can be fused to the N-terminus or C-terminus of the AGS polypeptide. For example, in one embodiment the fusion protein is a GST-AGS fusion protein in which the AGS sequences are fused to the C-terminus of the GST sequences. Such fusion proteins can facilitate the purification of recombinant AGS. In another embodiment, the fusion protein is an AGS protein containing a heterologous signal sequence at its N-terminus.

In certain host cells (e.g., mammalian host cells), expression and/or secretion of AGS can be increased through use of a heterologous signal sequence.

Preferably, an AGS chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An AGS-encoding nucleic acid can be cloned into such an expression vector such that the fusion moiety is linked in-frame to the AGS protein.

The present invention also pertains to homologues of the AGS proteins which function as either an AGS agonist (mimetic) or an AGS antagonist. In a preferred embodiment, the AGS agonists and antagonists stimulate or inhibit, respectively, a subset of the biological activities of the naturally occurring form of the AGS protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the AGS protein.

Homologues of the AGS protein can be generated by mutagenesis, e.g., discrete point mutation or truncation of the AGS protein. As used herein, the term "homologue" refers to a variant form of the AGS protein which acts as an agonist or antagonist of the activity of the AGS protein. An agonist of the AGS protein can retain substantially the same, or a subset, of the biological activities of the AGS protein. An antagonist of the AGS protein can inhibit one or more of the activities of the naturally occurring form of the AGS protein, by, for example, competitively binding to a G-protein or downstream or upstream member of the pheromone response cascade.

In an alternative embodiment, homologues of the AGS protein can be identified by screening combinatorial libraries of mutants, e.g., truncation mutants, of the AGS protein for AGS protein agonist or antagonist activity. In one embodiment, a variegated library of AGS variants is generated by combinatorial mutagenesis at the nucleic acid level and is encoded by a variegated gene library. A variegated library of AGS variants can be produced by, for example, enzymatically ligating a mixture of synthetic oligonucleotides into gene sequences such that a degenerate set of potential AGS sequences is expressible as individual polypeptides, or alternatively, as a set of larger fusion proteins (e.g., for phage display) containing the set of AGS sequences therein. There are a variety of methods which can be used to produce libraries of potential AGS homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential AGS sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the AGS protein coding can be used to generate a variegated population of AGS fragments for screening and subsequent selection of homologues of an AGS protein. In one embodiment, a library of coding sequence fragments can be generated by treating a double stranded PCR fragment of an AGS coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the AGS protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of AGS homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify AGS homologues (Arkin and Yourvan (1992) *PNAS* 89:7811–7815; Delgrave et al. (1993) *Protein Engineering* 6(3):327–331).

An isolated AGS protein, or a portion or fragment thereof, can be used as an immunogen to generate antibodies that bind AGS using standard techniques for polyclonal and monoclonal antibody preparation. The full-length AGS protein can be used or, alternatively, the invention provides antigenic peptide fragments of AGS for use as immunogens. The antigenic peptide of AGS comprises at least 8 amino acid residues of the amino acid sequence shown in SEQ ID NO:2 and encompasses an epitope of AGS such that an antibody raised against the peptide forms a specific immune complex with AGS. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of AGS that are located on the surface of the protein, e.g., hydrophilic regions and/or regions that are unique to AGS, e.g. not common to all small G proteins.

An AGS immunogen typically is used to prepare antibodies by immunizing a suitable subject, (e.g., rabbit, goat, mouse or other mammal) with the immunogen. An appropriate immunogenic preparation can contain, for example, recombinantly expressed AGS protein or a chemically synthesized AGS peptide. The preparation can further include an adjuvant, such as Freund's complete or incomplete adjuvant, or similar immunostimulatory agent. Immunization of a suitable subject with an immunogenic AGS preparation induces a polyclonal anti-AGS antibody response.

Accordingly, another aspect of the invention pertains to anti-AGS antibodies. The term "antibody" as used herein refers to immunoglobulin molecules and immunologically active portions of immunoglobulin molecules, e.g., molecules that contain an antigen binding site which specifically binds (immunoreacts with) an antigen, such as AGS. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind AGS. The term "monoclonal antibody" or "monoclonal antibody composition", as used herein, refers to a population of antibody molecules that contain only one species of an antigen binding site capable of immunoreacting with a particular epitope of AGS. A monoclonal antibody composition thus typically displays a single binding affinity for a particular AGS protein with which it immunoreacts.

Polyclonal anti-AGS antibodies can be prepared as described above by immunizing a suitable subject with an AGS immunogen. The anti-AGS antibody titer in the immunized subject can be monitored over time by standard techniques, such as with an enzyme linked immunosorbent assay (ELISA) using immobilized AGS. If desired, the antibody molecules directed against AGS can be isolated from the mammal (e.g., from the blood) and further purified by well known techniques, such as protein A chromatography to obtain the IgG fraction. At an appropriate time after immunization, e.g., when the anti-AGS antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.*, 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36).

Any of the many well known protocols used for fusing lymphocytes and immortalized cell lines can be applied for the purpose of generating an anti-AGS monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Hybridoma cells producing a monoclonal antibody of the invention are detected by screening the hybridoma culture supernatants for antibodies that bind AGS, e.g., using a standard ELISA assay.

Alternative to preparing monoclonal antibody-secreting hybridomas, a monoclonal anti-AGS antibody can be identified and isolated by screening a recombinant combinatorial immunoglobulin library (e.g., an antibody phage display library) with AGS to thereby isolate immunoglobulin library members that bind AGS. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature (*1990) 348:552–554.

Additionally, recombinant anti-AGS antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-AGS antibody (e.g., monoclonal antibody) can be used to isolate AGS by standard techniques, such as affinity chromatography or immunoprecipitation. An anti-AGS antibody can facilitate the purification of natural AGS from cells and of recombinantly produced AGS expressed in host cells. Moreover, an anti-AGS antibody can be used to detect AGS protein (e.g., in a cellular lysate or cell supernatant) in order to evaluate the abundance, pattern of expression, and/or subcellular localization of the AGS protein. Anti-AGS antibodies can be used diagnostically to monitor protein levels in tissue as part of a clinical testing procedure, e.g., to, for example, determine the efficacy of a given treatment regimen. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

IV. Pharmaceutical Compositions

The AGS nucleic acid molecules, AGS proteins, AGS modulators, and anti-AGS antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene.glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an AGS protein or anti-AGS antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

An AGS protein of the invention has one or more of the activities described herein and can thus be used, for example, to screen drugs or compounds which modulate AGS protein activity as well as to treat disorders characterized by insufficient or excessive production of AGS protein or production of AGS protein forms which have altered (e.g., increased or decreased) activity compared to wild type AGS. In addition, methods are provided that employ AGS molecules and rely on strategies based upon functional readouts using the yeast Saccharomyces cerevisiae, and these methods offer a fast and more reliable way to identify genes whose expression affects key aspects of cellular function. Accordingly, these methods have distinct advantages over transcriptional profiling screens, computer-based screens, screens based on protein-protein interactions, and other transgenic and cell-based functional screens that have been developed in higher eukaryotes (Spence (1998) *Drug Disc. Today* 3:179–188; Simonsen et al. (1994) *Trends Pharmacol. Sci.* 15:437–441; Evans et al. (1997) *Trends Genet.* 13:370–374; Hicks et al. (1997) *Nat. Genet.* 16:338–344; and Whitney et al. (1998) *Nat. Biotech.* 16:1329–1333). Moreover, the isolated nucleic acid molecules of the invention can be used to express AGS protein (e.g., via a recombinant expression vector in a host cell in gene therapy applications), to detect AGS mRNA (e.g., in a biological sample) or a genetic lesion in an AGS gene, and to modulate AGS activity, as described further below. Moreover, the anti-AGS antibodies of the invention can be used to detect and isolate AGS protein and modulate AGS protein activity.

a) Drug Screening Assays

The invention provides methods for identifying compounds or agents which modulate AGS protein activity and/or AGS nucleic acid expression. These methods are also referred to herein as drug screening assays and typically include the step of screening a candidate/test compound or agent for the ability to interact with (e.g., bind to) an AGS protein, to modulate the interaction of an AGS protein and a target molecule, and/or to modulate AGS nucleic acid expression and/or AGS protein activity, and/or to modulate signal transduction mediated at least in part by an AGS protein. Candidate/test compounds or agents which have one or more of these abilities can be used as drugs to treat disorders characterized by aberrant or abnormal AGS protein activity and/or AGS nucleic acid expression. Candidate/test compounds such as small molecules, e.g., small organic molecules, and other drug candidates can be obtained, for example, from combinatorial and natural product libraries.

In a preferred embodiment, the invention provides a method for identifying a compound that modulates signal transduction in a cell, comprising the steps of contacting a cell that expresses an AGS protein with a test compound and determining the effect of the test compound on the activity of the AGS protein and identifying the test compound as a modulator of signal transduction based on the ability of the compound to modulate the activity of the AGS protein in the cell.

As used herein, the term "identify" as used in the context of "identifying a compound" refers to the identification of compounds for which an activity as an activator of G protein signaling has not been previously recognized or demonstrated. The term "identifying" according to the methods of the present invention is intended to refer to identifying, screening and/or selecting of test compound, for example selecting active compounds not previously recognized as activators of G protein signaling for further analysis and testing. In a preferred non-limiting example, compounds "identified" according to the methods of the present invention can be used as test compounds in a second assay to confirm a G protein activating activity. Alternatively, compounds "identified" according to the methods of the present invention can be tested for other desirable activities or can be tested, for example, at varying doses to determine the efficacy of the compound. Compounds "identified" according to the methods of the present invention can be also tested in cell culture models or in animal models of disease.

In a preferred embodiment, the AGS protein comprises an amino acid sequence having at least 86% homology with SEQ ID NO:2 and stimulates G protein activity in a receptor-independent manner. In a particularly preferred embodiment, the AGS protein comprises the amino acid sequence of SEQ ID NO 2. Alternatively, the AGS protein can comprise a structure as described above in the sections discussing AGS proteins and nucleic acids.

In a preferred embodiment, of the cell-based screening method, the cell has been engineered to express the AGS protein by introducing into the cell an expression vector encoding the AGS protein. The cell can be further engineered to express other proteins, such as a G protein α subunit. In a preferred embodiment, the cell is a yeast cell that has been engineered to express an AGS protein and a mammalian or chimeric G protein α subunit and the effect of the test compound on the activity of the AGS protein is determined by monitoring a pheromone response pathway in the yeast cells. A preferred chimeric G protein subunit which the yeast cell is engineered to express is a Gpa1-Gαi2 chimeric G protein a subunit (preferably comprising 41 amino-terminal amino acids from yeast Gpa1 operatively linked to a mammalian Gαi2). The pheromone response pathway in the yeast cells can be monitored, for example, by measuring the activity of a pheromone responsive promoter in the yeast cells. Yeast cell compositions and methods that can be used for screening modulators of AGS proteins are described in further detail below and in the Examples.

In an alternative embodiment, the effect of the test compound on the activity of the AGS protein is determined by monitoring the ability of the test compound to bind to the AGS protein.

In another alternative embodiment, the effect of the test compound on the activity of the AGS protein is determined by monitoring the ability of the test compound to modulate the interaction of the AGS protein with a target molecule. Preferably, the target molecule is a G protein.

In another embodiment, the invention provides assays for screening candidate/test compounds which interact with (e.g., bind to) AGS protein. Typically, the assays are cell-free assays which include the steps of combining an AGS protein or a biologically active portion thereof, and a candidate/test compound, e.g., under conditions which allow for interaction of (e.g., binding of) the candidate/test compound to the AGS protein or portion thereof to form a complex, and detecting the formation of a complex, in which the ability of the candidate compound to interact with (e.g., bind to) the AGS protein or portion thereof is indicated by the presence of the candidate compound in the complex. Formation of complexes between the AGS protein and the candidate compound can be quantitated, for example, using standard immunoassays.

In another embodiment, the invention provides screening assays to identify candidate/test compounds which modulate (e.g., stimulate or inhibit) the interaction (and most likely AGS activity as well) between an AGS protein and a molecule (target molecule) with which the AGS protein normally interacts. Examples of such target molecules includes proteins in the same signaling pathway as the AGS protein, e.g., G proteins, or proteins which may function upstream (including both stimulators and inhibitors of activity) or downstream of the G protein in the pheromone response pathway. Typically, the assays are cell-free assays which include the steps of combining an AGS protein or a biologically active portion thereof, an AGS target molecule (e.g., a G protein) and a candidate/test compound, e.g., under conditions wherein but for the presence of the candidate compound, the AGS protein or biologically active portion thereof interacts with (e.g., binds to) the target molecule, and detecting the formation of a complex which includes the AGS protein and the target molecule or detecting the interaction/reaction of the AGS protein and the target molecule. Detection of complex formation can include direct quantitation of the complex by, for example, measuring inductive effects of the AGS protein. A statistically significant change, such as a decrease, in the interaction of the AGS and target molecule (e.g., in the formation of a complex between the AGS and the target molecule) in the presence of a candidate compound (relative to what is detected in the absence of the candidate compound) is indicative of a modulation (e.g., stimulation or inhibition) of the interaction between the AGS protein and the target molecule. Modulation of the formation of complexes between the AGS protein and the target molecule can be quantitated using, for example, an immunoassay.

To perform the above drug screening assays, it may be desirable to immobilize either AGS or its target molecule to facilitate separation of complexes from uncomplexed forms of one or both of the proteins, as well as to accommodate automation of the assay. Interaction (e.g., binding of) of AGS to a target molecule, in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows the protein to be bound to a matrix. For example, glutathione-S-transferase/AGS fusion proteins can be adsorbed onto glutathione sepharose beads (Sigma Chemical, St. Louis, Mo.) or glutathione derivatized microtitre plates, which are then combined with the cell lysates (e.g. $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of AGS-binding protein found in the bead fraction quantitated from the gel using standard electrophoretic techniques.

Other techniques for immobilizing proteins on matrices can also be used in the drug screening assays of the invention. For example, either AGS or its target molecule can be immobilized utilizing conjugation of biotin and streptavidin. Biotinylated AGS molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with AGS but which do not interfere with binding of the protein to its target molecule can be derivatized to the wells of the plate, and AGS trapped in the wells by antibody conjugation. As described above, preparations of an AGS-binding protein and a candidate compound are incubated in the AGS-presenting wells of the plate, and the amount of complex trapped in the well can be quantitated. Methods for detecting such complexes, in addition to those described above for the GST-immobilized complexes, include immunodetection of complexes using antibodies reactive with the AGS target molecule, or which are reactive with AGS protein and compete with the target molecule; as well as enzyme-linked assays which rely on detecting an enzymatic activity associated with the target molecule.

The invention also provides cell-based assays for identifying compounds which modulate AGS activity. In one embodiment, the cell-based assay involves a method for identifying a compound which modulates (e.g., stimulates or inhibits) AGS activity including contacting a cell which contains an AGS protein with a test compound and determining the ability of the test compound to modulate the activity of the AGS protein. In a preferred embodiment, determining the ability of the test compound to modulate AGS activity includes determining the ability of the test compound to effect (e.g., upregulate or down regulate) G-protein mediated signaling in the cell. For example, G-protein mediated signaling can be determined in an AGS-containing cell prior to contacting the cell with a test compound and compared to the signaling after contacting the cell with a test compound. Compounds which reduce the G-protein mediated signaling can be identified as AGS antagonists whereas compounds which increase the G-protein mediated signaling can be identified as antagonists.

Alternatively, modulators of AGS expression can be identified in a method wherein a cell is contacted with a candidate compound and the expression of AGS mRNA or protein in the cell is determined. The level of expression of AGS mRNA or protein in the presence of the candidate compound is compared to the level of expression of AGS mRNA or protein in the absence of the candidate compound. The candidate compound can then be identified as a modulator of AGS nucleic acid expression based on this comparison. For example, when expression of AGS mRNA or protein is greater (statistically significantly greater) in the presence of the candidate compound than in its absence, the candidate compound is identified as a stimulator of AGS mRNA or protein expression.

Alternatively, when expression of AGS mRNA or protein is less (statistically significantly less) in the presence of the candidate compound than in its absence, the candidate compound is identified as an inhibitor of AGS mRNA or protein expression. The level of AGS mRNA or protein expression in the cells can be determined by methods described herein for detecting AGS mRNA or protein.

The present invention also provides cell-based assays for identifying compounds which modulate the activity of an AGS. Typically, cells for use in cell based assays are engineered to express a heterologous AGS protein. In preferred embodiments, the cells may be further engineered such that the endogenous AGS protein is not expressed in functional form. Cells used to express a heterologous AGS can be, for example, mammalian or yeast in origin. In preferred embodiments, the engineered cells of the present invention are yeast cells.

In certain embodiments, the cells for use in the instant assays are further engineered to express a heterologous G protein coupled receptor which is functionally integrated into the signaling pathway of the cell in which it is expressed. In the case of yeast cells, heterologous GPCRs can be expressed in yeast cells and can be made to couple to yeast G proteins resulting in the transduction of signals via the endogenous yeast pheromone system signaling pathway which is normally activated by STE2 or STE3. In certain embodiments, such heterologous receptors can be made to couple more effectively to the yeast pheromone system signaling pathway by coexpressing a heterologous G protein subunit or subunits, by expressing a chimeric G protein subunit, or by expressing a chimeric G protein coupled receptor. Methods for preparing engineered yeast cells, and engineered yeast cells themselves, are described in U.S. Pat. No. 5,482,835 by King et al. and PCT Publication WO 94/23025 by Fowlkes et al., the contents of both of which are hereby expressly incorporated herein by reference.

In one embodiment of the assay, the effect of a test compound on AGS induced G protein activation can be measured by detecting changes in second messenger generation. Alternatively, in another embodiment, the effect of a test compound on an inhibitor of an activator of G-protein signaling can be detected. A variety of intracellular effectors have been identified as being G-protein-regulated, including adenylyl cyclase, cyclic GMP, phosphodiesterases, phosphoinositidase C, and phospholipase $A_2$. In addition, G proteins interact with a range of ion channels and are able to inhibit certain voltage-sensitive $Ca^{++}$ transients, as well as stimulating cardiac $K^+$ channels. For example, in yeast cells a reduction in the generation of AGS-induced second messengers or mating factor responses (e.g., growth arrest or shmoo formation) could be measured.

In one embodiment, GTP binding or GTPase enzymatic activity of G proteins can be measured in plasma membrane preparations by determining, respectively, the incorporation of $GTP\gamma^{35}S$ or breakdown of $\gamma^{32}P$ GTP using techniques that are known in the art (For example, see *Signal Transduction: A Practical Approach*, G. Milligan, Ed. Oxford University Press, Oxford England). When receptors that modulate cAMP are tested, it will be possible to use standard techniques for cAMP detection, such as competitive assays which quantitate [$^3H$]cAMP in the presence of unlabelled cAMP.

Certain receptors stimulate the activity of phospholipase C which stimulates the breakdown of phosphatidylinositol 4,5, bisphosphate to 1,4,5-IP3 (which mobilizes intracellular $Ca^{++}$) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

The mobilization of intracellular calcium or the influx of calcium from outside the cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84:45–56). As an exemplary method of Ca++ detection, cells could be loaded with the $Ca^{++}$ sensitive fluorescent dye fura-2 or indo-1, using standard methods, and any change in $Ca^{++}$ measured using a fluorometer.

The other product of PIP2 breakdown, DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In the case of certain receptors, it may be desirable to screen for changes in cellular phosphorylation. Such assay formats may be useful when the receptor of interest is a receptor tyrosine kinase. For example, yeast transformed with the FGF receptor and a ligand which binds the FGF receptor could be screened using colony immunoblotting (Lyons and Nelson (1984) *Proc. Natl. Acad. Sci. USA* 81:7426–7430) using anti-phosphotyrosine. In addition, tests for phosphorylation could be useful when a receptor which may not itself be a tyrosine kinase, activates protein kinases that function downstream in the signal transduction pathway. Likewise, it is noted that protein phosphorylation also plays a critical role in cascades that serve to amplify signals generated at the receptor. Multi-kinase cascades allow not only signal amplification but also signal divergence to multiple effectors that are often cell-type specific, allowing a growth factor to stimulate mitosis of one cell and differentiation of another.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases (ERK1 and ERK2). Activated MAP kinase then phosphorylates many key regulatory proteins, including p90RSK and Elk-1 that are phosphorylated when MAP kinase translocates to the nucleus. Homologous pathways exist in mammalian and yeast cells. For instance, an essential part of the *S. cerevisiae* pheromone signaling pathway is comprised of a protein kinase cascade composed of the products of the STE11, STE7, and FUS3/KSS1 genes (the latter pair are distinct and functionally redundant). Accordingly, phosphorylation and/or activation of members of this kinase cascade can be detected and used to quantitate receptor engagement. Phosphotyrosine specific antibodies are available to measure increases in tyrosine phosphorylation and phospho-specific antibodies are commercially available (New England Biolabs, Beverly, Mass.).

Modified methods for detecting receptor-mediated signal transduction exist and one of skill in the art will recognize suitable methods that may be used to substitute for the example methods listed.

In another embodiment, an indicator gene can be used for detection. In one embodiment an indicator gene is an unmodified endogenous gene. For example, in yeast cells, the instant method can rely on detecting the transcriptional level of such pheromone system pathway responsive endogenous genes as the BAR1 or FUS1, FUS2, mating factor, STE3 STE13, KEX1, STE2, STE6, STE7, SST2, or CHS1. (Appletauer and Zchstetter. (1989) Eur. J. Biochem., 181:243).

In other embodiments, the sensitivity of an endogenous indicator gene can be enhanced by manipulating the promoter sequence at the natural locus for the indicator gene. Such manipulation may range from point mutations to the endogenous regulatory elements to gross replacement of all or substantial portions of the regulatory elements.

For example, in the case of the BAR1 gene, the promoter of the gene can be modified to enhance the transcription of BAR1 upon activation of the yeast pheromone system pathway. BAR1 gene transcription is activated upon exposure of yeast cells to mating factor. The sequence of the BAR1 gene is known in the art (see e.g., U.S. Pat. No. 4,613,572). Moreover, the sequences required for α-factor-enhanced expression of the Bar1, and other pheromone responsive genes have been identified. (Appeltauer and Achstetter 1989. Eur. J. Biochem., 181:243; Hagen et al. 1991, Mol. Cell. Biol. 11:2952). In an exemplary embodiment, the yeast Bar1 promoter can be engineered by mutagenesis to be more responsive, e.g., to more strongly promote gene transcription, upon stimulation of the yeast pheromone pathway. Standard techniques for mutagenizing the promoter can be used. In such embodiments, it is desirable that the conserved oligonucleotide motif described by Appeltaure et al. be conserved.

In yet other embodiments, rather than measuring second messenger production or alterations in transcription, the activity of endogenous yeast proteins can be assayed. For example, in one embodiment, the signal transduction pathway of the receptor upregulates expression or otherwise activates an enzyme which is capable of modifying a substrate which can be added to the cell. The signal can be detected by using a detectable substrate, in which case loss of the substrate signal is monitored, or alternatively, by using a substrate which produces a detectable product. In certain embodiments, the substrate is naturally occurring. Alternatively, the substrate can be non-naturally occurring. In preferred embodiments, BAR1 activity can be measured.

In other embodiments, the modulation of a receptor by a test compound can result in a change in the transcription of a gene, which is not normally pheromone responsive. In preferred embodiments, the gene is easily detectable. For example, in a preferred embodiment, the subject assay can be used to measure Pho5, a secreted acid phosphatase. Acid phosphatase activity can be measured using standard techniques.

In other embodiments, reporter gene constructs can be used. Reporter gene constructs are prepared by operatively linking a reporter gene with at least one transcriptional regulatory element. If only one transcriptional regulatory element is included it must be a regulatable promoter. At least one of the selected transcriptional regulatory elements must be indirectly or directly regulated by the activity of the selected cell-surface receptor whereby activity of the receptor can be monitored via transcription of the reporter genes.

Many reporter genes and transcriptional regulatory elements are known to those of skill in the art and others may be identified or synthesized by methods known to those of skill in the art. Reporter genes include any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368) and green fluorescent protein (U.S. Pat. No. 5,491,084; WO96/23898).

Transcriptional control elements include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos. Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Other promoters and transcriptional control elements, in addition to those described above, include the vasoactive intestinal peptide (VIP) gene promoter (cAMP responsive; Fink et al. (1988), Proc. Natl. Acad. Sci. 85:6662–6666); the somatostatin gene promoter (cAMP responsive; Montminy et al. (1986), Proc. Natl. Acad. Sci. 8.3:6682–6686); the proenkephalin promoter (responsive to cAMP, nicotinic agonists, and phorbol esters; Comb et al. (1986), Nature 323:353–356); the phosphoenolpyruvate carboxy-kinase gene promoter (cAMP responsive; Short et al. (1986), J. Biol. Chem. 261:9721–9726); the NGFI-A gene promoter (responsive to NGF, cAMP, and serum; Changelian et al. (1989). Proc. Natl. Acad. Sci. 86:377–381); and others that may be known to or prepared by those of skill in the art.

In certain assays it may be desirable to use changes in growth in the screening procedure. For example, one of the consequences of activation of the pheromone signal pathway in wild-type yeast is growth arrest. If one is testing for an antagonist of a G protein-coupled receptor, this normal response of growth arrest can be used to select cells in which the pheromone response pathway is inhibited. That is, cells exposed to both a known agonist and a peptide of unknown activity will be growth arrested if the peptide is neutral or an agonist, but will grow normally if the peptide is an antagonist. Thus, the growth arrest response can be used to advantage to discover peptides that function as antagonists.

However, when searching for compounds which can function as modulators of pheromone response pathways, the growth arrest consequent to activation of the pheromone response pathway is an undesirable effect since cells that bind agonists stop growing while surrounding cells that fail to bind agonists will continue to grow. The cells of interest, then, will be overgrown or their detection obscured by the background cells, confounding identification of the cells of interest. To overcome this problem the present invention teaches engineering the cell such that: 1) growth arrest does not occur as a result of exogenous signal pathway activation (e.g., by inactivating the FAR1 gene); and/or 2) a selective growth advantage is conferred by activating the pathway (e.g., by transforming an auxotrophic mutant with a HIS3 gene under the control of a pheromone-responsive promoter, and applying selective conditions).

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA binding repressor protein, and incorporating a suitable operator site into the promoter or other suitable region of the marker gene.

In the case of yeast, exemplary positively selectable (beneficial) genes include the following: URA3, LYS2, HIS3, LEU2, TRP1; ADE1, 2, 3, 4, 5, 7, 8; ARG1, 3, 4, 5, 6, 8; HIS1, 4, 5; ILV1, 2, 5; THR1, 4; TRP2, 3, 4, 5; LEU1, 4; MET2, 3, 4, 8, 9, 14, 16, 19; URA1, 2, 4, 5, 10; HOM3, 6; ASP3; CHO1; ARO 2,7; CYS3; OLE1; INO1, 2, 4; PRO1, 3. Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In another embodiment a reporter gene, e.g., the fus1-lacZ reporter plasmid can be introduced along with the AGS. The addition of an antagonist should result in a decrease in β-galactosidase units over that observed in the absence of the antagonist, demonstrating the ability of the antagonist to interact in a negative fashion with the AGS.

In another version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

In appropriate assays, so-called counterselectable or negatively selectable genes may be used. Suitable genes include: URA3 (orotidine-5'-phosphate decarboxylase; inhibits growth on 5-fluoroorotic acid), LYS2 (2-aminoadipate reductase; inhibits growth on α-aminoadipate as sole nitrogen source), CYH2 (encodes ribosomal protein L29; cycloheximide-sensitive allele is dominant to resistant allele), CAN1 (encodes arginine permease; null allele confers resistance to the arginine analog canavanine), and other recessive drug-resistant markers. CAN1 is one example of a preferred reporter gene.

In one example, the reporter gene affects yeast cell growth. The natural response to signal transduction via the yeast pheromone system response pathway is for cells to undergo growth arrest. This is a preferred way to select for antagonists of a ligand/receptor pair that stimulates a the pathway. An antagonist would inhibit the activation of the pathway; hence, the cell would be able to grow. Thus, the FAR1 gene may be considered an endogenous counterselectable marker. The FAR1 gene is preferably inactivated when screening for agonist activity.

The reporter gene may also be a screenable gene. The screened characteristic may be a change in cell morphology, metabolism or other screenable features. Suitable markers include beta-galactosidase (Xgal, $C_{12}$FDG, Salmon-gal, Magenta-Gal (latter two from Biosynth Ag)), alkaline phosphatase, horseradish peroxidase, exo-glucanase (product of yeast exbl gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate Xgal into a blue pigment. Again, the promoter may be receptor-induced or receptor-inhibited.

In another example using yeast cells, a screen can take advantage of the fact that a gpa1 fus1-HIS3 colony expressing wild type Gαs can grow upon replica plating to media lacking histidine and containing 1 mM 3-aminotriazole (AT). The growth of this strain occurs due to the partially constitutive state of the pheromone pathway, which leads to partial derepression of the fus1-HIS3 reporter gene. AT inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. A colony to which an antagonist of an AGS has been added will presumably fail to grow on this media due to the reduced signaling via the pheromone pathway.

In certain embodiments, a peptide library can be expressed to test for modulators of an AGS. In one embodiment, the peptide library is expressed by the cell that also expresses the AGS, thereby creating an "autocrine" system, wherein the peptide to be tested for AGS-modulating activity is made by the same cell expressing the AGS protein. For a general description of yeast cell autocrine systems for screening peptide, see PCT Publication WO 94/23025 by Fowlkes et al., the contents of which are expressly incorporated herein by reference. In certain embodiments in which yeast cells are used, such a library can be expressed using a leader sequence for periplasmic expression, e.g., a yeast mating factor leader sequence. Yeast cells are bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the eriplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the α-factor prosequence and terminal tetrapeptide. Use of either of the described pathways is within the scope of the invention.

The present invention does not require periplasmic secretion of peptides, or, if such secretion is provided, any particular secretion signal or transport pathway. In certain embodiments, peptides expressed with a signal sequence may bind to and modulate AGS molecules prior to their transport to the cell surface.

In other embodiments, a heterologous G-protein coupled receptor can be coexpressed with a heterologous AGS protein. In embodiments in which yeast cells are used, it may be desirable to use the leader sequence of a yeast secreted protein to direct transport of G-protein coupled receptors to the plasma membrane.

In certain embodiments, the compounds to be tested in the subject assays can be derived from libraries. While the use of libraries of peptides is well established in the art, new techniques have been developed which have allowed the production of mixtures of other compounds, such as benzodiazepines (Bunin et al. 1992. J. Am. Chem. Soc. 114:10987; DeWitt et al. 1993. Proc. Natl. Acad. Sci. USA 90:6909) peptoids (Zuckermann. 1994. J. Med. Chem. 37:2678) oligocarbamates (Cho et al. 1993. Science. 261:1303), and hydantoins (DeWitt et al. supra). Rebek et al. have described an approach for the synthesis of molecular libraries of small organic molecules with a diversity of 104–105 (Carell et al. 1994. Angew. Chem. Int. Ed. Engl. 33:2059; Carell et al. Angew. Chem. Int. Ed. Engl. 1994. 33:2061).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. Anticancer Drug Des. 1997. 12:145).

In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. Proc. Natl. Acad. Sci. USA 91:11422; Horwell et al. 1996 Immunopharmacology 33:68; and in Gallop et al. 1994. J. Med. Chem. 37:1233. In addition, libraries such as those described in the commonly owned U.S. Pat. No. 6,037,340 can be used to provide compounds for testing in the present invention. The contents of each of these applications is expressly incorporated herein by this reference.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In certain embodiments, the test compounds are exogenously added to the yeast cells expressing a recombinant receptor and compounds that modulate signal transduction via the receptor are selected. In other embodiments, the yeast cells express the compounds to be tested. For example, a culture of the subject yeast cells can be further modified to collectively express a peptide library as described in more detail in PCT Publication WO 94/23025 the contents of which is expressly incorporated herein by this reference.

Other types of peptide libraries may also be expressed, see, for example, U.S. Pat. Nos. 5,270,181 and 5,292,646; and PCT publication WO94/02502). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

In certain other embodiments, cells can be engineered to produce the compounds to be tested. This assay system has the advantage of increasing the effective concentration of the compound to be tested. In one embodiment, a method such as that described in WO 94/23025 can be utilized.

Other methods can also be used. For example, peptide libraries are systems which simultaneously display, in a form which permits interaction with a target, a highly diverse and numerous collection of peptides. These peptides may be presented in solution (Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science*, 249:386–390); (Devlin (1990)Science, 249:404–406); (Cwirla et al. (1990) *Proc. Natl. Acad. Sci.* 87:6378–6382); (Felici (1991) *J. Mol. Biol.* 222:301–310); (Ladner supra.). Many of these systems are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. While a cell surface receptor may be used as a target, the screening will not reveal whether the binding of the peptide caused an allosteric change in the conformation of the receptor.

The Ladner et al. patent, U.S. Pat. No. 5,096,815, describes a method of identifying novel proteins or polypeptides with a desired DNA binding activity. Semi-random ("variegated") DNA encoding a large number of different potential binding proteins is introduced, in expressible form, into suitable yeast cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a receptor protein. Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., *J. Biol. Chem.* (1989) 264, 20206 and Kaiser et al. (1987) *Science*, 235:312, respectively).

In certain embodiments of the instant invention, the compounds tested are in the form of peptides from a peptide library. The peptide library of the present invention takes the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins (see, for example, U.S. Pat. Nos. 5,270,181 and 5,292,646; and PCT publication WO94/02502). The combinatorial peptide can be attached one the terminus of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3–100 amino acids in length, more preferably at least 5–50, and even more preferably at least 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In another embodiment, the peptide library is a combinatorial library of polypeptides which are based at least in part on a known polypeptide sequence or a portion thereof (not a cDNA library). That is, the sequences of the library is semi-random, being derived by combinatorial mutagenesis of a known sequence. See, for example, Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461. Accordingly, polypeptide(s) which are known ligands for a target receptor can be mutagenized by standard techniques to derive a variegated library of polypeptide sequences which can further be screened for agonists and/or antagonists.

In still another embodiment, the combinatorial polypeptides are produced from a cDNA library.

In a preferred embodiment of the present invention, the cells collectively produce a "peptide library", preferably including at least $10^3$ to $10^7$ different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In certain embodiments of the present invention, the peptides of the library are encoded by a mixture of DNA molecules of different sequence. Each peptide-encoding DNA molecule is ligated with a vector DNA molecule and the resulting recombinant DNA molecule is introduced into a yeast cell. Since it is a matter of chance which peptide encoding DNA molecule is introduced into a particular cell, it is not predictable which peptide that cell will produce. However, based on a knowledge of the manner in which the mixture was prepared, one may make certain statistical predictions about the mixture of peptides in the peptide library.

The peptides of the library can be composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

In the case of yeast cells, test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway.

This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the a-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention. The present invention does not require periplasmic secretion, or, if such secretion is provided, any particular secretion signal or transport pathway.

After identifying certain test compounds as potential modulators of AGS proteins, the practitioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The compounds selected in the subject assay, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985).

In yet another aspect of the invention, the AGS proteins can be used as "bait proteins" in a two-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with AGS ("AGS-binding proteins" or "AGS-bp") and modulate AGS protein activity. Such AGS-binding proteins are also likely to be involved in the propagation of signals by the AGS proteins as, for example, upstream or downstream elements of the pheromone response pathway.

The two-hybrid system is based on the modular nature of most transcription factors, which consist of separable DNA-binding and activation domains. Briefly, the assay utilizes two different DNA constructs. In one construct, ("bait"), the gene that codes for AGS, is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an AGS-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with AGS.

Another aspect of the invention is directed to a yeast-based counter-screen for pheromone pathway inhibitors. This screen is based on a yeast cell constitutively expressing a receptor-independent activator (e.g., AGS1) of the yeast pheromone response pathway such that a lethal marker gene is expressed (e.g., Can1). Then, a cDNA library of interest, cloned into an appropriate vector (e.g., pYES2), is introduced into this strain to identify cDNAs that, when expressed, counteract the activators ability to induce the expression of the lethal marker gene. This screen, therefore, can rapidly identify proteins that both directly and indirectly regulate activators of the pheromone response pathway.

Modulators of AGS protein activity and/or AGS nucleic acid expression identified according to these drug screening assays can be used to treat, for example, diseases or disorders characterized by excessive or insufficient G-protein mediated signal transduction. Examples of such diseases or disorders which can be treated using modulators of AGS protein activity and/or nucleic acid expression include proliferative disorders and/or diseases. Support for the use of AGS modulators in treating proliferative disorders can be found in the fact that, for example, oncogenic mutations in ras-like G proteins have been implicated in approximately 30% of human cancers, including 90% of pancreatic and 50% of colon cancers (Bos (1988) *Mutat. Res.* 195:255–271; Bos (1989) *Cancer Res.* 49:4682–4689). In addition, defects in GPCR-mediated signaling have been associated with various disease states (Landis et al. (1989) *Nature* 340:692–696 (pituitary tumors); Lyons et al. (1990) *Science* 249:655–659 (human endocrine tumors); Allen et al. (1991) *Proc. Natl. Acad. Sci. USA* 88:11354–11358 (neoplastic transformation and athlerosclerosis); and Farfel et al. (1996) *J. Biol. Chem.* 271:19653–19655 (pseudo-hypoparathyroidism)). As AGS is both a member of the ras family and an activator of heterotrimeric G-protein mediated signal transduction, modulators of AGS function are likely to have pharmaceutical applications. Methods of treatment include the steps of administering the AGS molecules of the present invention or modulators of AGS protein activity and/or nucleic acid expression, e.g., in a pharmaceutical composition as described above, to a subject in need of such treatment.

b) Detection and Diagnostic Assays

The invention further provides a method for detecting the presence of AGS in a biological sample. The method involves contacting the biological sample with a compound or an agent capable of detecting AGS protein or mRNA such that the presence of AGS is detected in the biological sample. A preferred agent for detecting AGS mRNA is a labeled or labelable nucleic acid probe capable of hybridizing to AGS mRNA. The nucleic acid probe can be, for example, the AGS cDNA of SEQ ID NO:1, or a portion thereof, such as an oligonucleotide of at least 15, 30, 50, 100, 250 or 500 nucleotides in length and sufficient to specifically hybridize under stringent conditions to AGS mRNA. A preferred agent for detecting AGS protein is a labeled or labelable antibody capable of binding to AGS protein. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (e.g., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect AGS mRNA or protein in a biological sample in vitro as well as in vivo. For example, in vitro techniques for detection of AGS mRNA include Northern hybridizations and in situ hybridizations. In vitro techniques for detection of AGS protein include enzyme linked immunosorbent assays (ELISAs), Western blots, immunoprecipitations and immunofluorescence. Alternatively, AGS protein can be detected in vivo in a subject by introducing into the subject a labeled anti-AGS antibody. For example, the antibody can be labeled with a radioactive marker whose presence and location in a subject can be detected by standard imaging techniques.

In one preferred embodiment of the detection method, the biological sample is a cell sample, a tissue section, for example, a freeze-dried or fresh frozen section of tissue removed from a patient, or a biological fluid obtained from a subject.

The invention also encompasses kits for detecting the presence of AGS in a biological sample. For example, the kit can comprise a labeled or labelable compound or agent capable of detecting AGS protein or mRNA in a biological sample; means for determining the amount of AGS in the sample; and means for comparing the amount of AGS in the sample with a standard. The compound or agent can be packaged in a suitable container. The kit can further comprise instructions for using the kit to detect AGS mRNA or protein.

c) Methods of Treatment

Additional methods of the invention include methods for treating a subject having a disorder characterized by aberrant AGS activity or expression. These methods include administering to the subject an AGS modulator such that treatment of the subject occurs. The terms "treating" or "treatment", as used herein, refer to reduction or alleviation of at least one adverse effect or symptom of a disease or disorder, e.g., a disease or disorder characterized by or associated with abnormal or aberrant AGS protein activity or AGS nucleic acid expression.

As used herein, an AGS modulator is a molecule which can modulate AGS nucleic acid expression and/or AGS protein activity. For example, an AGS modulator can modulate, e.g., upregulate (activate) or downregulate (suppress), AGS nucleic acid expression. In another example, an AGS modulator can modulate (e.g., stimulate or inhibit) AGS protein activity. If it is desirable to treat a disease or disorder characterized by (or associated with) aberrant or abnormal (non-wild-type) AGS nucleic acid expression and/or AGS protein activity by inhibiting AGS nucleic acid expression, an AGS modulator can be an antisense molecule, e.g., a ribozyme, as described herein. Examples of antisense molecules which can be used to inhibit AGS nucleic acid expression include antisense molecules which are complementary to a portion of the 5' untranslated region of SEQ ID NO:3, which also includes the start codon and antisense molecules which are complementary to a portion of the 3' untranslated region of SEQ ID NO:3. AN AGS modulator which inhibits AGS nucleic acid expression can also be a small molecule or other drug, e.g., a small molecule or drug identified using the screening assays described herein, which inhibits AGS nucleic acid expression. If it is desirable to treat a disease or disorder characterized by (or associated with) aberrant or abnormal (non-wild-type) AGS nucleic acid expression and/or AGS protein activity by stimulating AGS nucleic acid expression, an AGS modulator can be, for example, a nucleic acid molecule encoding AGS (e.g., a nucleic acid molecule comprising a nucleotide sequence homologous to the nucleotide sequence of SEQ ID NO:1) or a small molecule or other drug, e.g., a small molecule (peptide) or drug identified using the screening assays described herein, which stimulates AGS nucleic acid expression.

Alternatively, if it is desirable to treat a disease or disorder characterized by (or associated with) aberrant or abnormal (non-wild-type) AGS nucleic acid expression and/or AGS protein activity by inhibiting AGS protein activity, an AGS modulator can be an anti-AGS antibody or a small molecule or other drug, e.g., a small molecule or drug identified using the screening assays described herein, which inhibits AGS protein activity. If it is desirable to treat a disease or disorder characterized by (or associated with) aberrant or abnormal (non-wild-type) AGS nucleic acid expression and/or AGS protein activity by stimulating AGS protein activity, an AGS modulator can be an active AGS protein or portion thereof (e.g., an AGS protein or portion thereof having an amino acid sequence which is homologous to the amino acid sequence of SEQ ID NO:2) or a small molecule or other drug, e.g., a small molecule or drug identified using the screening assays described herein, which stimulates AGS protein activity.

In another embodiment, an AGS modulator is an indirect modulator (e.g., an indirect activator or inhibitor of AGS protein expression and/or activity. For example, it may be possible to modulate the expression of an AGS protein by targeting a transcription factor which activates or represses AGS gene transcription. Accordingly, an AGS modulator is an indirect modulator which increases the expression and/or activity of an AGS-specific transcription factor. In another embodiment, an AGS modulator is an indirect modulator which decreases the expression and/or activity of an AGS-specific transcription factor.

Other aspects of the invention pertain to methods for modulating a cell associated activity. These methods include contacting the cell with an agent (or a composition which includes an effective amount of an agent) which modulates AGS activity or AGS expression such that a cell associated activity is altered relative to a cell associated activity of the cell in the absence of the agent. As used herein, "a cell associated activity" refers to a normal or abnormal activity or function of a cell. Examples of cell associated activities include proliferation, migration, differentiation, production or secretion of molecules, such as proteins, and cell survival. In a preferred embodiment, the cell-associated activity is mediated by a G-protein signaling pathway. The term "altered" or "modulated" as used herein refers to a change, e.g., an increase or decrease, of a cell associated activity. In one embodiment, the agent stimulates AGS protein activity or AGS nucleic acid expression. Examples of such stimulatory agents include an active AGS protein, a nucleic acid molecule encoding AGS that has been introduced into the cell, and a modulatory agent which stimulates AGS protein activity or AGS nucleic acid expression and which is identified using the drug screening assays described herein. In another embodiment, the agent inhibits AGS protein activity or AGS nucleic acid expression. Examples of such inhibitory agents include an antisense AGS nucleic acid molecule, an anti-AGS antibody, and a modulatory agent which inhibits AGS protein activity or AGS nucleic acid expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, e.g., the cell is present within a subject, e.g., a mammal, e.g., a human, and the subject has a disorder or disease characterized by or associated with abnormal or aberrant AGS activity or expression.

A nucleic acid molecule, a protein, an AGS modulator etc. used in the methods of treatment can be incorporated into an appropriate pharmaceutical composition described herein and administered to the subject through a route which allows the molecule, protein, modulator etc. to perform its intended function. Examples of routes of administration are also described herein. Particular AGS inhibitory agents and AGS stimulatory agents are described further below.

Inhibitory Agents:

According to a modulatory method of the invention, AGS activity is inhibited in a cell by contacting the cell with an inhibitory agent. Inhibitory agents of the invention can be, for example, intracellular binding molecules that act to inhibit the expression or activity of AGS. As used herein, the term "intracellular binding molecule" is intended to include molecules that act intracellularly to inhibit the expression or activity of a protein by binding to the protein itself, to a nucleic acid (e.g., an mRNA molecule) that encodes the protein or to a target with which the protein indirectly interacts. Examples of intracellular binding molecules, described in further detail below, include polypeptides that directly or indirectly bind an AGS molecule or target molecule, antisense AGS nucleic acid molecules (e.g., to inhibit translation of AGS mRNA), intracellular anti-AGS antibodies (e.g., to inhibit the activity of AGS protein) and chemical inhibitors of the AGS protein.

In one embodiment, an inhibitor of an AGS or AGS-related molecule is identified by modifying one of the above-mentioned assays to activate a reporter gene that prevents growth (e.g., CAN1). Thus, candidate inhibitors of an AGS or AGS-related activator that can block the AGS induction of the growth inhibiting gene can be rapidly screened and identified (FIG. 2b). This variation of the above assay may used for either the screening of a nucleic acid library or a compound library. Accordingly, in one embodiment, an identified inhibitor of an AGS molecule is the RGS5 polypeptide (SEQ ID NO:25) which either directly or indirectly down-regulates AGS activity.

In another embodiment, an inhibitory agent of the invention is an antisense nucleic acid molecule that is complementary to a gene encoding AGS or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986; Askari, F. K. and McDonnell, W. M. (1996) N. Eng. J. Med. 334:316–318; Bennett, M. R. and Schwartz, S. M. (1995) Circulation 92:1981–1993; Mercola, D. and Cohen, J. S. (1995) Cancer Gene Ther. 2:47–59; Rossi, J. J. (1995) Br. Med. Bull. 51:217–225; Wagner, R. W. (1994) Nature 372:333–335) e.g. Preferably, an antisense nucleic acid is designed so as to be complementary to a region preceding or spanning the initiation codon on the coding strand or in the 3' untranslated region of an mRNA. An antisense nucleic acid for inhibiting the expression of AGS protein in a cell can be designed based upon the nucleotide sequence encoding the AGS protein (e.g., SEQ ID NO:1), constructed according to the rules of Watson and Crick base pairing (e.g., as described above in subsection I).

An antisense nucleic acid can exist in a variety of different forms. For example, the antisense nucleic acid can be an oligonucleotide that is complementary to only a portion of an AGS gene. An antisense oligonucleotides can be constructed using chemical synthesis procedures known in the art. e.g. To inhibit AGS expression in cells in culture, one or more antisense oligonucleotides can be added to cells in culture media, typically at about 200 µg oligonucleotide/ml.

Alternatively, an antisense nucleic acid can be produced biologically using an expression vector into which a nucleic acid has been subcloned in an antisense orientation (e.g., nucleic acid transcribed from the inserted nucleic acid will be of an antisense orientation to a target nucleic acid of interest). e.g.

In another embodiment, an antisense nucleic acid for use as an inhibitory agent is a ribozyme. Ribozymes are catalytic RNA molecules with ribonuclease activity which are capable of cleaving a single-stranded nucleic acid, such as an mRNA, to which they have a complementary region (for reviews on ribozymes see e.g., Ohkawa, J. et al. (1995) *J. Biochem.* 118:251–258; Sigurdsson, S. T. and Eckstein, F. (1995) *Trends Biotechnol.* 13:286–289; Rossi, J. J. (1995) *Trends Biotechnol.* 13:301–306; Kiehntopf, M. et al. (1995) *J. Mol. Med.* 73:65–71). A ribozyme having specificity for AGS mRNA can be designed based upon the nucleotide sequence of the AGS cDNA. For example, a derivative of a Tetrahymena L-19 IVS RNA can be constructed in which the base sequence of the active site is complementary to the base sequence to be cleaved in an AGS mRNA. See for example U.S. Pat. Nos. 4,987,071 and 5,116,742, both by Cech et al. Alternatively, AGS mRNA can be used to select a catalytic RNA having a specific ribonuclease activity from a pool of RNA molecules. See for example Bartel, D. and Szostak, J. W. (1993) *Science* 261: 1411–1418.

Another type of inhibitory agent that can be used to inhibit the expression and/or activity of AGS in a cell is an intracellular antibody specific for the AGS protein. The use of intracellular antibodies to inhibit protein function in a cell is known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Letters* 274:193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Bio/Technology* 12:396–399; Chen, S-Y. et al. (1994) *Human Gene Therapy* 5:595–601; Duan, L et al. (1994) *Proc. Natl. Acad. Sci. USA* 91:5075–5079; Chen, S-Y. et al. (1994) *Proc. Natl. Acad. Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204:666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of AGS activity according to the inhibitory methods of the invention, an intracellular antibody that specifically binds the AGS protein is expressed in the cytoplasm of the cell. To prepare an intracellular antibody expression vector, antibody light and heavy chain cDNAs encoding antibody chains specific for the target protein of interest, e.g., AGS, are isolated, typically from a hybridoma that secretes a monoclonal antibody specific for the AGS protein. Hybridomas secreting anti-AGS monoclonal antibodies, or recombinant anti-AGS monoclonal antibodies, can be prepared as described above. Once a monoclonal antibody specific for AGS protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition,* U.S. Department of Health and Human Services, NIH Publication No. 91-3242 and in the "Vbase" human germline sequence database.

Once obtained, the antibody light and heavy chain sequences are cloned into a recombinant expression vector using standard methods. To allow for cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser_3)$) and expressed as a single chain molecule. To inhibit AGS activity in a cell, the expression vector encoding the anti-AGS intracellular antibody is introduced into the cell by standard transfection methods, as discussed hereinbefore.

Other inhibitory agents that can be used to inhibit the activity of an AGS protein are chemical compounds that directly inhibit AGS activity or inhibit the interaction between AGS and target molecules. Such compounds can be identified using screening assays that select for such compounds, as described in detail above.

Stimulatory Agents:

According to a modulatory method of the invention, AGS activity is stimulated in a cell by contacting the cell with a stimulatory agent. Examples of such stimulatory agents include active AGS protein and nucleic acid molecules encoding AGS that are introduced into the cell to increase AGS activity in the cell. A preferred stimulatory agent is a nucleic acid molecule encoding an AGS protein, wherein the nucleic acid molecule is introduced into the cell in a form suitable for expression of the active AGS protein in the cell. To express an AGS protein in a cell, typically an AGS-encoding DNA is first introduced into a recombinant expression vector using standard molecular biology techniques, as described herein. AN AGS-encoding DNA can be obtained, for example, by amplification using the polymerase chain reaction (PCR), using primers based on the AGS nucleotide sequence. Following isolation or amplification of AGS-encoding DNA, the DNA fragment is introduced into an expression vector and transfected into target cells by standard methods, as described herein.

Other stimulatory agents that can be used to stimulate the activity of an AGS protein are chemical compounds that stimulate AGS activity in cells, such as compounds that directly stimulate AGS protein and compounds that promote the interaction between AGS and target molecules. Such compounds can be identified using screening assays that select for such compounds, as described in detail above.

The modulatory methods of the invention can be performed in vitro (e.g., by culturing the cell with the agent or by introducing the agent into cells in culture) or, alternatively, in vivo (e.g., by administering the agent to a subject or by introducing the agent into cells of a subject, such as by gene therapy). For practicing the modulatory method in vitro, cells can be obtained from a subject by standard methods and incubated (e.g., cultured) in vitro with a modulatory agent of the invention to modulate AGS activity in the cells. If desired, cells treated in vitro with a modulatory agent of the invention can be readministered to the subject. For administration to a subject, it may be preferable to first remove residual agents in the culture from the cells before administering them to the subject. For further discussion of ex vivo genetic modification of cells followed by readministration to a subject, see also U.S. Pat. No. 5,399,346 by W. F. Anderson et al.

For practicing the modulatory method in vivo in a subject, the modulatory agent can be administered to the subject such that AGS activity in cells of the subject is modulated. The term "subject" is intended to include living organisms in which an AGS-dependent cellular response can be elicited. Preferred subjects are mammals. Examples of subjects include humans, monkeys, dogs, cats, mice, rats, cows, horses, goats and sheep.

For stimulatory or inhibitory agents that comprise nucleic acids (including recombinant expression vectors encoding AGS protein, antisense RNA and intracellular antibodies), the agents can be introduced into cells of the subject using methods known in the art for introducing nucleic acid (e.g., DNA) into cells in vivo. Examples of such methods encompass both non-viral and viral methods, including:

Direct Injection: Naked DNA can be introduced into cells in vivo by directly injecting the DNA into the cells (see e.g., Acsadi et al. (1991) *Nature* 332:815–818; Wolff et al. (1990) *Science* 247:1465–1468). For example, a delivery apparatus (e.g., a "gene gun") for injecting DNA into cells in vivo can be used. Such an apparatus is commercially available (e.g., from BioRad).

Cationic Lipids: Naked DNA can be introduced into cells in vivo by complexing the DNA with cationic lipids or encapsulating the DNA in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan, J. J. et al. (1995) *Gene Therapy*, 2:38–49; San, H. et al. (1993) *Human Gene Therapy*, 4:781–788).

Receptor-Mediated DNA Uptake: Naked DNA can also be introduced into cells in vivo by complexing the DNA to a cation, such as polylysine, which is coupled to a ligand for cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122–2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482–6486), hepatocytes (Herz and Gerard (1993) Proc. Natl. Acad. Sci. USA 90:2812–2816) and muscle cells (Quantin et al. (1992) Proc. Natl. Acad. Sci. USA 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129) It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

In a preferred embodiment, a retroviral expression vector encoding AGS is used to express AGS protein in cells in vivo, to thereby stimulate AGS protein activity in vivo. Such retroviral vectors can be prepared according to standard methods known in the art (discussed further above).

A modulatory agent, such as a chemical compound, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described above.

This invention is further illustrated by the following examples which should not be construed as limiting.

EXAMPLES

The following experimental procedures were used in the Examples:

Plasmids and yeast strains: All DNA manipulations were done using standard recombinant DNA techniques (see e.g., Sambrook et al. (1989) *Molecular Cloning: A Laboratory Manual*, 2nd Ed., Cold Spring Harbor Laboratory, Cold Spring Harbor, N.Y.; and Ausubel et al. (1994) *Current Protocols in Molecular Biology*, John Wiley & Sons, NY); using commercially available enzymes (New England Biolabs, BRL, United States Biochemical Corporation). Transformations of bacterial strain DH10B were performed by electroporation at 1.8 kV in a GenePulser II (BioRad). Transformations of yeast were performed as described in Ito et al. (1983) *J. Bacteriol.* 153:163–168; and Elble, R. (1992) *Biotechniques* 13:18–19.

Yeast strains used in this study are listed below in Table 1.

| YEAST STRAIN | GENOTYPE |
| --- | --- |
| CY1316 | MATα gpa1Δ far1Δ tbt1-1 fuslp-HIS3 can1 ste14::trp1::LYS2 ste3Δ lys2 ura3 leu2 trp1 his3 |
| CY4600 | MATα gpa1Δ ste4Δ far1Δ tbt1-1 fuslp-HIS3 can1 ste14::trp1::LYS2 ste3Δ lys2 ura3 leu2 trp1 his3 |
| CY12444 | MATα gpa1Δ ste5Δ far1Δ tbt1-1 fuslp-HIS3 can1 ste14::trp1::LYS2 ste3Δ lys2 ura3 leu2 trp1 his3 |
| CY12970 | MATα gpa1Δ ste20Δ far1Δ fuslp-HIS3 can1 ste14::trp1::LYS2 ste3Δ lys2 ura3 leu2 trp1 his3 |
| CY1141 | MATα GPA1$_{(1-41)}$-Gαi2 far1Δ tbt1-1 fuslp-HIS3 can1 ste14::trp1::LYS2 ste3Δ lys2 ura3 leu2 trp1 his3 |
| CY7967 | MATα GPA1$_{(1-41)}$-Gαi3 far1Δ tbt-1 fuslp-HIS3 can1 ste14::trp1::LYS2 ste3Δ lys2 ura3 leu2 trp1 his3 |
| CY8342 | MATα [rat Gαs] far1Δ tbt1-1 fuslp-HIS3 can1 ste14::trp1::LYS2 ste3Δ lys2 ura3 leu2 trp1 his3 |
| CY9603 | MATα GPA1$_{(1-41)}$-Gα16 far1Δ tbt-1 fuslp-HIS3 can1 ste14::trp1::LYS2 ste3Δ lys2 ura3 leu2 trp1 his3 |
| CY9571 | MATα GPA1 far1Δ tbt1-1 fuslp-HIS3 can1 ste14::trp1::LYS2 ste3Δ lys2 ura3 leu2 trp1 his3 |

CY1316 (MATα gpa1Δ farΔ tbt1-1 fus1-HIS3 can1 ste14::trp1::LYS2 ste3Δ lys2 ura3 leu2 trp1 his3): The parent of all strains used in this study, was obtained by standard genetic techniques, with SY1390 (Stevenson et al. (1992) Genes Dev. 6:1293–1304) (provided by G. Sprague), and SM1188 (Sapperstein et al. (1994) Mol. Cell. Biol. 14:1438–1449) (provided by S. Michaelis) serving as the original sources of the fus1-HIS3 and ste14 alleles, respectively. Unless otherwise indicated, all genomic disruptions were made with the URA3 gene, followed by selection on 5'-fluoroorotic acid (Boeke et al. (1987) Methods. Enz. 154:164–195). Gα genomic integrations were made at the GPA1 locus and verified by Southern, Gα expression, and phenotypic analysis. Plasmid pR15 (Beals et al. (1987) Proc. Natl. Acad. Sci. USA 84:7886–7890), carrying the coding region of human Gαi2. Plasmid CP1127, carrying the promoter sequences and first 41 amino acid codons of GPA1, was prepared by ligation of a sequence encompassing nucleotides −200 to +100 of GPA1 (where translational start is +1) to pRS405 (Sikorski and Hieter (1989) Genetics 122:19). Plasmid CP1183, carrying the GPA1$_{(1-41)}$-Gαi2 chimera sequence, was made by PCR amplification of the Gαi2 coding region encompassing amino acids 36 to its stop codon at position 357 using the oligo pair SEQ ID NO: 118 and SEQ ID NO:5 and using plasmid pR15 as template. The amplified product was digested with SacI and SalI, then ligated into SacI/SalI digested CP1127. A glycine to alanine alteration at codon 204 of Gαi2 in CP1183 was introduced using Stratagene's QuickChange kit and mutagenic oligos SEQ ID NO:6 and SEQ ID NO:7 creating plasmid CP5533. Sequences encoding β-galactosidase (lacZ) were introduced downstream of the fus1 promoter on plasmid pRS424 (Sikorski and Hieter (1989) Genetics 122:19) to create CP1584. Plasmid pSM187, with a 4.3 kb DNA fragment carrying the STE14 gene flanked by BamHI sites, was kindly provided by S. Michaelis. This BamHI fragment was inserted into BamHI digested and shrimp alkaline phosphatase treated pRS415 and pRS414 (Sikorski and Hieter (1989) Genetics 122:19) to create, respectively, plasmids CP5108 and CP5336.

The yeast phosphoglycerate kinase (PGK1) promoter sequence was amplified from yeast genomic DNA using the oligonucleotide pair set forth in SEQ ID NO:26 and SEQ ID NO:27, digested with BglII and NcoI, and ligated into Esp3I/NcoI digested Yep51Nco (Broach et al. (1983) In Experimental Manipulation of Gene Expression (M. Inouye, ed.) Academic Press, N.Y.). A 0.95 kb fragment encompassing this promoter was then excised with BglII and BamHI for ligation into pRS415 and pRS424 (Sikorski and Hieter (1989) Genetics 122:19). The coding sequence for human RGS4 was amplified by reverse-transcriptase PCR from human brain poly-A selected RNA and ligated downstream of the PGK1 promoter in pRS424. RGS4 sequences were then amplified by PCR using the oligonucleotide pair SEQ ID NO:28 and SEQ ID NO:29, digested with BamHI and XhoI, and ligated into BamHI/XhoI digested pYES2 (Invitrogen). FUS1 promoter sequences were amplified from yeast genomic DNA using the oligonucleotide pair SEQ ID NO:30 and SEQ ID NO:31, digested with KpnI and SalI, and gel purified. The CAN1 coding region was amplified from yeast genomic DNA using the oligonucleotide pair SEQ ID NO:32 and SEQ ID NO:33, digested with XhoI and PstI, and gel purified. Both purified fragments were ligated to PstI/KpnI digested pRS414 (Sikorski et al. (1989) Genetics 122:19–27) to create plasmid 2440. The coding sequence for human AGS1 (see below) was amplified by PCR using the oligonucleotide pair SEQ ID NO:34 and SEQ ID NO:35, digested with BspHI and SalI, and ligated into a NcoI/SalI digested derivative of pRS415 carrying the PGK1 promoter, creating plasmid 1451-AGS1. The Stratagene QuikChange kit and protocol were used to introduce a glycine to valine alteration at codon 31 of AGS1 in pYES2 using the mutagenic oligonucleotides of SEQ ID NOS: 36 and 37, as well as a cysteine to serine alteration at codon 278 of AGS1 using the mutagenic oligonucleotides of SEQ ID NOS: 38 and 39.

A customized adult human liver cDNA library, ligated into the yeast vector pYES2 at BstXI and EcoRI, was constructed by Invitrogen. This library was size selected at 1250 bp and contains approximately 1.77×10$^7$ primary recombinants.

The vector pYEX4Ti, which allows for copper inducible expression in yeast of sequences fused at the N-terminus with GST, was purchased from Amrad Biotech. Vector pGEX-KG, which allows for IPTG inducible expression in bacteria of sequences fused at the N-terminus with GST (Guan and Dixon (1991), Anal. Biochem. 192, 262–267). Similar vectors are also commercially available. The vectors pcDNA3.1HisC and pBlueBacHis2A, which allow for expression of N-terminal hexahistidine fusion proteins, were purchased from Invitrogen. The vector pIND which allows for inducible expression from mammalian cells, was purchased from Invitrogen. The cDNA for gene AGS was amplified from pYES2-AGS by PCR using the oligo pair provided in SEQ ID NOS: 8 and 9, cleaved with BamHI and EcoRI, and ligated into BamHI/EcoRI digested pYEX4Ti, pGEX-KG, pcDNA3.1HisC, pBlueBacHis2A and pIND. The coding sequence for Cdc42 was amplified by PCR from yeast genomic DNA using the oligo pair provided in SEQ ID NOS: 10 and 11, cleaved with BamHI and EcoRI, and ligated into BamHI/EcoRI digested PGEX-KG. Single glycine to valine alterations at codons 31 and 36, and a glycine to alanine alteration at codon 81, were constructed using the Stratagene QuickChange kit and protocol and the respective mutagenic oligo pairs provided in SEQ ID NO:12, and SEQ ID NO:13; SEQ ID NO:14, and SEQ ID NO:15, and SEQ ID NO:16 and SEQ ID NO:17.

Additional amino acid substitutions, using appropriately designed oligonucleotides and standard techniques, were also introduced into AGS1 at the following residue positions (in brackets): serine to glycine (33); serine to alanine (80); asparagine to glycine (82); phenylalanine to asparagine (44); serine to glycine (33) and serine to alanine (80); serine to glycine (33) and asparagine to glycine (82); serine to alanine (80) and asparagine to glycine (82); serine to glycine (33), serine to alanine (80), and asparagine to glycine (82); serine to glycine (33), serine to alanine (80), asparagine to glycine (82), and glycine to alanine (81); lysine to glutamic acid (225) and lysine to glutamic acid (226); and, cysteine to serine (278). The plasmid pcDNA3.1HisC-AGS served as a template for mutagenesis. Following mutagenesis, AGS sequences were excised with BamHI and EcoRI for subcloning into vectors described above. BamHI and EcoRI sites were introduced via PCR, for example the BamHI site was introduced using the primer set forth as SEQ ID NO:8 and the EcoRI site, introduced using the primer set forth as SEQ ID NO:9. Automated dideoxy sequencing was used to verify the correct construction of all plasmids used in the examples.

Yeast screens: All yeast strains were grown in synthetic medium (0.67% yeast nitrogen base without amino acids supplemented with amino acids, adenine, uracil and 2% carbon source as indicated). For the activator screens, cultures of CY1316/CP1183 were grown in glucose-supplemented medium lacking tryptophan to a cell density of approximately 2×10$^7$/ml prior to transformation with lithium acetate. Approximately 20 μg of an adult human liver cDNA library in vector pYES2 was used to transform 1×10$^9$ cells. Transformation mixtures were plated onto sucrose medium lacking tryptophan and uracil and grown at 30° for 20–22 hours. Replicas of each plate were then made onto galactose medium lacking tryptophan, uracil and histidine, and containing 1 mM AT. Replica plates were incubated at 30° for 72 hr and growing colonies patched onto sucrose plates lacking tryptophan and uracil for recovery. Cells from each patch were resuspended in sterile water and equal numbers of cells (approximately 2,000) were spotted onto 3 plates: sucrose medium lacking tryptophan and uracil; glucose medium lacking tryptophan, uracil and histidine and containing 1 mM AT; and galactose medium lacking tryptophan, uracil and histidine and containing 1 mM AT. Plates were grown at 300 for 48 hours. Isolates with a galactose-dependent growth phenotype were cultured in liquid glucose medium lacking tryptophan and uracil for plasmid recovery.

For the inhibitor screen, initial transformations of CY1141/2440/1451-AGS1 were performed as described above for the activator screen. Replicas of each plate were made onto selective galactose medium lacking uracil and arginine and containing 200 µg/ml canavanine. Replica plates were incubated at 30° C. for 72 hours and growing colonies patched onto selective sucrose plates lacking uracil for recovery. Cells from each patch were resuspended in sterile water and spotted as described above onto selective sucrose medium lacking uracil, and onto selective glucose or galactose medium lacking uracil and arginine and containing 200 µg/ml canavanine. Plates were grown at 30° for 24 hours then replica-plated onto identical medium and allowed to grow for an additional 24 hours to distinguish differential growth on galactose. Isolates with a galactose-dependent growth phenotype were cultured in liquid glucose medium lacking uracil for plasmid recovery. Strains CY1141/1451/2440 and CY1141/1451-AGS1/2440 were analyzed in a similar fashion on selective glucose medium lacking histidine and containing 2 mM AT or on selective glucose medium lacking arginine and containing 200 µg/ml canavanine.

Plasmids were isolated from yeast essentially as described in Strathern and Higgins (1991) *Methods Enz.* 194:319–329, except for the omission of the affinity purification step, and transformed by electroporation into DH10B for amplification and re-transformation into yeast. Isolated plasmids were digested with BstXI and EcoRI and electrophoresed on 1% agarose gels for analysis of insert size. Fresh cultures of yeast strains CY1316/CP1183 or CY1141/2440/1451-AGS1 were transformed with each isolated plasmid, plated onto sucrose medium lacking tryptophan and uracil, and grown at 30° for 20–22 hours. Replica plating and spotting assays were then performed as described above to identify plasmids that conferred a galactose-dependent growth phenotype on all transformants. Sequence of inserts was determined by automated dideoxy sequencing using primers homologous to pYES2 vector sequences in the T7 promoter region and the CYC1 terminator region, as well as primers internal to the insert sequence.

Epistasis tests: Epistasis analysis on yeast strains was performed by introducing the pYES2 vector alone or AGS carried on the pYES2 vector into the indicated strains. Strains were grown to saturation in liquid sensitive sucrose medium. Approximately 2000 cells from each transformant were spotted onto selective sucrose medium (to determine viability) and selective glucose and galactose medium lacking histidine and containing 1 mM AT. Plates were incubated at 30° for 2 days prior to photographing.

β-galactosidase assays: Indicated yeast strains carrying a plasmid-borne FUS1-lacZ reporter construct were grown for 16–18 hours in selective glucose or galactose medium. Cells were harvested in log phase. Aliquots of cells (100 µl) were placed in 96-well microtiter plates and 20 µl of 6×CPRG-Z buffer (360 mM $Na_2HPO_4$, 240 mM $NaH_2PO_4$, 60 mM KCl, 6 mM $MgSO_4$, 2.5% Triton X-100, 16 µl/ml β-mercaptoethanol, 10 mM (chlorophenol red-β-D-galactopyranoside (CPRG) was added. Plates were incubated at 37° C. and reactions stopped with 60 µl 1M sodium carbonate. Plates were read at 575 nm (using a Beckman Biomek® plate reader) and lacZ activity determined using the equation $1000 \times A_{575}/$(incubation time in min) ($OD_{600}$ of original culture. All assays were done in triplicate on three independent isolates of each strain, and average activity±SEM was calculated. Data were analyzed using GraphPad Prism® software (Version 2.01).

Sequence Alignments: Sequence alignments were performed using the CLUSTAL X multiple sequence alignment program (Version 1.0). CLUSTAL X is a windows-based version of CLUSTAL V (Higgins et al. (1991) *CABIOS* 8:189–191), modified as described in Thompson et al. (1994) *Nuc. Acids Res.* 22:4673–4680. Alternatively, polynucleotide alignments were performed using BLASTN (version 2.0.8 using the following parameters: match, 1; mismatch, -2; gap open, 5; gap extension, 2; x_dropoff, 50; expect, 10.0; wordsize, 11; and, filter, on. When aligning polypeptide sequence, BLASTP was employed using the following parameters: matrix, O BLOSUM 62; gap open, 11; gap extension, 1; x dropoff, 50; expect, 10.0; wordsize, 3; and, filter, on.

Analysis of tissue-specific expression of AGS: The full length coding sequence of AGS was generated by digestion of pYEX4Ti-AGS with BamHI and EcoRI, followed by two rounds of agarose gel purification (Qiagen). This fragment was radiolabelled with α-[$^{32}$P]-deoxycytidine triphosphate using the redi-prime kit and protocol (Amersham). Radiolabelled DNA was purified over a Sephadex G-50 spin column (Boehringer Mannheim). The radiolabelled fragment ($1.46 \times 10^9$ cpm/µg) was hybridized in a volume of 20 ml ($1.2 \times 10^6$ cpm/ml) to Multiple Tissue Northern Blots from human tissues and human cancer cell lines (Clontech #7750-1, #7757-1, #7760-1, #7754-1, and #7765-1) and to a Human RNA Master Blot (Clontech #7770-1) using the protocols provided by Clontech. Filters were exposed to Fuji X-ray film at −80° C. with intensifying screens prior to development.

Cell transfections: HEK293 cells were grown in Dulbecco's minimal essential medium (DMEM), supplemented with 10% fetal bovine serum and 1×penicillin/streptomycin, at 37° C. in a humidified atmosphere containing 5% $CO_2$. Cells were fed every two days and split at least once per week.

One day prior to transfection, cells were seeded at a density of $8 \times 10^5$ per 100-mm dish. Cells were transfected with 10 µg of pcDNA3.1-HisC vector (Invitrogen, San Diego, Calif.) or pcDNA3.1-HisC-AGS using SuperFect transfection reagent (Qiagen, Santa Clarita, Calif.) and the protocol provided by the manufacturer. Transfected cells were selected for resistance to the antibiotic Neomycin (0.5 µg/ml). Selection was begun three days after transfection and continued for two weeks. Constitutive expression of AGS (from the CMV promoter in pcDNA3.1-HisC) was monitored in Neomycin resistant clones by RNA blot analysis using the full length cDNA coding sequence of AGS as probe (labeled with α-[$^{32}$P]-deoxycytidine triphosphate as described above).

Cultures of Spodoptera frugiperda (Sf9) were transfected with recombinant pBlueBacHisA-AGS. AGS-positive transfectants were screened for the production of β-galactosidase and AGS-positive phage were amplified according to the protocols provided by Invitrogen.

In vitro transcription/translation assay: Protein expression from the original pYES2-AGS isolate and the pcDNA3.1-HisC-AGS construct was determined by coupled in vitro transcription/translation reactions using the kit, protocol, and control plasmid from Clontech. Protein was labeled with $^{35}$S-methionine by standard techniques and final products electrophoresed on a 12% SDS-polyacrylamide gel. Following electrophoresis, protein was electroblotted onto a PVDF membrane; the blot was washed extensively with water, air dried, and exposed without screens to Fuji X-ray film for 24 hours at ambient temperature.

Analysis of AGS protein expression levels: Expression levels of AGS tagged at the N-terminus with either GST or the His$_6$ epitope were determined. For expression in *Saccharomyces cerevisiae* strain CY1141 and *E. coli* strain BL21, AGS was introduced with an N-terminal GST fusion under control of the copper-inducible cup1 promoter on plasmid pYEX4Ti-AGS (yeast) or an IPTG-inducible Ptac promoter on plasmid pGEX-KG-AGS (bacteria). Plasmid CP5336, carrying an episomal copy of STE14, was also introduced into the yeast strains. For copper induction, cells were grown at 30° C. to a density of 5×10$^6$ cells/ml and treated with 0.1 mM CuSO$_4$ for 6 hours. Cells were harvested at a density of 1–2×10$^7$/ml, and cell extracts were prepared by bead lysis in the presence of denaturation buffer (240 mM Tris-HCl, pH 6.8, 20% glycerol, 2% (w/v) SDS, 0.5M β-mercaptoethanol), followed by denaturation at 100° C. for 5 minutes. For IPTG induction, cells were grown at 30° C. in 2×YT supplemented with 100 μg/ml ampicillin to an initial optical density at 600 nm of 0.5, then treated with 0.5 mM IPTG for 3 hours. Cells were harvested by centrifugation and whole cell extracts prepared by denaturation at 100° C. for 5 minutes in denaturation buffer.

For transient expression in insect cells, recombinant phage carrying the pBlueBacHisA-AGS construct were used to infect cultures of Sf9 cells. 2–3 days post-infection, cells were harvested by centrifugation and whole cell extracts prepared by denaturation at 100° C. for 5 minutes in denaturation buffer. Stable transfectants of HEK293 cells carrying pcDNA3.1-HisC-AGS were cultured to ~80% confluency in DMEM and harvested by scraping in the presence of PBS. Cells were lysed at 4° C. in 5 mM Tris-HCl, pH 7.4, 5 mM EDTA, 5 mM EGTA containing a protease inhibitor cocktail (Boehringer Mannheim Complete™) by mechanical disruption using a glass Dounce tissue grinder (Wheaton, Millville, N.J.). Following a low-speed centrifugation (3000×g, 10 minutes, 4° C.) to remove unlysed cells, supernatants were centrifuged at 100,000×g, 30 minutes, 4° C. to separate membrane and soluble fractions. membrane pellets were resuspended by brief sonication in lysis buffer and protein fractions denatured at 100° C. for 5 minutes in denaturation buffer.

Proteins were electrophoresed on 11% SDS-polyacrylamide gels (Laemmli (1970) *Nature* 227:680–685) and electroblotted onto PVDF membranes. Membranes were blocked in 5% dry milk (w/v) in TBS-T and probed with either a 1:2000 dilution of antiserum raised against GST from *Schistosoma japonicum* (Sigma), a 1:2000 dilution of monoclonal anti-RGSHis$_6$ antiserum (Qiagen), a 1:2000 dilution of monoclonal anti-His C-terminal antiserum (Invitrogen), or a 1:5000 dilution of anti-Xpress antiserum (Invitrogen). Blots were washed extensively with TBS-T and probed with a 1:10000 dilution of horseradish peroxidase-conjugated donkey anti-rabbit or anti-mouse antiserum (Amersham) for 1 hour at 25° C. After washing with TBS-T, blots were developed using the chemiluminescent substrate and protocol from Pierce.

Preparing Membrane Fractions: For determining protein localization, membrane fractions from mammalian cells, (e.g., CHO-K1 transiently transfected (72 hours post-transfection) were scraped from 150 mm dishes, washed twice in PBS, and cell pellets lysed by 10–20 strokes of a Dounce homogenizer in 5 mM Tris, pH 7.4, 5 mM EDTA, 5 mM EGTA, protease inhibitor cocktail, at 4° C. Lysates were centrifuged at 100,000×g for 30 minutes at 4° C., supernatant fractions removed, and crude membrane pellets resuspended by Dounce homogenization in 50 mM Tris, pH 7.4, 0.6 mM EDTA, 5 mM MgCl$_2$, and protease inhibitors were added prior to immunoblot analysis.

Antisera Specific for AGS1: Polyclonal antisera specific for the AGS1 protein were raised in rabbit against the peptide sequence DTKSCLKNKTKENVD (SEQ. ID NO. 42) (amino acids 123 through 137 of AGS1) through Cocalico Biologicals®. These antisera were determined to recognize AGS1 protein expressed in bacteria and mammalian cells by standard immunoblot analysis.

Immunoblot Analysis: Yeast cell extracts, other cell extracts, and membrane fractions were immunoblotted using standard techniques and (the chemiluminescent substrate and protocol from Pierce.

Analysis of Gpa1$_{(1-4)}$-Gαi2 expression levels: Yeast strains CY1316/CP1183 and CY1316/CP5533 containing either pYES2 or pYES2-AGS were grown for 20 hours at 30° C. in medium containing 2% galactose and lacking tryptophan and uracil to a final OD$_{600}$ of approximately 1. Cells were harvested by centrifugation, washed once with H$_2$O, and lysed at 4° C. by mechanical disruption using 0.5 mm glass beads in 5 mM Tris-HCl, pH 7.4, 5 mM EDTA, 5 mM EGTA containing a protease inhibitor cocktail (Boehringer Mannheim Completem). Following a low-speed centrifugation (3000×g, 4° C., 10 minutes) to remove cell debris, samples were centrifuged at 100,000×g, 4° C., 30 minutes to pellet crude membrane. Membrane pellets were resuspended in lysis buffer by brief sonication and samples were denatured, electrophoresed on 11% SDS-polyacrylamide gels and analyzed by immunoblotting as described above. Antiserum specific for the C-terminal region of Gαi2 (DuPont NEN) was used at a dilution of 1:1000.

Purification of tagged AGS for biochemical analysis: GST-AGS and GST-Cdc42 were purified from IPTG-induced *E. coli* cells carrying pGEX-KG-AGS or pGEX-KG-CDC42 using standard techniques. GST, GST-AGS, and GST-Cdc42 were purified from copper-induced yeast cells carrying pYEX-4T1, pYEX-4T1-AGS, or pYEX-4T1-Cdc42.

Interaction assays: GST and an N-terminal GST fusion of AGS1 were expressed in yeast from the CUP1 promoter on plasmid pYEX-4T1 (Armad) and bound to glutathione sepharose matrix (Pharmacia). After extensive washing, aliquots of matrix with bound GST fusion proteins were mixed with 100 μl extracts from Sf9 cells expressing either His$_6$-Gαi2 or the Ste4/His$_6$-Ste18 dimer for 1 hour at 4° C. Extracts from His$_6$-Gαi2 expressing cells were preincubated with either 1 mM GDP or 1 mM GTPγS for 45 minutes at 25° C. prior to incubation with GST affinity matrices. Samples were washed extensively and bound protein eluted at 100° C. for 5 minutes in denaturation buffer. Equivalent amounts of eluted protein were analyzed by immunoblotting using a 1:5000 dilution of anti-Xpress antisera (Invitrogen; recognized His$_6$ fusion epitope) or a 1:1000 dilution of anti-Ste4 antisera. Bound antibody was detected by chemiluminescence (Pierce).

Kinase Assays: The p42/p44 MAP kinase assays were performed using the enzyme assay system (Amersham Life Science BIOTRAK® code RPN 84) essentially as according to the manufacturer. Briefly, cells (e.g., EcR-CHO-K1, obtained from Invitrogen) were transiently transfected with pIND/LacZ or pIND/AGS1 DNA constructs, EcR-3T3 (obtained from Invitrogen) cells transiently transfected with pIND/LacZ or pIND/AGS1 DNA constructs, or CHO-K1 cells stably expressing the human Nociceptin receptor (CADUS clone #14), were induced to produce LacZ or AGS1expression using with 5 µM Ponasterone A for 5 and 16 hours. Cells were either pretreated with Pertusis toxin (50 ng/ml for 18 hours.) and/or stimulated with serum (3%) or nociceptin (100 nM).

After stimulation cells were washed, lysed, exposed to Magnesium [$^{32}$P] ATP (in appropriate buffers), and incubated for 30 minutes at 37° C. Reactions were then stopped with a stop reagent (10 µl), centrifuge for 15 sec at 14,000×g, aliquoted (30 µl) on to binding paper, washed, and counts were recorded as a measure of kinase activity.

Biochemical Analysis of Purified GST-AGS1: AGS1 were induced from cells carrying, respectively, plasmid pYEX4T1 or pYEX4T1-AGS1 with 0.2 mM CuSO$_4$ at 30° C. for 6 hours. Induced cells were harvested by centrifugation, washed in PBS, and lysed by vortexing with glass beads (0.5 mm; Biospec) in lysis buffer (50 mM Tris-HCl, pH 7.6, 50 mM NaCl, 0.5% Triton X-100, 1 mM DTT, 5 mM MgSO$_4$, 1 µl/ml Antifoam A (Sigma®)). All buffers used were at 4° C. and contained protease inhibitors (Boehringer Mannheim Completem, EDTA-free). GST and GST lysates were centrifuged at 10,000×g at 4° C. for 15 minutes and supernatants mixed batch-wise on a rotating platform with glutathione sepharose (Pharmacia) for 2 hours at 4° C. Samples were washed with 20 column volumes 50 mM Tris-HCl, pH 7.6, 50 mM NaCl, 0.01% Thesit, 5 mM MgSO$_4$, and eluted with 3 column volumes 50 mM Tris-HCl, pH 8.8, 150 mM NaCl, 5 mM MgSO$_4$, 0.01% Thesit, 20 mM reduced glutathione. The His$_6$-Gαi2 and Ste4/His$_6$-Ste18 dimer were purified from infected Sf9 cells after lysis in 110 mM Tris, pH 8.0, 100 mM NaCl, 5 mM MgCl$_2$, 1 mM ethylene glycol-bis(β-aminoethyl ether)N,N,N',N'-tetraacetic acid (EGTA), 0.5% Triton-X100, 10 µM GDP by gentle rocking at 4° C. for 30 minutes, followed by centrifugation at 10,000 rpm for 10 minutes. Lysates were bound batch-wise to a nickel-agarose matrix (ProBond; Invitrogen®) for 1 hour at 4° C. Samples were washed sequentially with 10 column volumes lysis buffer, 10 column volumes low pH buffer (20 mM NaPO$_4$, pH 6.0, 500 mM NaCl, 5 mM MgCl$_2$, 10 µM GDP, 0.01% Thesit, 50 mM imidazole), 10 column volumes neutralization buffer (50 mM Tris-HCl, pH 7.0, 250 mM NaCl, 5 mM MgCl$_2$, 0.01% Thesit), and eluted with 3 column volumes neutralization buffer containing 300 mM imidazole.

All purified proteins were dialyzed against 50 mM Tris-HCl, pH 7.6, 150 mM NaCl, 5 mM MgSO$_4$, 0.01% Thesit, 1 mM DTT and quick-frozen in dry ice for storage. Protein purity was monitored by gel electrophoresis and immunoblotting as described herein. Gα protein concentration was determined by saturation binding with excess radiolabelled GTPαS; GST fusion protein concentrations were determined by a dye-binding assay (BioRad®).

Protein Association Assays: Purified Gαi2 and Gβγ (0.3 µM) were mixed with either purified GST or GST-AGS1 (1.5 µM) in 100 µl 50 mM Tris, pH 7.6, 150 mM NaCl, 5 mM MgCl$_2$, 0.6 mM EGTA, 0.01% Thesit for 45 minutes at 25° C. Gαi2 (at 7 µM) was allowed to equilibrate with 1 mM GDP or 1 mM guanosine 5'-O-(3-thiotriphosphate) (GTPαS) for 45 minutes at 25° C. prior to dilution into assay mixtures. Following association, 50 µl of a 1:3 slurry of glutathione sepharose beads in association buffer was added to each sample, and samples were mixed gently at 4° C. for 60 minutes. Beads were washed batch-wise with 5×500 µl association buffer and bound protein eluted at 100° C. for 5 minutes in 125 µl denaturation buffer (240 mM Tris-HCl, pH 6.8, 20% glycerol, 2% (w/v) SDS, 0.5 M β-mercaptoethanol). Proteins were electrophoresed on 12% sodium dodecyl sulfate-polyacrylamide gels and electroblotted onto polyvinylidene difluoride membranes. GST proteins were measured by staining membranes with 0.2% amido black. Membranes were blocked in 5% dry milk (w/v) in Tris-buffered saline, 0.1% Tween-20 (TBS-T) and probed with either a 1:5,000 dilution of anti-Xpress antisera (Invitrogen®) or a 1:2,000 dilution of anti-Ste4 antisera for 2 hours at 25° C. Blots were washed extensively with TBS-T and probed with a 1:10,000 dilution of horseradish peroxidase-conjugated donkey anti-mouse or anti-rabbit antiserum (Amersham®) for 1 hour at 25° C. After washing with TBS-T, blots were developed using the chemiluminescent substrate from Pierce® according to the manufacturers protocol.

GTPαS Binding Assays: A 6 pmol amount of purified His$_6$-Gαi2 or myristoylated Gαi1 was incubated for 30 minutes at 25° C. either alone or with 170 pmol GST or GST-AGS1 in the presence of 1.4 nmol GDP in a total volume of 280 µl assay buffer (50 mM Tris-HCl, pH 7.5, 150 mM NaCl, 0.6 M ethylenediaminetetraacetic acid, 5 mM MgCl$_2$, 0.01% Thesit).

A 28 pmol amount of GTPγ$^{35}$S (1.3×10$^6$ cpm/pmol) in 70 µl assay buffer was then added and 50 µl aliquots removed at the indicated times for filtration onto nitrocellulose membranes. Filters were washed with 2×2 ml ice-cold 20 mM Tris-HCl, pH 8.0, 100 mM NaCl, 25 mM MgCl$_2$, air-dried, and bound counts determined in the presence of scintillation fluid.

GTPase Activity Assays: Purified GST and GST-AGS1 or GST-Cdc42 (yeast) at 500 nM were incubated in 50 mM Tris, pH 7.4, 150 mM NaCl, 5 mM MgCl$_2$, 1 mM DTT, 0.01% Thesit with 5 µM γ[$^{32}$p]-GTP at 25° C. At the indicated times, 50 µl aliquots were removed into 750 µl of an ice-cold suspension of 5% charcoal (Norit®) in 50 mM NaH$_2$PO$_4$. Samples were vortexed, centrifuged, and 400 µl aliquots of supernatants removed for scintillation counting.

Guanine Nucleotide Binding Assays: Cultures of CY1316 (Δgpa1) and CY4600 (Δgpa1Δste4) carrying pYEX4T1, pYEX4T1-AGS1 or pYEX4T1-CDC42 were grown in low phosphate medium (10 µM), and GST fusion proteins induced by the addition of 200 µM CuSO$_4$. 30 minutes after copper addition, acid-free [$^{32}$P]-PO$_4$ was also added (50 µCi/ml). Cells were grown an additional 5 hours, harvested, washed with cold water, and pellets quick frozen on dry ice. Thawed pellets were lysed by vortexing with beads in 50 mM Tris, pH 7.4, 20 mM MgCl$_2$, 50 mM NaCl, 0.5% Triton X-100, 1 mM DTT, protease and phosphatase inhibitors. Samples were centrifuged 10 minutes at 10000 rpm and supernatants bound to 150 µl glutathione sepharose for 2 hours at 4° C. Columns were washed extensively in 50 mM Tris, pH 7.4, 20 mM MgCl$_2$, 50 mM NaCl, 0.1% Triton X-100 and bound material eluted by heating to 70° C. in 50 mM Tris, pH 8.8, 20 mM reduced glutathione, 150 mM NaCl, 2% SDS, 20 mM EDTA, 2 mM GDP, 2 mM GTP. Eluted GST fusion proteins were quantitated by SDS-PAGE followed by staining gels in Coomassie blue, and equivalent amounts of GST fusion proteins were spotted onto PEI-cellulose plates. After allowing samples to dry, plates were washed extensively with ddH$_2$O followed by methanol, dried and developed in 1 M KH$_2$PO$_4$, pH 3.4. Dried plates were exposed to X-ray film for analysis.

Abbreviations used herein are as follows: GPCR, G-protein coupled receptor; PAK, p-21 activated protein kinase; MAP kinase, mitogen activated protein kinase; RGS, regulator of G protein signaling; PCR, polymerase chain reaction; IGP, imidazoleglycerolphosphate; AT, 2-aminotriazole; SDS, sodium dodecyl sulfate; PVDF, polyvinylidene difluoride; GST, glutathione-S-transferase; TBS-T, Tris-buffered saline containing 0.1% Tween-20; DTT, dithiothreitol; GTPαS, guanosine-5'-o-(3-thiotriphosphate); CPRG, chlorophenolred-β-D-galactopyranoside; and IPTG, isopropyl β-D-thiogalactopyranoside.

Example 1

Yeast Host Strain for cDNA Library Screening

Upon activation of the pheromone response pathway, *Saccharomyces cerevisiae* normally undergoes Far1-mediated growth arrest (Chang and Herskowitz (1990) *Cell* 63:999–1011; Peter and Herskowitz (1994) *Science* 265:1228–1231). Deletion of the FAR1 gene uncouples growth arrest from pheromone-induced transcriptional activation (Chang and Herskowitz (1990) *Cell* 63:999–1011). By fusing promoter sequences from the pheromone-inducible gene FUS1 to the coding sequences of HIS3, expression of IGP dehydratase (encoded by the HIS3 gene) can be regulated by activation of the pheromone response pathway (Price et al. (1995) *Mol. Cell. Biol.* 15:6188–6195). Indeed, this regulated construct has proven useful in the identification of yeast mutants with constitutive pheromone pathway activation in the absence of a functional heterotrimer (Stevenson et al. (1992) *Genes Dev.* 6:1293–1304; Stevenson et al. (1995) *Genes Dev.* 9:2949–2963). Therefore, a his3 strain carrying the fus1-HIS3 construct can be made conditional for growth upon pheromone pathway activation by culturing this strain in medium lacking histidine. In a similar fashion, fus1 promoter sequences can be fused to β-galactosidase gene (lacZ) sequences, and pheromone pathway activation quantitated by calorimetric assays. In practice, the fus1 promoter activity of these constructs is often not entirely repressed in the absence of pheromone pathway activation (King et al. (1990) *Science* 250:121–123). To counteract this in strains carrying the fus1-HIS3 reporter, low levels of AT can be added to the culture medium to fully repress HIS3 activity (Manfredi et al. (1996) *Mol. Cell. Biol.* 16:4700–4709).

In searching for non-receptor modulators of the pheromone response pathway that act independently of GPCRs, a yeast strain lacking its native GPCR, Ste3, and its native heterotrimeric Gα subunit, Gpa1 (CY1316; see Table 1) was utilized. We introduced into this strain plasmid CP1183, encoding a chimeric Gα construct containing the first 41 amino acids of Gpa1 fused to amino acids 36–356 of human Gαi2. This chimeric construct is capable of functionally coupling to the yeast Gβγ dimer, allowing for full growth repression in the presence of 1 mM AT.

Example 2

Screening of a Human Liver cDNA Library for Pheromone Response Pathway Activators In validating the pheromone pathway activator screen a cDNA library derived from adult human liver was chosen. The human liver library was chosen as a potential general source of regulators. This cDNA library was ligated into the high-copy 2µ-based yeast vector pYES2. Sequences were ligated downstream of the yeast GAL1 promoter, making expression of cDNAs conditional upon the addition of galactose to the growth medium. The combination of a high-copy number vector and a strong galactose-inducible promoter increases the ability to detect even weak activators of the pheromone response pathway. A schematic of the pathway and yeast screen is shown respectively in FIGS. 1 and 2.

Yeast strain CY1316/1183 was transformed with each of the libraries and transformation mixtures plated on a series of agar plates containing sucrose to select for primary transformants. Sucrose was used as a carbon source rather than glucose, as glucose actively represses the GAL1 promoter (Schneider et al. (1991) *Meth. Enz.* 194:373–388). After allowing growth of primary transformants at 30° C. for 22 hours, replica plates were made onto galactose medium lacking histidine and containing 1 mM AT. Colonies appeared after approximately 2–3 d when grown at 30° C. Those transformants unable to produce HIS3 still must deplete their intracellular stores of histidine prior to the onset of cell stasis, leading to background growth on the replica plates. By replica plating transformants before visible colonies have formed background growth is kept minimal, allowing for clearer selection of colonies that are true histidine prototrophs. If necessary, a second replica plating to identical selective medium can be performed to distinguish true histidine prototrophs from those colonies exhibiting delayed cell inviability.

Growing colonies were recovered onto fresh sucrose plates containing histidine, and tested in a secondary screen on both glucose and galactose plates lacking histidine and containing 1 mM AT to identify galactose-dependent histidine prototrophs. Many of the colonies growing on the initial selection plates did not show galactose-dependent growth in this subsequent screen. These colonies may arise from several sources, including spontaneous AT resistance, genomic alterations to activate the pheromone response pathway, and spontaneous mutations leading to reversion of the genomic his3 allele or constitutive activation of the FUS1 promoter. By expressing cDNAs under control of an inducible promoter, most colonies with plasmid-independent growth were eliminated by this rapid and simple secondary screen (see Table 2A & 2B).

Plasmids were isolated from strains showing galactose-dependent growth and used to re-transform naive CY1316/1183 strains. Transformants were again plated onto sucrose medium, then replica-plated onto both galactose and glucose medium lacking histidine and containing 1 mM AT. Those plasmids that conferred universal galactose-dependent growth on this medium were considered to carry cDNAs encoding pheromone pathway activators. Eight such plasmids were identified from these screens, each containing the same open reading frame downstream of the GAL1 promoter (designated L1, see Table 2).

TABLE 2A & 2B

| Characteristics of yeast screens | |
| --- | --- |
| Library | Liver |
| A. Activator Screens | |
| Transformants | ~3 × 10⁵ |
| Primary screen | 146 |
| Secondary screen | 16 |
| Retransformation | 8 |
| ORF (Frequency) | L1 (8) |

TABLE 2A & 2B-continued

Characteristics of yeast screens

| | Library | Liver |
|---|---|---|
| B. Activator Screens | | |
| Transformants | | ~1.3 × 10⁶ |
| Primary screen | | 238 |
| Secondary screen | | 1 |
| Retransformation | | 1 |

Footnote to Table 2A
CY1316/1183 transformants were screened for colony growth on galactose medium lacking histidine and containing aminotriazole (Primary screen), then for galactose-dependent (Secondary screen) and plasmid-dependent (Retransformation) colony growth. Open reading frames (ORF) downstream of the yeast GAL1 promoter are designated L1 with their frequency of occurrence in parenthesis. See text for details.

Footnote to Table 2B
CY1141/1451-AGS1/2440 transformants were screened for colony growth on galactose medium lacking arginine and containing canavanine (Primary screen), then for galactose-dependent (Secondary screen) and plasmid-dependent (Retransformation) colony growth. The sole isolate from this screen carried on ORF downstream of the GAL1 promoter encoding human RGS5.

All were found to contain the same open reading frame of 846 bases encoding a protein of 281 amino acids, shown in FIGS. 3C-1 and 3C-2 (the nucleotide sequence of which is also shown in SEQ ID NO:1 and the encoded amino acid sequence of which is also shown in SEQ ID NO:2). The open reading frame of these isolates was designated AGS, for Activator of G-protein Signaling. Each isolate contained varying amounts of 5' and 3' untranslated sequence, and therefore appears to have been selected independently. A composite AGS nucleotide sequence containing the longest identified 5' and 3' untranslated regions of AGS is shown in SEQ ID NO:3.

Example 3

AGS-Mediated Activation of the Pheromone Pathway Occurs at the Level of the Heterotrimeric G-Protein Strains carrying pYES2-AGS1 exhibit galactose-dependent growth as well as galactose-dependent reporter gene activity (in strains also carrying the FUS1p-lacZ construct). The galactose-dependent growth phenotype conferred upon strain CY1316/CP1183 by pYES2-AGS was further characterized by genetic analysis. pYES2-AGS fails to confer galactose-dependent growth on medium lacking histidine and containing 1 mM AT to strains CY4600, CY12444 and CY12970, containing, respectively genomic disruptions of STE4, STE5, and STE20 (see Table 1). This lack of growth is consistent with AGS activation of signaling occurring through the pheromone response pathway (GDy→PAK→MAPK cascade). Neither were the isolates of strains carrying an episomal copy of human RGS4 under control of the constitutive PGK1 promoter able to confer galactose-dependent growth. Furthermore, the inability of AGS to confer growth on a strain deleted for Gβ is consistent with AGS-mediated activation occurring at or above the level of the heterotrimeric G-protein.

Plasmid pYES2-AGS was also unable to confer galactose-dependent growth on medium lacking histidine and containing 1 mM AT to strain CY1316/CP5533, carrying the G204A allele of GPA1$_{(1-41)}$-Gαi2. Three independent isolates each of strains CY1316/pYES2 and CY1316/pYES2-AGS carry plasmid CP5533 (G204A), and one isolate each of strains CY1316/pYES2 and CY1316/pYES2-AGS carrying plasmid CP1183 (WT) were grown on sucrose medium for 2 days. Equal numbers of cells were then resuspended in sterile H$_2$O and spotted onto galactose medium lacking histidine and containing 1 mM AT. Cells were grown 2 d at 30° prior to photography to visualize growth. Neither the isolates of strains CY1316/pYES2 or CY1316/pYES2-AGS carrying plasmid CP5533 (G204A), exhibited growth above that seen with control strain CY1316/pYES2 carrying plasmid CP1183 (WT). By contrast, positive control strain CY1316/pYES2-AGS carrying plasmid CP1183 (WT) exhibited significant colony growth. The G204A mutation is analogous to the G226A mutation in Gαs which renders this protein unable to form a high affinity Mg$^{2+}$ GTP complex (Lee et al. (1992) *J. Biol. Chem.* 267:1212–1218). The G204A mutation in the chimeric Gpa1$_{(1-41)}$-Gαi2 also appears to render it incapable of activation, as evidenced by its failure to transduce a receptor-mediated signal to activate fus1p-HIS3 transcription.

To rule out that AGS expression was affecting the expression of the Gpa1$_{(1-41)}$-Gαi2 chimera, membrane preparations from strains CY1316/CP1183 and CY1316/CP5533 expressing either the pYES2 vector or the pYES2-AGS plasmid and grown for 20 hours in galactose-containing medium were analyzed by immunoblot analysis using antisera specific for the C-terminus of Gαi2. No significant differences in chimeric Gpa1$_{(1-41)}$-Gαi2 expression were detected in any of these strains.

These data strongly suggest that AGS activation of the pheromone response pathway is occurring at the level of the heterotrimeric G protein. Furthermore, the inability of AGS to activate the pheromone response pathway in the presence of a Gα that is defective in GDP-GTP exchange, and the opposing effects of AGS function and RGS4 function on pheromone pathway activation strongly suggest that AGS functions by facilitating GTP exchange on the heterotrimeric Gα. Finally, the Gα selectivity profile of AGS1 was determined. The pYES/FUS1p-lacZ transformants in strain CY1316 (no Gα), or CY1316 derivatives carrying an integrated copy of a GPA1-human Gαi2 fusion construct (CY1141), a GPA1-human Gαi3 fusion construct (CY7967), a rat Gαs construct (CY8342), a GPA1-human Gα16 fusion construct (CY9603), or yeast GPA1 (CY9571) (all under the control of the yeast GPA1 promoter) were grown in selective liquid medium containing either glucose or galactose. Relative β-galactosidase activity was then determined on aliquots of permeablized cells (Table 3).

TABLE 3

| | β-galactosidase activity | | | |
|---|---|---|---|---|
| | VECTOR | VECTOR | AGS1 | AGS1 |
| Strain | Glucose | Galactose | Glucose | Galactose |
| No Gα | 103.4 ± 5.7 | 76.0 ± 6.9 | 145.0 ± 5.9 | 140.1 ± 4.4 |
| Gαi2 | 11.1 ± 0.9 | 8.7 ± 0.5 | 5.6 ± 0.6 | 124.8 ± 4.1 |
| Gαi3 | 10.0 ± 0.6 | 9.8 ± 0.6 | 5.6 ± 0.7 | 63.3 ± 7.8 |
| Gαs | 13.3 ± 1.0 | 11.9 ± 0.8 | 10.1 ± 0.5 | 6.4 ± 1.1 |
| Gα16 | 23.6 ± 0.7 | 24.3 ± 1.6 | 22.5 ± 1.2 | 22.5 ± 1.6 |
| Gpa1 | 5.6 ± 0.3 | 5.4 ± 0.3 | 3.6 ± 0.5 | 7.6 ± 0.8 |

Analysis of the Gα selectivity profile for AGS1 in yeast strains carrying a fus1p-lacZ reporter construct and expressing different mammalian Gα constructs indicated Gαi specificity. Expression of AGS1 resulted in high levels of β-galactosidase activity in strains expressing GPA1$_{(1-41)}$-Gαi2 or GPA1$_{(1-41)}$-Gαi3, but not in strains expressing Gαs, GPA1$_{(1-41)}$-Gα16 or GPA1 itself (Table 3).

Immunoblot analysis using polyclonal serum against Gpa1 and Gαs indicated that each of the host strains expressed equivalent amounts of Gα and that expression of AGS1 had no significant effect on the steady-state levels of any of these Gα proteins. Similar experiments indicated that expression of AGS1 had no significant effect on the steady-state levels of yeast Gβ.

Example 4

A Counter-screen for Pheromone Pathway Inhibitors

With the identification of AGS1 as a receptor-independent mammalian activator of the yeast pheromone response pathway, a novel screen was devised to identify pheromone pathway inhibitors. For this screen, a strain was created that had its pheromone pathway constitutively activated by AGS1. Then, a human liver cDNA library in vector pYES2 was introduced into this strain in an attempt to identify cDNAs that, when expressed, counteracted AGS1 function. This screen, therefore, can identify proteins that both directly and indirectly regulate AGS1 activity.

In this screen, the marker gene CAN1 was employed which encodes a yeast arginine permease that can transport the arginine analog canavanine (Sikorski (1991) *Meth. Enz.* 194:302–318). Accordingly, cells expressing Can1 and cultured in the absence of arginine can transport canavanine and incorporate it into nascent proteins, leading to cell death. By fusing CAN1 coding sequences downstream of the FUS1 promoter and introducing it into yeast strain CY1141 (Table 1), this strain can be made conditionally non-viable upon pheromone pathway activation. Into this strain the AGS1 coding sequences fused downstream of the constitutive yeast promoter PGK1 were introduced (Schena et al. (1991), *Meth. Enz.* 194:389–398). Expression of AGS1 in this strain led to constitutive pheromone pathway activation, as evidenced by growth on medium lacking histidine and inhibition of growth on medium lacking arginine and containing canavanine.

The observation was made that the constitutive expression of human RGS4 interfered with AGS1 function. Thus, RGS4 was ligated downstream of the GAL1 promoter in pYES2 and used as an initial proof-of-concept test for the inhibitor screen. When introduced into CY1141 carrying PGK1p-AGS1 and FUS1p-CAN1 expression constructs, pYES2-RGS4 conferred galactose-dependent growth on medium lacking arginine and containing canavanine. The amount of canavanine used in this test (200 μg/ml medium) was determined to be optimal in suppressing the growth of pYES2 vector transformants without causing general lethality. Therefore the strain was transformed with the human liver cDNA library and a inhibitor screen analogous to the activator screen was carried out. A schematic of the inhibitor screen is shown in FIG. 2 and the screen characteristics are shown in Table 2. A higher level of plasmid-independent colony formation was expected from this screen relative to that of the activator screen, as any genomic mutation that abolishes pheromone pathway signalling should confer growth under restrictive conditions. This background, again, was easily eliminated with a secondary screen comparing growth on glucose medium versus growth on galactose medium. In addition, a higher level of general background growth in this screen was encountered compared with the activator screen. An additional replica-plating step in the secondary screen eliminated much of this background (see Table 3). In the initial screen of 1.3×10⁶ primary transformants, a single cDNA clone (L15) was isolated that was capable of conferring growth in a galactose-specific manner under selective conditions. Sequencing of the 1.7 kilobase cDNA insert (SEQ ID NO:24) revealed it to encode human RGS5 (SEQ ID NO:25). Human RGS5 is an ortholog of mouse RGS5, which has been shown to bind in vitro to both Gαi and Gαo (Chen et al. (1997) *J. Biol. Chem.* 272:8679–8685).

The ability to isolate one member of a family of known down-regulators of heterotrimeric G-protein signaling pathways not only serves to validate this inhibitor screen, but also to reinforce the mechanism of action of AGS1.

In summary, the functional redundancy found in many key regulatory pathways of both yeast and mammalian cells allows for the development of screens designed to identify specific modulators of these pathways. The ability to isolate both mammalian activators and inhibitors of the yeast pheromone response pathway demonstrates the utility of these yeast-based functional screens. Moreover, the short time frame required for each screen (1–2 weeks), as well as the relatively high throughput (Table 3), allows for rapid saturation screens for a cDNA library of interest. Accordingly, the implementation of these screens using cDNA libraries generated from different normal or disease-specific tissue sources can be used to identify other novel pathway activators or inhibitors.

Example 5

Characterization of Isolated cDNA Clone

The open reading frame of the 8 isolated clones encodes a 281 amino acid protein with homology to small ras-like G proteins. This newly cloned protein was termed AGS. A search of GenBank revealed that AGS exhibits homology (96% at the amino acid level, 85% at the nucleotide level) with a previously identified glucocorticoid-induced ras-related protein in mouse (accession number AF009246). Sequence comparison with the yeast genome indicated that AGS shares the highest degree of homology with RSR1/BUD1 (45% amino acid identity within amino acids 25–125 of AGS) and both RAS1 and RAS2 (43% amino acid identity within amino acids 25–125 of AGS). An alignment of AGS with representatives of all major classes of small G proteins in humans (FIGS. 7A and 7B) indicates that AGS is likely to be the founding member of a novel class of small G proteins in humans.

Though AGS is clearly a member of the ras superfamily, it has several unique structural features, including both N- and C-terminal extensions not seen in most small G proteins. AGS also has alterations in several amino acids that are normally highly conserved in all small G proteins. Indeed, AGS shares alterations at three key amino acid residues with the recently identified G proteins Rnd1, Rnd2 and RhoE/Rnd3 (Foster et al. (1996) *Mol. Cell. Biol.* 16:2689–2699; Nobes et al. (1998) *J. Cell Biol.* 141:187–197) (see FIG. 8). RhoE was shown to be deficient in GTP hydrolysis activity, and this deficiency could be restored by alteration of these three amino acids to their highly conserved counterparts (Foster, R. et al. (1996) Mol. Cell. Biol. 16:2689–2699). Though AGS shares these three amino acid alterations with Rnd1, Rnd2 and RhoE/Rnd3, it does not share the consensus rho effector (amino acids 42–50 in Rnd1) or rho insert (amino acids 132–140 in Rnd1) domains of these proteins. AGS, therefore, does not appear to be a member of the rho family of ras-like proteins.

Example 6

Mutational Analysis of AGS Protein

A series of point mutations were created in AGS to analyze their effects on pheromone pathway activation, as measured by galactose-dependent growth in the absence of histidine. Mutations at conserved glycine residues 31 and 36, which are predicted to be in the P site, render AGS unable to confer histidine prototrophy to cells. Surprisingly, mutation of another conserved glycine in the G' site, glycine-81, does not appear to affect the function of AGS, even with growth on medium containing 20 mM AT. This glycine mutation is analogous to the G(226)A mutation of Gαs and the G204A mutation of Gαi2, and would normally be predicted to by an inactivating mutation.

A number of other mutants (listed below in table 4) were tested in the vector pYES2 in CY1141 on medium lacking histidine and containing 1 mM aminotriazole as described above. The β-galactosidase activities (relative to wild-type AGS1) of all of the mutants tested are as follows.

TABLE 4

| Construct | β-gal activity (glucose) | β-gal activity (galactose) |
| --- | --- | --- |
| Wild type | 8.5 | 100 |
| G(31)V | 11.1 | 8.2 |
| G(36)V | 10.3 | 10.9 |
| G(81)A | 9.3 | 69.6 |
| S(33)G | 8.4 | 68.6 |
| S(80)A | 10.1 | 104.0 |
| N(82)G | 12.2 | 66.0 |
| F(44)N | not tested | not tested |
| S(33)G; S(80)A | 9.3 | 39.1 |
| S(33)G; N(82)A | 10.1 | 37.2 |
| S(80)A; N(82)G | 9.9 | 92.6 |
| S(33)G; S(83)A; N(82)G | 7.7 | 71.1 |
| S(33)G; S(80)A; N(82)G; G(81)A | 12.0 | 125.5 |
| K(225)E; K(226)E | 13.0 | 81.0 |
| C(278)S | 14.4 | 16.4 |
| Vector | 10.1 | 8.9 |

The G(31)V mutant carried a glycine to valine alteration at residue 31 (G31V), an absolutely conserved residue in the P-loop of monomeric G proteins that makes critical contacts with the α- and β-phosphates of both GDP and GTP (Valencia et al. (1991) Biochemistry 30:4637–4648). The C(278)S mutant carried a cysteine to serine alteration at residue 278 (C278S) within the C-terminal CAAX box. This cysteine is a major site of lipid modification for most members of the ras superfamily. Neither of these mutations appeared to destabilize the AGS1 protein, as immunoblot analysis of both N-terminally $His_6$- and GST-tagged mutant proteins showed no significant change in the steady-state levels relative to wild-type AGS1. The introduction of either of these two amino acid changes in AGS1, however, severely impaired its ability to activate the pheromone pathway consistent with AGS1 function requiring both guanine nucleotide binding and post-translational lipid modification.

Example 7

Effect of STE14 on AGS Function

The yeast strain used in the isolation of AGS contained a genomic disruption of the STE14 locus, which encodes a farnesyl cysteine:carboxyl methyltransferase known to carboxymethylate the yeast Gα, Ste18, Ras1 and Ras2 proteins as well as a-factor (Hrycyna and Clarke (1990) *Mol. Cell. Biol.* 10:5071–5076; Marr et al. (1990) J. Biol. Chem. 265:20057–20060; Hrycyna et al. (1991) EMBO J. 10:1699–1709). Disruption of ste14 has been found to reduce background signaling through the pheromone response pathway in strains carrying chimeric Gα constructs. Because AGS appears to encode a small ras-related G protein with a C-terminal CaaX box sequence consistent with farnesylation, and because small G proteins are often carboxymethylated after farnesylation, we examined the effect of addition of an episomal copy of STE14 on AGS function. STE14 gene expression appeared to enhance the fus1-HIS3 mediated growth of strains expressing AGS, though an increase in background growth on glucose medium was also evident.

Example 8

Tissue Expression of AGS mRNA

The tissue-specific expression of AGS in mRNAs isolated from various human tissues was measured. A $^{32}$P-labeled DNA probe was made from the full length coding sequence of AGS and hybridized under stringent conditions to mRNA Northern blots and an mRNA dot blot generated from human tissues and human cancer cell lines. The AGS probe hybridized to a major transcript at approximately 2 kb and a minor transcript at approximately 5 kb. The major transcript hybridized most strongly with mRNAs derived from liver, skeletal muscle, heart, kidney, brain and placenta, prostate and bone marrow tissues, as well as from a HeLa cell line. Interestingly, the relative ratio of the major and minor transcripts varies with tissue source, and the major transcript is almost entirely absent from mRNA derived from fetal liver. Upon longer exposure times, hybridization to the AGS probe is detectable in all mRNA samples, probably indicating low-level of AGS expression in all tissues.

Example 9

Chromosomal Localization of AGS1

In a further characterization of the AGS1 gene, the chromosomal locus of AGS1 was determined according to the protocol of Genome Systems, Inc. (St. Louis, Mo.). A full length AGS1 cDNA (SEQ ID NO:1) was used to identify a P1 genomic clone from a human library. This P1 clone, with fluorescence in situ (FISH), localized the AGS1 gene to chromosome 17 in band 17p11.2. AGS1 sequences were localized to 38% of the distance from the centromere to the telomere of chromosome arm 17p, and 71 out of 80 metaphase chromosome spreads that were analyzed exhibited specific labeling with an AGS1 probe. The homolog of AGS1 has been (as described in Example 15) localized to chromosome 22 in band 22q13.1. A P1 genomic clone carrying AGS1 has been analyzed by PCR amplification using the oligo sequences 5' TTCTCGCGGATGTA-CATGA33' (SEQ ID NO:43) and 5' TCCACCGCAAGT-TCTACTCC3' (SEQ ID NO:44) and verified, by size analysis, to contain an AGS1 DNA sequence.

Example 10

Expression of AGS Protein in Host Cells

Coding sequences for AGS were amplified by PCR for expression in yeast, *E. coli*, insect, and mammalian cells. These sequences were ligated downstream of coding sequences for either GST or $His_6$ epitopes, and protein expression levels were monitored by immunoblot analysis using antisera directed against the respective fusion partners. Inducible expression of GST-tagged AGS in yeast and bacteria was easily detectable. The expression of mutant forms of AGS in yeast, in which glycine residues 36 and 81 were changed, respectively, to valine and alanine was also detectable, as was the expression of His$_6$-tagged AGS in insect cells. A His$_6$-tagged version of AGS was also introduced into the mammalian cell line HEK293, and stable transfectants generated. The expression of tagged AGS mRNA in these cell lines was detectable, but expression of AGS protein was not, indicating that AGS protein may be unstable in this cell line.

However, both wild type and AGS1 mutant G(31)V have been expressed and detected in mammalian CHO-K1 and COS-7 cells and both polypeptides are membrane associated. No AGS1 protein is detectable in the soluble fraction. In addition, in yeast, expression of wild type, G(31)V, G(36)V, G(81)A, and S(33)G; S(80)A; N(82)G AGS1 fusions to GST have been detected in whole cell yeast extracts. An in vitro translation reaction was performed to verify expression of His$_6$-tagged AGS from pcDNA3.1-HisC-AGS, as well as to verify expression of non-tagged AGS from the original pYES2-AGS isolate. Expression of $^{35}$S-labeled AGS was readily detectable from these plasmids.

GST- and His$_6$-fusions of AGS were purified by affinity chromatography from $E.$ $coli$ or yeast ($S.$ $cerevisiae$) and insect cells using, respectively, glutathione sepharose and Ni-agarose matrices. A GST-fusion of Cdc42 was also purified from $E.$ $coli$ and yeast. Purification was monitored by SDS-polyacrylamide gel electrophoresis and immunoblotting. Large amounts of purified soluble GST-fusion proteins can be readily obtained from bacterial cultures and yeast cultures. GST-AGS appears to be relatively unstable during purification, even with buffers containing high levels of Mg$^{2+}$ and either GDP or GTP.

Example 11

Association of Heterotrimeric G-Protein Subunits with GST-AGS1

Purified GST or GST-AGS1, from yeast was incubated with crude extract from Sf9 cells expressing human His$_6$-Gαi2 or yeast Gβ-His$_6$Gγ. Gαi2 extracts were pre-incubated with excess GDP or GTPγS prior to incubation with immobilized proteins. After extensive washing, bound Gαi2 and Gγ were detected with antiserum specific to the hexahistidine tag, and bound Gβ was detected with antiserum specific to Ste4. This GST-AGS1 construct expressed in yeast is functional, conferring histidine prototrophy to CY1316/1183.

Example 12

AGS1 Stimulates GTP Binding to Gα Subunits

GST-AGS1 was assayed for its ability to enhance binding of GTPγS to purified Gαi1 and Gαi2. Under conditions used to monitor G-protein activation by a GPCR (Sato et al. (1996), J. Biol. Chem. 271:30052–30060), addition of AGS1 clearly enhanced GTPγS binding on both Gα proteins (approximately 25% purified Gα was bound to GTPγS at 40 minutes in the presence of AGS1 as compared to approximately 7% bound at 40 minutes in the absence of AGS1). AGS1 also was able to enhance GTPγS binding to a similar extent on purified brain heterotrimeric G-protein, where the majority of Go in the heterotrimer is Gαo, suggesting AGS1 also functions on Gαo and functions independently of the presence of Gβγ. These observations, in combination with the in vivo epistasis and Gα selectivity data, indicate that AGS1 likely functions by catalyzing guanine nucleotide exchange on selected Gα proteins. Purified GST-AGS1 alone does not bind GTPγS under these conditions, nor does it bind GTPγS when presented in the absence of excess GDP. Two control experiments were done to assess where the labelled GTPγS was being bound in these assays. First, Ni-NTA agarose and glutathione sepharose were used to pull out either His$_6$-Gαi2 or GST-AGS1 after 40 minutes, and the majority of GTPγS counts were found on the Ni-NTA column. Second, purified Gαi2 was pre-loaded with non-labelled GTPγS, dialyzed, and used in the assay. This led to an approximately 70% decrease in label bound. The converse experiment, in which purified GST-AGS1 was pre-loaded with cold GTPγS prior to running the assay showed only an approximately 15% decrease in label bound.

Example 13

Induced Expression of AGS-1 Activities ERK1/ERK2 Pathway

AGS1 and a His$_6$-tagged version of AGS1 have also been constructed in the ecdysone (ponasterone)-inducible mammalian expression vector pIND (Invitrogen) using standard techniques. Upon induction, assays for determining activation of MAP kinase pathways were performed on cells carrying inducible pIND-AGS1 constructs. These assays indicated that in HEK293 cells, the ERK1/ERK2 pathway is activated upon induction of expression of AGS1 and that this activation is abolished by pretreatment of cells with pertussis toxin (Ptx) (Table 5).

TABLE 5

| Sample | ERK1/ERK2 activation (cpm) ± S.E.M. |
|---|---|
| pIND-AGS1(uninduced) | 21710 ± 1530 |
| pIND-AGS1(induced) | 32070 ± 1270 |
| pIND-AGS1 + Ptx(uninduced) | 23700 ± 960 |
| pIND-AGS1 + Ptx(induced) | 26460 ± 400 |

Example 14

GTPase Analysis of AGS1

AGS1 has been determined to have GTPase activity. Using a standard GTPase assay as described herein, it was determined that purified GST-AGS1 preparations have significant GTPase activity. For example, at 120 minutes, the amount of phosphate released into the buffer was 4.8 pmol per 25 pmol GST (background is 4 pmol), 28 pmol per 25 pmol GST-AGS1, and 33 pmol per 25 pmol GST-Cdc42. Also, there was a time and AGS1 dose-dependence for phosphate release. Neither excess phosphate nor excess ATP could significantly affect the degree of phosphate release for GST-AGS1 or GST-Cdc42, but excess unlabelled GDP and GTP inhibited the rate of phosphate release, indicating that both GST-AGS1 and GST-Cdc42 are specifically hydrolyzing GTP (e.g. there is not a contaminating non-specific nucleotidase or phosphatase activity in the preparations).

In addition, it was determined by in vivo labeling with $^{32}$PO$_4$ as described herein that AGS1 bound nucleotide much less well than Cdc42. GST-Cdc42, as expected, was mostly bound to GTP after purification from strain CY1316 (pathway on), and GDP after purification from strain CY4600 (pathway off). AGS1, however, seemed to be bound only to GTP when purified from either strain background-no GDP was detected at all in either sample. Relative to Cdc42, it is estimated that less than 1% of AGS1 is bound to nucleotide after purification.

Taken together, the above biochemistry suggests that AGS1 can only bind guanine nucleotides poorly and has lower affinity for GDP as compared to GTP. Given that its GTPase activity is comparable (mol:mol) with Cdc42, this would suggest that purified AGS1 may have a higher than normal hydrolysis activity. Accordingly, it is likely that only a small fraction of purified AGS1 is active, accounting for the relatively low stimulation of GTPYS binding seen when used in the activation assay and for its apparent instability.

Example 15

Cloning and Analysis of a Human AGS1 Homolog

By sequence comparison, a related human AGS1 homolog was identified from the GenBank database (Accession No.: CAA18456). Alignment of the AGS1 polypeptide sequence to the AGS1 homolog indicated that these proteins were 62% identical when comparing residues 5–280 of AGS1 (SEQ ID NO:2) to residues 12–227 of the AGS1 homolog (SEQ ID NO:41). In addition, the cDNAs encoding these proteins were 82% and 84% identical when comparing AGS1 nucleotide bases 102–438 and 510–646 of SEQ ID NO:1 with, respectively, AGS1 homolog nucleotide bases 123–459 and 531–667 of SEQ ID NO:40. The overall greatest divergence between these two molecules is found in the C-terminal or 3' region of these molecules. Given the above sequence similarity between AGS1 and the AGS1 homolog, a functional analysis of these related molecules was conducted. The cDNA for the AGS1 homolog was amplified by PCR from a human liver cDNA library and subcloned into pYES2 vector using engineered 5' BamHI and 3' EcoRI sites (as had been done for AGS1 itself). Expression of this homolog did not confer growth to CY1316/1183, nor did it lead to FUS1p-lacZ activity in CY1141 (see Table 6). A common internal MscI site in both AGS1 and the AGS1 homolog was taken advantage of in order to exchange the C-terminal regions between these two sequences. The chimeric expression constructs were called AH (for AGS1 head and Homolog tail) and HA (for Homolog head and AGS1 tail), and were ligated into the pYES2 vector. Even though the major divergence between these two sequences is in the "tail" region, both growth assays and lacZ assays indicated that the "head" or N-terminal region of AGS1 is important for activity as measured as a function of relative lacZ activities as shown below (Table 6).

TABLE 6

Functional Analysis of AGS1, AGS1 Homolog, and Chimeric Proteins

| Construct | β-gal activity (glucose) | β-gal activity (galactose) |
|---|---|---|
| pYES2-AGS1 | 12.0 | 100.0 |
| pYES2-Homolog | 10.2 | 12.3 |
| pYES2-AH | 11.3 | 52.5 |

TABLE 6-continued

Functional Analysis of AGS1, AGS1 Homolog, and Chimeric Proteins

| Construct | β-gal activity (glucose) | β-gal activity (galactose) |
|---|---|---|
| pYES2-HA | 13.9 | 14.0 |
| pYES2 vector | 11.3 | 12.2 |

Example 16

Cloning of AGS1 Genomic DNA

A cDNA clone of AGS1 was used as a probe to isolate a P1 clone (containing greater than 100 kb of human sequence), using standard techniques of molecular biology (e.g. see Genome Analysis, A Laboratory Manual, Editors, Birren, B et. al., 1997, Volumes 1 to 4, Cold Spring Harbor Laboratory). Various restriction digests of this P1 clone were subjected to Southern analysis, using the cDNA sequence as a probe. A single 4990 bp BamHI-EcoRI fragment was identified that hybridized to this cDNA probe. This was subcloned into pUC18 and fully sequenced. The sequence is shown in FIG. 9 (SEQ ID NO: 73). There is a natural 5' BamHI site and a natural 3' EcoRI site in this sequence. The coding region for AGS1 is shown in bold, with the likely intron-exon junctions, based on consensus sequences (Breathnach, R., and Chambon, P. (1981) Organization and expression of eucaryotic split genes coding for proteins. Ann. Rev. Biochem. 50:349–383).

The promoter region of AGS1 from nucleotide 1–2709 was excised as a BstY1 fragment from the pUC18-AGS1 clone and placed upstream of the luciferase reporter in plasmid pGL3 Basic (Promega, Madison, Wis.). This construct can be transfected into eukaryotic cells to study its transcriptional regulatory sequences, binding proteins, and their regulation, by monitoring expression of luciferase, and such cells can also be used in screens for chemicals or other agents which modulate transcription via these sequences or proteins which interact with them.

This region from nucleotide 1–2709 has been analyzed using the program MatInspector (Quandt, K., Frech, K., Karas, H., Wingender, E., and Werner, T. (1995) MatInd and MatInspector—New fast and versatile tools for detection of consensus matches in nucleotide sequence data, Nuclei Acids Research 23:4878–4884) and found to contain many potential transcription factor binding sites (e.g. AP1, AP2, CREB, NFAT, GATA, NF-Y, OCT-1) as well as GC (SP-1) and TATA (TFII-D) boxes, as would be expected for a transcriptional regulatory sequence.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid comprising the nucleotide sequence as set forth in SEQ ID NO:73.

2. A promoter sequence having nucleotides 1–2710 as set forth in SEQ ID NO:73.

3. A nucleic acid construct comprising a promoter sequence having nucleotides 1–2710 as set forth in SEQ ID NO:73 operably linked to a heterologous sequence of nucleic acid.

4. The nucleic acid construct of claim 3, wherein the heterologous sequence of nucleic acid is a coding sequence.

5. The nucleic acid construct of claim 3, wherein the heterologous sequence of nucleic acid encodes a reporter molecule.

6. The nucleic acid construct of claim 4, wherein the coding sequence is a luciferase reporter molecule.

7. The nucleic acid construct of claim 3, further comprising nucleotides 3956–4990 as set forth in SEQ ID NO:73, wherein nucleotide 3956 is linked to the 3' end of the heterologous sequence.

8. A host cell comprising the nucleic acid construct of claim 3.

9. A process of transcribing a heterologous sequence of nucleic acid, comprising culturing the host cells of claim 8 under conditions that result in transcription of the heterologous sequence of the nucleic acid construct and harvesting the transcription product from the heterologous sequence.

10. A process of expressing a peptide or polypeptide encoded by a heterologous sequence of nucleic acid comprising culturing the host cell of claim 8 under conditions that result in expression of the peptide or polypeptide encoded by the heterologous sequence of the nucleic acid construct.

* * * * *

SEQUENCE LISTING

<160> NUMBER OF SEQ ID NOS: 118

<210> SEQ ID NO 1
<211> LENGTH: 846
<212> TYPE: DNA
<213> ORGANISM: Homo sapiens
<220> FEATURE:
<221> NAME/KEY: CDS
<222> LOCATION: (1)..(843)
<223> OTHER INFORMATION:

<400> SEQUENCE: 1

```
atg aaa ctg gcc gcg atg atc aag aag atg tgc ccg agc gac tcg gag      48
Met Lys Leu Ala Ala Met Ile Lys Lys Met Cys Pro Ser Asp Ser Glu
1               5                  10                  15 ctg agt atc ccg gcc aag aac tgc tat cgc atg gtc atc ctc ggc tcg      96
Leu Ser Ile Pro Ala Lys Asn Cys Tyr Arg Met Val Ile Leu Gly Ser
            20                  25                  30 tcc aag gtg ggc aag acg gcc atc gtg tcg cgc ttc ctc acc ggc cgc     144
Ser Lys Val Gly Lys Thr Ala Ile Val Ser Arg Phe Leu Thr Gly Arg
        35                  40                  45 ttc gag gac gcc tac acg cct acc atc gag gac ttc cac cgc aag ttc     192
Phe Glu Asp Ala Tyr Thr Pro Thr Ile Glu Asp Phe His Arg Lys Phe
    50                  55                  60 tac tcc atc cgc ggc gag gtc tac cag ctc gac atc ctc gac acg tcc     240
Tyr Ser Ile Arg Gly Glu Val Tyr Gln Leu Asp Ile Leu Asp Thr Ser
65                  70                  75                  80 ggc aac cac ccg ttc ccc gcc atg cgg cgc ctc tcc atc ctc aca gga     288
Gly Asn His Pro Phe Pro Ala Met Arg Arg Leu Ser Ile Leu Thr Gly
                85                  90                  95 gac gtt ttc atc ctg gtg ttc agt ctg gac aac cgc gac tcc ttc gag     336
Asp Val Phe Ile Leu Val Phe Ser Leu Asp Asn Arg Asp Ser Phe Glu
            100                 105                 110 gag gtg cag cgg ctc agg cag cag atc ctc gac acc aag tct tgc ctc     384
Glu Val Gln Arg Leu Arg Gln Gln Ile Leu Asp Thr Lys Ser Cys Leu
        115                 120                 125 aag aac aaa acc aag gag aac gtg gac gtg ccc ctg gtc atc tgc ggc     432
Lys Asn Lys Thr Lys Glu Asn Val Asp Val Pro Leu Val Ile Cys Gly
    130                 135                 140 aac aag ggt gac cgc gac ttc tac cgc gag gtg gac cag cgc gag atc     480
Asn Lys Gly Asp Arg Asp Phe Tyr Arg Glu Val Asp Gln Arg Glu Ile
145                 150                 155                 160 gag cag ctg gtg ggc gac gac ccc cag cgc tgc gcc tac ttc gag atc     528
Glu Gln Leu Val Gly Asp Asp Pro Gln Arg Cys Ala Tyr Phe Glu Ile
                165                 170                 175 tcg gcc aag aag aac agc agc ctg gac cag atg ttc cgc gcg ctc ttc     576
Ser Ala Lys Lys Asn Ser Ser Leu Asp Gln Met Phe Arg Ala Leu Phe
            180                 185                 190 gcc atg gcc aag ctg ccc agc gag atg agc cca gac ctg cac cgc aag     624
Ala Met Ala Lys Leu Pro Ser Glu Met Ser Pro Asp Leu His Arg Lys
        195                 200                 205 gtc tcg gtg cag tac tgc gac gtg ctg cac aag aag gcg ctg cgg aac     672
Val Ser Val Gln Tyr Cys Asp Val Leu His Lys Lys Ala Leu Arg Asn
    210                 215                 220 aag aag ctg ctg cgg gcc ggc agc ggc ggc ggc ggc gac ccg ggc         720
Lys Lys Leu Leu Arg Ala Gly Ser Gly Gly Gly Gly Asp Pro Gly
225                 230                 235                 240 gac gcc ttt ggc atc gtg gca ccc ttc gcg cgc cgg ccc agc gta cac     768
Asp Ala Phe Gly Ile Val Ala Pro Phe Ala Arg Arg Pro Ser Val His
                245                 250                 255
```

```
agc gac ctc atg tac atc cgc gag aag gcc agc gcc ggc agc cag gcc    816
Ser Asp Leu Met Tyr Ile Arg Glu Lys Ala Ser Ala Gly Ser Gln Ala
            260                 265                 270 aag gac aag gag cgc tgc gtc atc agc tag                            846
Lys Asp Lys Glu Arg Cys Val Ile Ser
        275                 280
```

<210> SEQ ID NO 2
<211> LENGTH: 281
<212> TYPE: PRT
<213> ORGANISM: Homo sapiens

<400> SEQUENCE: 2

```
Met Lys Leu Ala Ala Met Ile Lys Lys Met Cys Pro Ser Asp Ser Glu
1               5                   10                  15

Leu Ser Ile Pro Ala Lys Asn Cys Tyr Arg Met Val Ile Leu Gly Ser
                20                  25                  30

Ser Lys Val Gly Lys Thr Ala Ile Val Ser Arg Phe Leu Thr Gly Arg
            35                  40                  45

Phe Glu Asp Ala Tyr Thr Pro Thr Ile Glu Asp Phe His Arg Lys Phe
        50                  55                  60

Tyr Ser Ile Arg Gly Glu Val Tyr Gln Leu Asp Ile Leu Asp Thr Ser
65                  70                  75                  80

Gly Asn His Pro Phe Pro Ala Met Arg Arg Leu Ser Ile Leu Thr Gly
                85                  90                  95

Asp Val Phe Ile Leu Val Phe Ser Leu Asp Asn Arg Asp Ser Phe Glu
                100                 105                 110

Glu Val Gln Arg Leu Arg Gln Gln Ile Leu Asp Thr Lys Ser Cys Leu
            115                 120                 125

Lys Asn Lys Thr Lys Glu Asn Val Asp Val Pro Leu Val Ile Cys Gly
130                 135                 140

Asn Lys Gly Asp Arg Asp Phe Tyr Arg Glu Val Asp Gln Arg Glu Ile
145                 150                 155                 160

Glu Gln Leu Val Gly Asp Asp Pro Gln Arg Cys Ala Tyr Phe Glu Ile
                165                 170                 175

Ser Ala Lys Lys Asn Ser Ser Leu Asp Gln Met Phe Arg Ala Leu Phe
            180                 185                 190

Ala Met Ala Lys Leu Pro Ser Glu Met Ser Pro Asp Leu His Arg Lys
        195                 200                 205

Val Ser Val Gln Tyr Cys Asp Val Leu His Lys Lys Ala Leu Arg Asn
210                 215                 220

Lys Lys Leu Leu Arg Ala Gly Ser Gly Gly Gly Gly Asp Pro Gly
225                 230                 235                 240

Asp Ala Phe Gly Ile Val Ala Pro Phe Ala Arg Arg Pro Ser Val His
                245                 250                 255

Ser Asp Leu Met Tyr Ile Arg Glu Lys Ala Ser Ala Gly Ser Gln Ala
            260                 265                 270

Lys Asp Lys Glu Arg Cys Val Ile Ser
        275                 280
```

<210> SEQ ID NO 3
<211> LENGTH: 1801
<212> TYPE: DNA
<213> ORGANISM: Homo sapiens
<220> FEATURE:
<221> NAME/KEY: CDS
<222> LOCATION: (154)..(996)

<223> OTHER INFORMATION:

<400> SEQUENCE: 3

| | | |
|---|---|---|
| ggaattccga gcggagccgg agccccaagc ccgagccgcg cccagcccga gcagagcccc | | 60 |
| ccagccgctc acccgcgtg ccaccccagc gaccctcagc cgctctctgc ccttctctcg | | 120 |
| gccccgcgcc cgccctcgcg gccccctctgc cca atg aaa ctg gcc gcg atg atc<br>                                                              Met Lys Leu Ala Ala Met Ile<br>                                                                 1           5 | | 174 |
| aag aag atg tgc ccg agc gac tcg gag ctg agt atc ccg gcc aag aac<br>Lys Lys Met Cys Pro Ser Asp Ser Glu Leu Ser Ile Pro Ala Lys Asn<br>        10                         15                         20 | | 222 |
| tgc tat cgc atg gtc atc ctc ggc tcg tcc aag gtg ggc aag acg gcc<br>Cys Tyr Arg Met Val Ile Leu Gly Ser Ser Lys Val Gly Lys Thr Ala<br>      25                           30                         35 | | 270 |
| atc gtg tcg cgc ttc ctc acc ggc cgc ttc gag gac gcc tac acg cct<br>Ile Val Ser Arg Phe Leu Thr Gly Arg Phe Glu Asp Ala Tyr Thr Pro<br>40                       45                         50                       55 | | 318 |
| acc atc gag gac ttc cac cgc aag ttc tac tcc atc cgc ggc gag gtc<br>Thr Ile Glu Asp Phe His Arg Lys Phe Tyr Ser Ile Arg Gly Glu Val<br>                     60                         65                        70 | | 366 |
| tac cag ctc gac atc ctc gac acg tcc ggc aac cac ccg ttc ccc gcc<br>Tyr Gln Leu Asp Ile Leu Asp Thr Ser Gly Asn His Pro Phe Pro Ala<br>                75                         80                         85 | | 414 |
| atg cgg cgc ctc tcc atc ctc aca gga gac gtt ttc atc ctg gtg ttc<br>Met Arg Arg Leu Ser Ile Leu Thr Gly Asp Val Phe Ile Leu Val Phe<br>           90                          95                         100 | | 462 |
| agt ctg gac aac cgc gac tcc ttc gag gag gtg cag cgg ctc agg cag<br>Ser Leu Asp Asn Arg Asp Ser Phe Glu Glu Val Gln Arg Leu Arg Gln<br>105                    110                     115 | | 510 |
| cag atc ctc gac acc aag tct tgc ctc aag aac aaa acc aag gag aac<br>Gln Ile Leu Asp Thr Lys Ser Cys Leu Lys Asn Lys Thr Lys Glu Asn<br>120                   125                     130                     135 | | 558 |
| gtg gac gtg ccc ctg gtc atc tgc ggc aac aag ggt gac cgc gac ttc<br>Val Asp Val Pro Leu Val Ile Cys Gly Asn Lys Gly Asp Arg Asp Phe<br>                 140                     145                     150 | | 606 |
| tac cgc gag gtg gac cag cgc gag atc gag cag ctg gtg ggc gac gac<br>Tyr Arg Glu Val Asp Gln Arg Glu Ile Glu Gln Leu Val Gly Asp Asp<br>                   155                     160                     165 | | 654 |
| ccc cag cgc tgc gcc tac ttc gag atc tcg gcc aag aag aac agc agc<br>Pro Gln Arg Cys Ala Tyr Phe Glu Ile Ser Ala Lys Lys Asn Ser Ser<br>              170                     175                     180 | | 702 |
| ctg gac cag atg ttc cgc gcg ctc ttc gcc atg gcc aag ctg ccc agc<br>Leu Asp Gln Met Phe Arg Ala Leu Phe Ala Met Ala Lys Leu Pro Ser<br>185                    190                     195 | | 750 |
| gag atg agc cca gac ctg cac cgc aag gtc tcg gtg cag tac tgc gac<br>Glu Met Ser Pro Asp Leu His Arg Lys Val Ser Val Gln Tyr Cys Asp<br>200                    205                     210                     215 | | 798 |
| gtg ctg cac aag aag gcg ctg cgg aac aag aag ctg ctg cgg gcc ggc<br>Val Leu His Lys Lys Ala Leu Arg Asn Lys Lys Leu Leu Arg Ala Gly<br>                220                     225                     230 | | 846 |
| agc ggc ggc ggc ggc ggc gac ccg ggc gac gcc ttt ggc atc gtg gca<br>Ser Gly Gly Gly Gly Gly Asp Pro Gly Asp Ala Phe Gly Ile Val Ala<br>                   235                     240                     245 | | 894 |
| ccc ttc gcg cgc cgg ccc agc gta cac agc gac ctc atg tac atc cgc<br>Pro Phe Ala Arg Arg Pro Ser Val His Ser Asp Leu Met Tyr Ile Arg<br>             250                     255                     260 | | 942 |
| gag aag gcc agc gcc ggc agc cag gcc aag gac aag gag cgc tgc gtc<br>Glu Lys Ala Ser Ala Gly Ser Gln Ala Lys Asp Lys Glu Arg Cys Val<br>       265                     270                     275 | | 990 |

```
atc agc taggagcccc gccgcgctgg cgacacaacc taaggaggac cttttttgtta    1046
Ile Ser
280 agtcaaatcc aacggcccgg tgcgccccag gccgggagcg cgcgcggact ggcgtctccc   1106 ctcccggcga tccgccccca gcactgggga ggcgccactg aaccgagaag ggacggtcat   1166 ctgctccgga aggaaagaga acgggccaag actgggacta ttccccaccc ccgtcccccc   1226 attgaggccc gccaccccca taactttggg agcgagggcc cagccgaggg tggatttatc   1286 ttctcaaaga cctaagagtg agcgcggggt ggggagggga tgtgaagtta tccagcctct   1346 gctaggcttc aagaaaccgt catgcccgct tgaggtcag gacccacggg gcattatctt    1406 gtctgtgatt ccgggttgct gtgacagccg gtagagcctc tgccctcccg aaactaagcg   1466 ggggggcgtg ggtcaaatca tagccaagtg acttgtttac atgtgagtga aactgcacaa   1526 aggaacacaa aacaaaactt gcactttaac ggtagttccg gtgtcaacat ggacacgaac   1586 aaaaccttac ccaggtgttt atactgtgtg tgtgtgaggt ctttaaagtt attgctttat   1646 ttggttttt aatatacaat aaaataattt aaaatgaaa aaaaaaaaaa aaaaaaaaa     1706 aaaaaaaaa aaaaaaaaa aaaaaaaa aaaaaaaa aagcggccgc tcgagcatgc         1766 atctagaggg ccgcatcatg taattagtta tgaac                              1801
```

<210> SEQ ID NO 4
<211> LENGTH: 281
<212> TYPE: PRT
<213> ORGANISM: Homo sapiens

<400> SEQUENCE: 4

```
Met Lys Leu Ala Ala Met Ile Lys Lys Met Cys Pro Ser Asp Ser Glu
1               5                   10                  15

Leu Ser Ile Pro Ala Lys Asn Cys Tyr Arg Met Val Ile Leu Gly Ser
                20                  25                  30

Ser Lys Val Gly Lys Thr Ala Ile Val Ser Arg Phe Leu Thr Gly Arg
            35                  40                  45

Phe Glu Asp Ala Tyr Thr Pro Thr Ile Glu Asp Phe His Arg Lys Phe
        50                  55                  60

Tyr Ser Ile Arg Gly Glu Val Tyr Gln Leu Asp Ile Leu Asp Thr Ser
65              70                  75                  80

Gly Asn His Pro Phe Pro Ala Met Arg Arg Leu Ser Ile Leu Thr Gly
                85                  90                  95

Asp Val Phe Ile Leu Val Phe Ser Leu Asp Asn Arg Asp Ser Phe Glu
            100                 105                 110

Glu Val Gln Arg Leu Arg Gln Gln Ile Leu Asp Thr Lys Ser Cys Leu
        115                 120                 125

Lys Asn Lys Thr Lys Glu Asn Val Asp Val Pro Leu Val Ile Cys Gly
    130                 135                 140

Asn Lys Gly Asp Arg Asp Phe Tyr Arg Glu Val Asp Gln Arg Glu Ile
145             150                 155                 160

Glu Gln Leu Val Gly Asp Asp Pro Gln Arg Cys Ala Tyr Phe Glu Ile
                165                 170                 175

Ser Ala Lys Lys Asn Ser Ser Leu Asp Gln Met Phe Arg Ala Leu Phe
            180                 185                 190

Ala Met Ala Lys Leu Pro Ser Glu Met Ser Pro Asp Leu His Arg Lys
        195                 200                 205

Val Ser Val Gln Tyr Cys Asp Val Leu His Lys Lys Ala Leu Arg Asn
```

```
                210              215              220
Lys Lys Leu Leu Arg Ala Gly Ser Gly Gly Gly Gly Asp Pro Gly
225                 230                 235                 240

Asp Ala Phe Gly Ile Val Ala Pro Phe Ala Arg Arg Pro Ser Val His
                245                 250                 255

Ser Asp Leu Met Tyr Ile Arg Glu Lys Ala Ser Ala Gly Ser Gln Ala
            260                 265                 270

Lys Asp Lys Glu Arg Cys Val Ile Ser
        275                 280

<210> SEQ ID NO 5
<211> LENGTH: 54
<212> TYPE: DNA
<213> ORGANISM: Artificial sequence
<220> FEATURE:
<223> OTHER INFORMATION: Probe/Primer

<400> SEQUENCE: 5
ctgctggtcg acgcggccgc tcatataata ccaattttttt taaggttttg ctgg         54

<210> SEQ ID NO 6
<211> LENGTH: 28
<212> TYPE: DNA
<213> ORGANISM: Artificial sequence
<220> FEATURE:
<223> OTHER INFORMATION: Probe/Primer

<400> SEQUENCE: 6
gtttgatgtg ggtgctcagc ggtctgag                                       28

<210> SEQ ID NO 7
<211> LENGTH: 29
<212> TYPE: DNA
<213> ORGANISM: Artificial sequence
<220> FEATURE:
<223> OTHER INFORMATION: Probe/Primer

<400> SEQUENCE: 7
ctcagaaccg ctgagcaccc acatcaaac                                      29

<210> SEQ ID NO 8
<211> LENGTH: 35
<212> TYPE: DNA
<213> ORGANISM: Artificial sequence
<220> FEATURE:
<223> OTHER INFORMATION: Probe/Primer

<400> SEQUENCE: 8
cgggatccat gaaactggcc gcgatgatca agaag                               35

<210> SEQ ID NO 9
<211> LENGTH: 28
<212> TYPE: DNA
<213> ORGANISM: Artificial sequence
<220> FEATURE:
<223> OTHER INFORMATION: Prober/Primer

<400> SEQUENCE: 9
ggaattccta gctgatgacg cagcgctc                                       28

<210> SEQ ID NO 10
<211> LENGTH: 25
<212> TYPE: DNA
<213> ORGANISM: Artificial sequence
```

```
<220> FEATURE:
<223> OTHER INFORMATION: Probe/Primer

<400> SEQUENCE: 10
ggatccatgc aaacgctaaa gtgtg                                              25

<210> SEQ ID NO 11
<211> LENGTH: 31
<212> TYPE: DNA
<213> ORGANISM: Artificial sequence
<220> FEATURE:
<223> OTHER INFORMATION: Probe/Primer

<400> SEQUENCE: 11
gaattcgact acaaaattgc acatttttta c                                       31

<210> SEQ ID NO 12
<211> LENGTH: 31
<212> TYPE: DNA
<213> ORGANISM: Artificial sequence
<220> FEATURE:
<223> OTHER INFORMATION: Probe/Primer

<400> SEQUENCE: 12
cgcatggtca tcctcgtttc gtccaaggtg g                                       31

<210> SEQ ID NO 13
<211> LENGTH: 31
<212> TYPE: DNA
<213> ORGANISM: Artificial sequence
<220> FEATURE:
<223> OTHER INFORMATION: Probe/Primer

<400> SEQUENCE: 13
ccaccttgga cgaaacgagg atgaccatgc g                                       31

<210> SEQ ID NO 14
<211> LENGTH: 35
<212> TYPE: DNA
<213> ORGANISM: Artificial sequence
<220> FEATURE:
<223> OTHER INFORMATION: Probe/Primer

<400> SEQUENCE: 14
gctcgtccaa ggtggttaag acggccatcg tgtcg                                   35

<210> SEQ ID NO 15
<211> LENGTH: 35
<212> TYPE: DNA
<213> ORGANISM: Artificial sequence
<220> FEATURE:
<223> OTHER INFORMATION: Probe/Primer

<400> SEQUENCE: 15
cgacacgatg gccgtcttaa ccaccttgga cgagc                                   35

<210> SEQ ID NO 16
<211> LENGTH: 32
<212> TYPE: DNA
<213> ORGANISM: Artificial sequence
<220> FEATURE:
<223> OTHER INFORMATION: Probe/Primwer

<400> SEQUENCE: 16
cctcgacacg tccgctaacc acccgttccc cg                                      32
```

```
<210> SEQ ID NO 17
<211> LENGTH: 32
<212> TYPE: DNA
<213> ORGANISM: Artificial sequence
<220> FEATURE:
<223> OTHER INFORMATION: Probe/Primer

<400> SEQUENCE: 17
cggggaacgg gtggttagcg gacgtgtcga gg                                         32

<210> SEQ ID NO 18
<211> LENGTH: 8
<212> TYPE: PRT
<213> ORGANISM: Unknown
<220> FEATURE:
<223> OTHER INFORMATION: The phosphate/magnesium binding region
      GXXXXGK(S/T)
<220> FEATURE:
<221> NAME/KEY: MISC_FEATURE
<222> LOCATION: (2)..(5)
<223> OTHER INFORMATION: Xaa's at positions 2-5 may be any amino acid
<220> FEATURE:
<221> NAME/KEY: MISC_FEATURE
<222> LOCATION: (8)..(8)
<223> OTHER INFORMATION: Xaa at position 8 may be Serine or Threonine
      acid

<400> SEQUENCE: 18

Gly Xaa Xaa Xaa Xaa Gly Lys Xaa
1               5

<210> SEQ ID NO 19
<211> LENGTH: 4
<212> TYPE: PRT
<213> ORGANISM: Unknown
<220> FEATURE:
<223> OTHER INFORMATION: The phospate/magnesium binding region DXXG
<220> FEATURE:
<221> NAME/KEY: misc_feature
<222> LOCATION: (2)..(3)
<223> OTHER INFORMATION: Xaa's at positions 2, 3 may be any amino acid

<400> SEQUENCE: 19

Asp Xaa Xaa Gly
1

<210> SEQ ID NO 20
<211> LENGTH: 4
<212> TYPE: PRT
<213> ORGANISM: Unknown
<220> FEATURE:
<223> OTHER INFORMATION: The guanine base binding loop NKXD
<220> FEATURE:
<221> NAME/KEY: MISC_FEATURE
<222> LOCATION: (3)..(3)
<223> OTHER INFORMATION: Xaa at position 3 may be any amino acid

<400> SEQUENCE: 20

Asn Lys Xaa Asp
1

<210> SEQ ID NO 21
<211> LENGTH: 5
<212> TYPE: PRT
<213> ORGANISM: Unknown
<220> FEATURE:
<223> OTHER INFORMATION: The guanine base binding lopp EXSAK
<220> FEATURE:
<221> NAME/KEY: MISC_FEATURE
<222> LOCATION: (2)..(2)
```

<223> OTHER INFORMATION: Xaa at position 2 may be any amino acid

<400> SEQUENCE: 21

Glu Xaa Ser Ala Lys
1               5

<210> SEQ ID NO 22
<211> LENGTH: 4
<212> TYPE: PRT
<213> ORGANISM: Unknown
<220> FEATURE:
<223> OTHER INFORMATION: The C-terminal CAAX
<220> FEATURE:
<221> NAME/KEY: MISC_FEATURE
<222> LOCATION: (2)..(3)
<223> OTHER INFORMATION: Xaa at position 2 or 3 may be any aliphatic
      amino acid residue
<220> FEATURE:
<221> NAME/KEY: MISC_FEATURE
<222> LOCATION: (4)..(4)
<223> OTHER INFORMATION: Xaa at position 4 may be any amino acid

<400> SEQUENCE: 22

Cys Xaa Xaa Xaa
1

<210> SEQ ID NO 23
<211> LENGTH: 7
<212> TYPE: PRT
<213> ORGANISM: Homo sapiens

<400> SEQUENCE: 23

Gln Ala Lys Asp Lys Glu Arg
1               5

<210> SEQ ID NO 24
<211> LENGTH: 1691
<212> TYPE: DNA
<213> ORGANISM: Homo sapiens
<220> FEATURE:
<221> NAME/KEY: CDS
<222> LOCATION: (45)..(587)
<223> OTHER INFORMATION:

<400> SEQUENCE: 24

```
taagaagttg tacttaaagc ggaggagcta agccacctgc caaa atg tgc aaa gga      56
                                              Met Cys Lys Gly
                                                1 ctt gca gct ttg ccc cac tca tgc ctg gaa agg gcc aag gag att aag     104
Leu Ala Ala Leu Pro His Ser Cys Leu Glu Arg Ala Lys Glu Ile Lys
 5              10                  15                  20 atc aag ttg gga att ctc ctc cag aag cca gac tca gtt ggt gac ctt     152
Ile Lys Leu Gly Ile Leu Leu Gln Lys Pro Asp Ser Val Gly Asp Leu
                25                  30                  35 gtc att ccg tac aat gag aag cca gag aaa cca gcc aag acc cag aaa     200
Val Ile Pro Tyr Asn Glu Lys Pro Glu Lys Pro Ala Lys Thr Gln Lys
            40                  45                  50 acc tcg ctg gac gag gcc ctg cag tgg cgt gat tcc ctg gac aaa ctc     248
Thr Ser Leu Asp Glu Ala Leu Gln Trp Arg Asp Ser Leu Asp Lys Leu
        55                  60                  65 ctg cag aac aac tat gga ctt gcc agt ttc aaa agt ttc ctg aag tct     296
Leu Gln Asn Asn Tyr Gly Leu Ala Ser Phe Lys Ser Phe Leu Lys Ser
    70                  75                  80 gaa ttc agt gag gaa aac ctt gag ttc tgg att gcc tgt gag gat tac     344
Glu Phe Ser Glu Glu Asn Leu Glu Phe Trp Ile Ala Cys Glu Asp Tyr
85                  90                  95                 100
```

```
aag aag atc aag tcc cct gcc aag atg gct gag aag gca aag caa att       392
Lys Lys Ile Lys Ser Pro Ala Lys Met Ala Glu Lys Ala Lys Gln Ile
            105                 110                 115 tat gaa gaa ttc att caa acg gag gct cct aaa gag gtg aat att gac       440
Tyr Glu Glu Phe Ile Gln Thr Glu Ala Pro Lys Glu Val Asn Ile Asp
        120                 125                 130 cac ttc act aag gac atc aca atg aag aac ctg gtg gaa cct tcc ctg       488
His Phe Thr Lys Asp Ile Thr Met Lys Asn Leu Val Glu Pro Ser Leu
            135                 140                 145 agc agc ttt gac atg gcc cag aaa aga atc cat gcc ctg atg gaa aag       536
Ser Ser Phe Asp Met Ala Gln Lys Arg Ile His Ala Leu Met Glu Lys
        150                 155                 160 gat tct ctg cct cgc ttt gtg cgc tct gag ttt tat cag gag tta atc       584
Asp Ser Leu Pro Arg Phe Val Arg Ser Glu Phe Tyr Gln Glu Leu Ile
165                 170                 175                 180 aag tagtaattta gccaggctat gaaatcatcc tgtgagttat ttcctccata            637
Lys ataaccctgc atttcccatt aatctacata tcttcccaca gcagctttgc tcagtgatac     697
ccacatggga aaaatcccag gggatgttgc ttactctttt tgcccacact gctttggata     757
cttatctact gtccgaaggc cttctttccc cactcaattc ttcctgccct gttattaatt     817
aagatatctt cagcttgtag tcagacccaa tcagaatcac agaaaatcc tgcctaaggc      877 aaagaaatat aagacaagac tatgatatca atgaatgtgg gttaagtaat agatttccag     937
ctaaattggt ctaaaaaaga atattaagtg tggacagacc tatttcaaag gagcttaatt     997
gatctcactt gttttagttc tgatccaggg agatcacccc tctaattatt tctgaacttg    1057
gttaataaaa gttataaga ttttatgaa gcagccactg tatgatattt taagcaaata     1117
tgttatttaa atattgatc cttcccttgg accaccttca tgttagttgg gtattataaa     1177
taagagatac aaccatgaat atattatgtt tatacaaaat caatctgaac acaattcata    1237
aagatttctc ttttatacct tcctcactgg cccctccac ctgcccatag tcaccaaatt     1297
ctgttttaaa tcaatgacct aagatcaaca atgaagtatt ttataaatgt atttatgctg    1357
ctagactgtg ggtcaaatgt ttccattttc aaattattta gaattcttat gagtttaaaa    1417
tttgtaaatt tctaaatcca atcatgtaaa atgaaactgt tgctccattg gagtagtctc    1477
ccacctaaat atcaagatgg ctatatgcta aaaagagaaa atatggtcaa gtctaaaatg    1537
gctaattgtc ctatgatgct attatcatag actaatgaca tttatcttca aaacaccaaa    1597
ttgtctttag aaaaattaat gtgattacag gtagaggcct tctaggtgag acactttttaa   1657 ggtacactgc attttgcaaa aaaaaaaaaa aaaa                                1691
```

<210> SEQ ID NO 25
<211> LENGTH: 181
<212> TYPE: PRT
<213> ORGANISM: Homo sapiens

<400> SEQUENCE: 25

```
Met Cys Lys Gly Leu Ala Ala Leu Pro His Ser Cys Leu Glu Arg Ala
1               5                   10                  15

Lys Glu Ile Lys Ile Lys Leu Gly Ile Leu Leu Gln Lys Pro Asp Ser
            20                  25                  30

Val Gly Asp Leu Val Ile Pro Tyr Asn Glu Lys Pro Glu Lys Pro Ala
        35                  40                  45

Lys Thr Gln Lys Thr Ser Leu Asp Glu Ala Leu Gln Trp Arg Asp Ser
    50                  55                  60
```

Leu Asp Lys Leu Leu Gln Asn Asn Tyr Gly Leu Ala Ser Phe Lys Ser
65                  70                  75                  80

Phe Leu Lys Ser Glu Phe Ser Glu Glu Asn Leu Glu Phe Trp Ile Ala
                85                  90                  95

Cys Glu Asp Tyr Lys Lys Ile Lys Ser Pro Ala Lys Met Ala Glu Lys
                100                 105                 110

Ala Lys Gln Ile Tyr Glu Glu Phe Ile Gln Thr Glu Ala Pro Lys Glu
                115                 120                 125

Val Asn Ile Asp His Phe Thr Lys Asp Ile Thr Met Lys Asn Leu Val
        130                 135                 140

Glu Pro Ser Leu Ser Ser Phe Asp Met Ala Gln Lys Arg Ile His Ala
145                 150                 155                 160

Leu Met Glu Lys Asp Ser Leu Pro Arg Phe Val Arg Ser Glu Phe Tyr
                165                 170                 175

Gln Glu Leu Ile Lys
            180

<210> SEQ ID NO 26
<211> LENGTH: 27
<212> TYPE: DNA
<213> ORGANISM: Artificial sequence
<220> FEATURE:
<223> OTHER INFORMATION: Probe/Primer

<400> SEQUENCE: 26
ccagatctaa agatgccgat ttgggcg                                     27

<210> SEQ ID NO 27
<211> LENGTH: 32
<212> TYPE: DNA
<213> ORGANISM: Artificial sequence
<220> FEATURE:
<223> OTHER INFORMATION: Probe/Primer

<400> SEQUENCE: 27
ccccatggtt ttatatttgt tgtaaaaagt ag                               32

<210> SEQ ID NO 28
<211> LENGTH: 30
<212> TYPE: DNA
<213> ORGANISM: Artificial sequence
<220> FEATURE:
<223> OTHER INFORMATION: Probe/Primer

<400> SEQUENCE: 28
cgggatccat gtgcaaaggg cttgcaggtc                                  30

<210> SEQ ID NO 29
<211> LENGTH: 28
<212> TYPE: DNA
<213> ORGANISM: Artificial sequence
<220> FEATURE:
<223> OTHER INFORMATION: Probe/Primer

<400> SEQUENCE: 29
ccgctcgagt taggcacact gagggacc                                    28

<210> SEQ ID NO 30
<211> LENGTH: 41
<212> TYPE: DNA
<213> ORGANISM: Homo sapiens

```
<400> SEQUENCE: 30
agtcggtacc cgcatagatc tgcaggatgc ccttttttgac g                    41

<210> SEQ ID NO 31
<211> LENGTH: 34
<212> TYPE: DNA
<213> ORGANISM: Artificial sequence
<220> FEATURE:
<223> OTHER INFORMATION: Probe/Primer

<400> SEQUENCE: 31
gtacgtcgac tttgattttc agaaacttga tggc                             34

<210> SEQ ID NO 32
<211> LENGTH: 32
<212> TYPE: DNA
<213> ORGANISM: Artificial sequence
<220> FEATURE:
<223> OTHER INFORMATION: Probe/Primer

<400> SEQUENCE: 32
tggcctcgag atgacaaatt caaaagaaga cg                               32

<210> SEQ ID NO 33
<211> LENGTH: 32
<212> TYPE: DNA
<213> ORGANISM: Artificial sequence
<220> FEATURE:
<223> OTHER INFORMATION: Probe/Primer

<400> SEQUENCE: 33
atcactgcag ctatgctaca acattccaaa at                               32

<210> SEQ ID NO 34
<211> LENGTH: 32
<212> TYPE: DNA
<213> ORGANISM: Artificial sequence
<220> FEATURE:
<223> OTHER INFORMATION: Probe/Primer

<400> SEQUENCE: 34
gggtcatgaa actggccgcg atgatcaaga ag                               32

<210> SEQ ID NO 35
<211> LENGTH: 31
<212> TYPE: DNA
<213> ORGANISM: Artificial sequence
<220> FEATURE:
<223> OTHER INFORMATION: Probe/Primer

<400> SEQUENCE: 35
gatagtcgac ctagctgatg acgcagcgct c                                31

<210> SEQ ID NO 36
<211> LENGTH: 31
<212> TYPE: DNA
<213> ORGANISM: Artificial sequence
<220> FEATURE:
<223> OTHER INFORMATION: Probe/Primer

<400> SEQUENCE: 36
cgcatggtca tcctcgtttc gtccaaggtg g                                31

<210> SEQ ID NO 37
<211> LENGTH: 31
```

```
<212> TYPE: DNA
<213> ORGANISM: Artificial sequence
<220> FEATURE:
<223> OTHER INFORMATION: Probe/Primer

<400> SEQUENCE: 37
ccaccttgga cgaaacgagg atgaccatgc g                           31

<210> SEQ ID NO 38
<211> LENGTH: 32
<212> TYPE: DNA
<213> ORGANISM: Artificial sequence
<220> FEATURE:
<223> OTHER INFORMATION: Probe/Primer

<400> SEQUENCE: 38
ccaaggacaa ggagcgcagc gtcatcagct ag                          32

<210> SEQ ID NO 39
<211> LENGTH: 32
<212> TYPE: DNA
<213> ORGANISM: Artificial sequence
<220> FEATURE:
<223> OTHER INFORMATION: Probe/Primer

<400> SEQUENCE: 39
ctagctgatg acgctgcgct ccttgtcctt gg                          32

<210> SEQ ID NO 40
<211> LENGTH: 837
<212> TYPE: DNA
<213> ORGANISM: Homo sapiens
<220> FEATURE:
<221> NAME/KEY: CDS
<222> LOCATION: (1)..(834)
<223> OTHER INFORMATION:

<400> SEQUENCE: 40 atg cct gct tct ctc gct ttg ttg cag ccc cga gcc atg atg aag act    48
Met Pro Ala Ser Leu Ala Leu Leu Gln Pro Arg Ala Met Met Lys Thr
 1               5                  10                  15 ttg tcc agc ggg aac tgc acg ctc agt gtg ccc gcc aaa aac tca tac    96
Leu Ser Ser Gly Asn Cys Thr Leu Ser Val Pro Ala Lys Asn Ser Tyr
             20                  25                  30 cgc atg gtg gtg ctg ggt gcc tct cgg gtg ggc aag agc tcc atc gtg   144
Arg Met Val Val Leu Gly Ala Ser Arg Val Gly Lys Ser Ser Ile Val
         35                  40                  45 tct cgc ttc ctc aat ggc cgc ttt gag gac cag tac aca ccc acc atc   192
Ser Arg Phe Leu Asn Gly Arg Phe Glu Asp Gln Tyr Thr Pro Thr Ile
     50                  55                  60 gag gac ttc cac cgt aag gta tac aac atc cgc ggc gac atg tac cag   240
Glu Asp Phe His Arg Lys Val Tyr Asn Ile Arg Gly Asp Met Tyr Gln
 65                  70                  75                  80 ctc gac atc ctg gat acc tct ggc aac cac ccc ttc ccc gcc atg cgc   288
Leu Asp Ile Leu Asp Thr Ser Gly Asn His Pro Phe Pro Ala Met Arg
                 85                  90                  95 agg ctg tcc atc ctc aca ggg gat gtc ttc atc ctg gtg ttc agc ctg   336
Arg Leu Ser Ile Leu Thr Gly Asp Val Phe Ile Leu Val Phe Ser Leu
            100                 105                 110 gat aac cgg gag tcc ttc gat gag gtc aag cgc ctt cag aag cag atc   384
Asp Asn Arg Glu Ser Phe Asp Glu Val Lys Arg Leu Gln Lys Gln Ile
        115                 120                 125 ctg gag gtc aag tcc tgc ctg aag aac aag acc aag gag gcg gcg gag   432
Leu Glu Val Lys Ser Cys Leu Lys Asn Lys Thr Lys Glu Ala Ala Glu
```

```
        130                 135                 140
ctg ccc atg gtc atc tgt ggc aac aag aac gac cac ggc gag ctg tgc         480
Leu Pro Met Val Ile Cys Gly Asn Lys Asn Asp His Gly Glu Leu Cys
145                 150                 155                 160 cgc cag gtg ccc acc acc gag gcc gag ctg ctg gtg tcg ggc gac gag         528
Arg Gln Val Pro Thr Thr Glu Ala Glu Leu Leu Val Ser Gly Asp Glu
                165                 170                 175 aac tgc gcc tac ttc gag gtg tcg gcc aag aag aac acc aac gtg gac         576
Asn Cys Ala Tyr Phe Glu Val Ser Ala Lys Lys Asn Thr Asn Val Asp
            180                 185                 190 gag atg ttc tac gtg ctc ttc agc atg gcc aag ctg cca cac gag atg         624
Glu Met Phe Tyr Val Leu Phe Ser Met Ala Lys Leu Pro His Glu Met
        195                 200                 205 agc ccc gcc ctg cat cgc aag atc tcc gtg cag tac ggt gac gcc ttc         672
Ser Pro Ala Leu His Arg Lys Ile Ser Val Gln Tyr Gly Asp Ala Phe
    210                 215                 220 cac ccc agg ccc ttc tgc atg cgc cgc gtc aag gag atg gac gcc tat         720
His Pro Arg Pro Phe Cys Met Arg Arg Val Lys Glu Met Asp Ala Tyr
225                 230                 235                 240 ggc atg gtc tcg ccc ttc gcc cgc cgc ccc agc gtc aac agt gac ctc         768
Gly Met Val Ser Pro Phe Ala Arg Arg Pro Ser Val Asn Ser Asp Leu
                245                 250                 255 aag tac atc aag gcc aag gtc ctt cgg gaa ggc cag gcc cgt gag agg         816
Lys Tyr Ile Lys Ala Lys Val Leu Arg Glu Gly Gln Ala Arg Glu Arg
            260                 265                 270 gac aag tgc acc atc cag tga                                             837
Asp Lys Cys Thr Ile Gln
            275

<210> SEQ ID NO 41
<211> LENGTH: 278
<212> TYPE: PRT
<213> ORGANISM: Homo sapiens

<400> SEQUENCE: 41

Met Pro Ala Ser Leu Ala Leu Leu Gln Pro Arg Ala Met Met Lys Thr
1               5                   10                  15

Leu Ser Ser Gly Asn Cys Thr Leu Ser Val Pro Ala Lys Asn Ser Tyr
            20                  25                  30

Arg Met Val Val Leu Gly Ala Ser Arg Val Gly Lys Ser Ser Ile Val
        35                  40                  45

Ser Arg Phe Leu Asn Gly Arg Phe Glu Asp Gln Tyr Thr Pro Thr Ile
    50                  55                  60

Glu Asp Phe His Arg Lys Val Tyr Asn Ile Arg Gly Asp Met Tyr Gln
65                  70                  75                  80

Leu Asp Ile Leu Asp Thr Ser Gly Asn His Pro Phe Pro Ala Met Arg
                85                  90                  95

Arg Leu Ser Ile Leu Thr Gly Asp Val Phe Ile Leu Val Phe Ser Leu
            100                 105                 110

Asp Asn Arg Glu Ser Phe Asp Glu Val Lys Arg Leu Gln Lys Gln Ile
        115                 120                 125

Leu Glu Val Lys Ser Cys Leu Lys Asn Lys Thr Lys Glu Ala Ala Glu
130                 135                 140

Leu Pro Met Val Ile Cys Gly Asn Lys Asn Asp His Gly Glu Leu Cys
145                 150                 155                 160

Arg Gln Val Pro Thr Thr Glu Ala Glu Leu Leu Val Ser Gly Asp Glu
                165                 170                 175
```

```
Asn Cys Ala Tyr Phe Glu Val Ser Ala Lys Lys Asn Thr Asn Val Asp
            180                 185                 190

Glu Met Phe Tyr Val Leu Phe Ser Met Ala Lys Leu Pro His Glu Met
        195                 200                 205

Ser Pro Ala Leu His Arg Lys Ile Ser Val Gln Tyr Gly Asp Ala Phe
    210                 215                 220

His Pro Arg Pro Phe Cys Met Arg Arg Val Lys Glu Met Asp Ala Tyr
225                 230                 235                 240

Gly Met Val Ser Pro Phe Ala Arg Arg Pro Ser Val Asn Ser Asp Leu
                245                 250                 255

Lys Tyr Ile Lys Ala Lys Val Leu Arg Glu Gly Gln Ala Arg Glu Arg
            260                 265                 270

Asp Lys Cys Thr Ile Gln
            275

<210> SEQ ID NO 42
<211> LENGTH: 15
<212> TYPE: PRT
<213> ORGANISM: Homo sapiens

<400> SEQUENCE: 42

Asp Thr Lys Ser Cys Leu Lys Asn Lys Thr Lys Glu Asn Val Asp
1               5                   10                  15

<210> SEQ ID NO 43
<211> LENGTH: 19
<212> TYPE: DNA
<213> ORGANISM: Artificial sequence
<220> FEATURE:
<223> OTHER INFORMATION: Probe/Primer

<400> SEQUENCE: 43
ttctcgcgga tgtacatga                                              19

<210> SEQ ID NO 44
<211> LENGTH: 20
<212> TYPE: DNA
<213> ORGANISM: Artificial sequence
<220> FEATURE:
<223> OTHER INFORMATION: Probe/Primer

<400> SEQUENCE: 44
tccaccgcaa gttctactcc                                             20

<210> SEQ ID NO 45
<211> LENGTH: 1740
<212> TYPE: DNA
<213> ORGANISM: Homo sapiens
<220> FEATURE:
<221> NAME/KEY: CDS
<222> LOCATION: (146)..(988)
<223> OTHER INFORMATION:

<400> SEQUENCE: 45
gagcggagcc ggagccccaa gcccgagccg cgcccagccc gagcagagcc ctccagccgc     60 tcacccgcg tgccacccca gcgaccctca gccgctctct gcccttctct cggccccgcg    120
cccgccctcg cggcccctct gccca atg aaa ctg gcc gcg atg atc aag aag    172
                           Met Lys Leu Ala Ala Met Ile Lys Lys
                             1               5 atg tgc ccg agc gac tcg gag ctg agt atc ccg gcc aag aac tgc tat    220
Met Cys Pro Ser Asp Ser Glu Leu Ser Ile Pro Ala Lys Asn Cys Tyr
 10              15                  20                  25
```

| | | | | | | | | | | | | | | | | |
|---|---|---|---|---|---|---|---|---|---|---|---|---|---|---|---|---|
| cgc | atg | gtc | atc | ctc | ggc | tcg | tcc | aag | gtg | ggc | aag | acg | gcc | atc | gtg | 268 |
| Arg | Met | Val | Ile | Leu | Gly | Ser | Ser | Lys | Val | Gly | Lys | Thr | Ala | Ile | Val | |
| | | | | 30 | | | | 35 | | | | | 40 | | | |
| tcg | cgc | ttc | ctc | acc | ggc | cgc | ttc | gag | gac | gcc | tac | acg | cct | acc | atc | 316 |
| Ser | Arg | Phe | Leu | Thr | Gly | Arg | Phe | Glu | Asp | Ala | Tyr | Thr | Pro | Thr | Ile | |
| | | | 45 | | | | 50 | | | | | 55 | | | | |
| gag | gac | ttc | cac | cgc | aag | ttc | tac | tcc | atc | cgc | ggc | gag | gtc | tac | cag | 364 |
| Glu | Asp | Phe | His | Arg | Lys | Phe | Tyr | Ser | Ile | Arg | Gly | Glu | Val | Tyr | Gln | |
| | | | 60 | | | | | 65 | | | | 70 | | | | |
| ctc | gac | atc | ctc | gac | acg | tcc | ggc | aac | cac | ccg | ttc | ccc | gcc | atg | cgg | 412 |
| Leu | Asp | Ile | Leu | Asp | Thr | Ser | Gly | Asn | His | Pro | Phe | Pro | Ala | Met | Arg | |
| | 75 | | | | | 80 | | | | | 85 | | | | | |
| cgc | ctc | tcc | atc | ctc | aca | gga | gac | gtt | ttc | atc | ctg | gtg | ttc | agt | ctg | 460 |
| Arg | Leu | Ser | Ile | Leu | Thr | Gly | Asp | Val | Phe | Ile | Leu | Val | Phe | Ser | Leu | |
| 90 | | | | | 95 | | | | | 100 | | | | | 105 | |
| gac | aac | cgc | gac | tcc | ttc | gag | gag | gtg | cag | cgg | ctc | agg | cag | cag | atc | 508 |
| Asp | Asn | Arg | Asp | Ser | Phe | Glu | Glu | Val | Gln | Arg | Leu | Arg | Gln | Gln | Ile | |
| | | | | 110 | | | | | 115 | | | | | 120 | | |
| ctc | gac | acc | aag | tct | tgc | ctc | aag | aac | aaa | acc | aag | gag | aac | gtg | gac | 556 |
| Leu | Asp | Thr | Lys | Ser | Cys | Leu | Lys | Asn | Lys | Thr | Lys | Glu | Asn | Val | Asp | |
| | | | 125 | | | | | 130 | | | | | 135 | | | |
| gtg | ccc | ctg | gtc | atc | tgc | ggc | aac | aag | ggt | gac | cgc | gac | ttc | tac | cgc | 604 |
| Val | Pro | Leu | Val | Ile | Cys | Gly | Asn | Lys | Gly | Asp | Arg | Asp | Phe | Tyr | Arg | |
| | | | 140 | | | | | 145 | | | | | 150 | | | |
| gag | gtg | gac | cag | cgc | gag | atc | gag | cag | ctg | gtg | ggc | gac | gac | ccc | cag | 652 |
| Glu | Val | Asp | Gln | Arg | Glu | Ile | Glu | Gln | Leu | Val | Gly | Asp | Asp | Pro | Gln | |
| | | 155 | | | | | 160 | | | | | 165 | | | | |
| cgc | tgc | gcc | tac | ttc | gag | atc | tcg | gcc | aag | aag | aac | agc | agc | ctg | gac | 700 |
| Arg | Cys | Ala | Tyr | Phe | Glu | Ile | Ser | Ala | Lys | Lys | Asn | Ser | Ser | Leu | Asp | |
| 170 | | | | | 175 | | | | | 180 | | | | | 185 | |
| cag | atg | ttc | cgc | gcg | ctc | ttc | gcc | atg | gcc | aag | ctg | ccc | agc | gag | atg | 748 |
| Gln | Met | Phe | Arg | Ala | Leu | Phe | Ala | Met | Ala | Lys | Leu | Pro | Ser | Glu | Met | |
| | | | | 190 | | | | | 195 | | | | | 200 | | |
| agc | cca | gac | ctg | cac | cgc | aag | gtc | tcg | gtg | cag | tac | tgc | gac | gtg | ctg | 796 |
| Ser | Pro | Asp | Leu | His | Arg | Lys | Val | Ser | Val | Gln | Tyr | Cys | Asp | Val | Leu | |
| | | | 205 | | | | | 210 | | | | | 215 | | | |
| cac | aag | aag | gcg | ctg | cgg | aac | aag | aag | ctg | ctg | cgg | gcc | ggc | agc | ggc | 844 |
| His | Lys | Lys | Ala | Leu | Arg | Asn | Lys | Lys | Leu | Leu | Arg | Ala | Gly | Ser | Gly | |
| | | 220 | | | | | 225 | | | | | 230 | | | | |
| ggc | ggc | ggc | ggc | gac | ccg | ggc | gac | gcc | ttt | ggc | atc | gtg | gca | ccc | ttc | 892 |
| Gly | Gly | Gly | Gly | Asp | Pro | Gly | Asp | Ala | Phe | Gly | Ile | Val | Ala | Pro | Phe | |
| | 235 | | | | | 240 | | | | | 245 | | | | | |
| gcg | cgc | cgg | ccc | agc | gta | cac | agc | gac | ctc | atg | tac | atc | cgc | gag | aag | 940 |
| Ala | Arg | Arg | Pro | Ser | Val | His | Ser | Asp | Leu | Met | Tyr | Ile | Arg | Glu | Lys | |
| 250 | | | | | 255 | | | | | 260 | | | | | 265 | |
| gcc | agc | gcc | ggc | agc | cag | gcc | aag | gac | aag | gag | cgc | tgc | gtc | atc | agc | 988 |
| Ala | Ser | Ala | Gly | Ser | Gln | Ala | Lys | Asp | Lys | Glu | Arg | Cys | Val | Ile | Ser | |
| | | | | 270 | | | | | 275 | | | | | 280 | | |

| | |
|---|---|
| taggagcccc gccgcgctgg cgacacaacc taaggaggac cttttgtta agtcaaatcc | 1048 |
| aacggcccgg tgcgccccag gccgggagcg cgcgcggact ggcgtctccc ctcccggcga | 1108 |
| tccgccccca gcactgggga ggcgccactg aaccgagaag ggacggtcat ctgctccgga | 1168 |
| aggaaagaga acgggccaag actgggacta ttccccaccc ccgtccccc attgaggccc | 1228 |
| gccaccccca taactttggg agcgagggcc cagccgaggg tggatttatc ttctcaaaga | 1288 |
| cctaagagtg agcgcggggt gggggaggga tgtgaagtta ccagcctct gctaggcttc | 1348 |
| aagaaaccgt catgcccgct tgagggtcag gacccacggg gcattatctt gtctgtgatt | 1408 |

```
ccgggttgct gtgacagccg gtagagcctc tgccctcccg aaactaagcg gggggcgtg    1468 ggtcaaatca tagccaagtg acttgtttac atgtgagtga aactgcacaa aggaacacaa    1528
aacaaaactt gcactttaac ggtagttccg gtgtcaacat ggacacgaac aaaaccttac    1588
ccaggtgttt atactgtgtg tgtgtgaggt ctttaaagtt attgctttat ttggtttttt    1648
aatatacaat aaaataattt aaaatggaaa aaaaaaaaaa aaaaaaaaaa aaaaaaaaa    1708 aaaaaaaaaa aaaaaaaaa aaaaaaaaa aa                                   1740

<210> SEQ ID NO 46
<211> LENGTH: 281
<212> TYPE: PRT
<213> ORGANISM: Homo sapiens

<400> SEQUENCE: 46

Met Lys Leu Ala Ala Met Ile Lys Lys Met Cys Pro Ser Asp Ser Glu
1               5                   10                  15

Leu Ser Ile Pro Ala Lys Asn Cys Tyr Arg Met Val Ile Leu Gly Ser
            20                  25                  30

Ser Lys Val Gly Lys Thr Ala Ile Val Ser Arg Phe Leu Thr Gly Arg
        35                  40                  45

Phe Glu Asp Ala Tyr Thr Pro Thr Ile Glu Asp Phe His Arg Lys Phe
    50                  55                  60

Tyr Ser Ile Arg Gly Glu Val Tyr Gln Leu Asp Ile Leu Asp Thr Ser
65                  70                  75                  80

Gly Asn His Pro Phe Pro Ala Met Arg Arg Leu Ser Ile Leu Thr Gly
                85                  90                  95

Asp Val Phe Ile Leu Val Phe Ser Leu Asp Asn Arg Asp Ser Phe Glu
            100                 105                 110

Glu Val Gln Arg Leu Arg Gln Gln Ile Leu Asp Thr Lys Ser Cys Leu
        115                 120                 125

Lys Asn Lys Thr Lys Glu Asn Val Asp Val Pro Leu Val Ile Cys Gly
    130                 135                 140

Asn Lys Gly Asp Arg Asp Phe Tyr Arg Glu Val Asp Gln Arg Glu Ile
145                 150                 155                 160

Glu Gln Leu Val Gly Asp Asp Pro Gln Arg Cys Ala Tyr Phe Glu Ile
                165                 170                 175

Ser Ala Lys Lys Asn Ser Ser Leu Asp Gln Met Phe Arg Ala Leu Phe
            180                 185                 190

Ala Met Ala Lys Leu Pro Ser Glu Met Ser Pro Asp Leu His Arg Lys
        195                 200                 205

Val Ser Val Gln Tyr Cys Asp Val Leu His Lys Lys Ala Leu Arg Asn
    210                 215                 220

Lys Lys Leu Leu Arg Ala Gly Ser Gly Gly Gly Gly Asp Pro Gly
225                 230                 235                 240

Asp Ala Phe Gly Ile Val Ala Pro Phe Ala Arg Arg Pro Ser Val His
                245                 250                 255

Ser Asp Leu Met Tyr Ile Arg Glu Lys Ala Ser Ala Gly Ser Gln Ala
            260                 265                 270

Lys Asp Lys Glu Arg Cys Val Ile Ser
        275                 280

<210> SEQ ID NO 47
<211> LENGTH: 189
<212> TYPE: PRT
<213> ORGANISM: Homo sapiens
```

<400> SEQUENCE: 47

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 48
<211> LENGTH: 206
<212> TYPE: PRT
<213> ORGANISM: Homo sapiens

<400> SEQUENCE: 48

Met Ala Ala Asn Lys Pro Lys Gly Gln Asn Ser Leu Ala Leu His Lys
1               5                   10                  15

Val Ile Met Val Gly Ser Gly Gly Val Gly Lys Ser Ala Leu Thr Leu
                20                  25                  30

Gln Phe Met Tyr Asp Glu Phe Val Glu Asp Tyr Glu Pro Thr Lys Ala
            35                  40                  45

Asp Ser Tyr Arg Lys Lys Val Val Leu Asp Gly Glu Glu Val Gln Ile
        50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Cys Val Phe Ser Ile Thr
                85                  90                  95

Glu Met Glu Ser Phe Ala Ala Thr Ala Asp Phe Arg Glu Gln Ile Leu
            100                 105                 110

Arg Val Lys Glu Asp Glu Asn Val Pro Phe Leu Leu Val Gly Asn Lys
        115                 120                 125

Ser Asp Leu Glu Asp Lys Arg Gln Val Ser Val Glu Glu Ala Lys Asn
    130                 135                 140

Arg Ala Glu Gln Trp Asn Val Asn Tyr Val Glu Thr Ser Ala Lys Thr
145                 150                 155                 160

Arg Ala Asn Val Asp Lys Val Phe Phe Asp Leu Met Arg Glu Ile Arg
                165                 170                 175

Ala Arg Lys Met Glu Asp Ser Lys Glu Lys Asn Gly Lys Lys Lys Arg
            180                 185                 190

Lys Ser Leu Ala Lys Arg Ile Arg Glu Arg Cys Cys Ile Leu
        195                 200                 205

<210> SEQ ID NO 49
<211> LENGTH: 205
<212> TYPE: PRT
<213> ORGANISM: Homo sapiens

<400> SEQUENCE: 49

Met Ser Ser Met Asn Pro Glu Tyr Asp Tyr Leu Phe Lys Leu Leu Leu
1               5                   10                  15

Ile Gly Asp Ser Gly Val Gly Lys Ser Cys Leu Leu Leu Arg Phe Ala
            20                  25                  30

Asp Asp Thr Tyr Thr Glu Ser Tyr Ile Ser Thr Ile Gly Val Asp Phe
        35                  40                  45

Lys Ile Arg Thr Ile Glu Leu Asp Gly Lys Thr Ile Lys Leu Gln Ile
    50                  55                  60

Trp Asp Thr Ala Gly Gln Glu Arg Phe Arg Thr Ile Thr Ser Ser Tyr
65                  70                  75                  80

Tyr Arg Gly Ala His Gly Ile Ile Val Val Tyr Asp Val Thr Asp Gln
                85                  90                  95

Glu Ser Phe Asn Asn Val Lys Gln Trp Leu Gln Glu Ile Asp Arg Tyr
            100                 105                 110

Ala Ser Glu Asn Val Asn Lys Leu Leu Val Gly Asn Lys Cys Asp Leu
        115                 120                 125

Thr Thr Lys Lys Val Val Asp Tyr Thr Thr Ala Lys Glu Phe Ala Asp
    130                 135                 140

Ser Leu Gly Ile Pro Phe Leu Glu Thr Ser Ala Lys Asn Ala Thr Asn
145                 150                 155                 160

Val Glu Gln Ser Phe Met Thr Met Ala Ala Glu Ile Lys Lys Arg Met
                165                 170                 175

Gly Pro Gly Ala Thr Ala Gly Gly Ala Glu Lys Ser Asn Val Lys Ile
            180                 185                 190

Gln Ser Thr Pro Val Lys Gln Ala Gly Gly Gly Cys Cys
        195                 200                 205

<210> SEQ ID NO 50
<211> LENGTH: 210
<212> TYPE: PRT
<213> ORGANISM: Homo sapiens

<400> SEQUENCE: 50

Met Thr Ala Ala Gln Ala Ala Gly Glu Glu Ala Pro Pro Gly Val Arg
1               5                   10                  15

Ser Val Lys Val Val Leu Val Gly Asp Gly Gly Cys Gly Lys Thr Ser
            20                  25                  30

Leu Leu Met Val Phe Ala Asp Gly Ala Phe Pro Glu Ser Tyr Thr Pro
        35                  40                  45

Thr Val Phe Glu Arg Tyr Met Val Asn Leu Gln Val Lys Gly Lys Pro
    50                  55                  60

Val His Leu His Ile Trp Asp Thr Ala Gly Gln Asp Asp Tyr Asp Arg
65                  70                  75                  80

Leu Arg Pro Leu Phe Tyr Pro Asp Ala Ser Val Leu Leu Leu Cys Phe
                85                  90                  95

-continued

```
Asp Val Thr Ser Pro Asn Ser Phe Asp Asn Ile Phe Asn Arg Trp Tyr
            100                 105                 110

Pro Glu Val Asn His Phe Cys Lys Lys Val Pro Ile Ile Val Val Gly
            115                 120                 125

Cys Lys Thr Asp Leu Arg Lys Asp Lys Ser Leu Val Asn Lys Leu Arg
            130                 135                 140

Arg Asn Gly Leu Glu Pro Val Thr Tyr His Arg Gly Gln Glu Met Ala
145                 150                 155                 160

Arg Ser Val Gly Ala Val Ala Tyr Leu Glu Cys Ser Ala Arg Leu His
                165                 170                 175

Asp Asn Val His Ala Val Phe Gln Glu Ala Ala Glu Val Ala Leu Ser
            180                 185                 190

Ser Arg Gly Arg Asn Phe Trp Arg Arg Ile Thr Gln Gly Phe Cys Val
            195                 200                 205

Val Thr
    210
```

<210> SEQ ID NO 51
<211> LENGTH: 191
<212> TYPE: PRT
<213> ORGANISM: Homo sapiens

<400> SEQUENCE: 51

```
Met Gln Thr Ile Lys Cys Val Val Gly Asp Gly Ala Val Gly Lys
1               5                   10                  15

Thr Cys Leu Leu Ile Ser Tyr Thr Thr Asn Lys Phe Pro Ser Glu Tyr
                20                  25                  30

Val Pro Thr Val Phe Asp Asn Tyr Ala Val Thr Val Met Ile Gly Gly
            35                  40                  45

Glu Pro Tyr Thr Leu Gly Leu Phe Asp Thr Ala Gly Gln Glu Asp Tyr
        50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
            115                 120                 125

Leu Ala Lys Asn Lys Gln Lys Pro Ile Thr Pro Glu Thr Ala Glu Lys
        130                 135                 140

Leu Ala Arg Asp Leu Lys Ala Val Lys Tyr Val Glu Cys Ser Ala Leu
145                 150                 155                 160

Thr Gln Arg Gly Leu Lys Asn Val Phe Asp Glu Ala Ile Leu Ala Ala
                165                 170                 175

Leu Glu Pro Pro Glu Thr Gln Pro Lys Arg Lys Cys Cys Ile Phe
            180                 185                 190
```

<210> SEQ ID NO 52
<211> LENGTH: 192
<212> TYPE: PRT
<213> ORGANISM: Homo sapiens

<400> SEQUENCE: 52

```
Met Gln Ala Ile Lys Cys Val Val Gly Asp Gly Ala Val Gly Lys
1               5                   10                  15
```

```
Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ser
            35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Asp Val Phe Leu Ile
 65                  70                  75                  80

Cys Phe Ser Leu Val Ser Pro Ala Ser Tyr Glu Asn Val Arg Ala Lys
                85                  90                  95

Trp Phe Pro Glu Val Arg His His Cys Pro Ser Thr Pro Ile Ile Leu
            100                 105                 110

Val Gly Thr Lys Leu Asp Leu Arg Asp Asp Lys Asp Thr Ile Glu Lys
            115                 120                 125

Leu Lys Glu Lys Lys Leu Ala Pro Ile Thr Tyr Pro Gln Gly Leu Ala
        130                 135                 140

Leu Ala Lys Glu Ile Asp Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Gln Pro Thr Arg Gln Gln Lys Arg Ala Cys Ser Leu Leu
            180                 185                 190

<210> SEQ ID NO 53
<211> LENGTH: 181
<212> TYPE: PRT
<213> ORGANISM: Homo sapiens

<400> SEQUENCE: 53

Met Gly Gly Phe Phe Ser Ser Ile Phe Ser Ser Leu Phe Gly Thr Arg
 1               5                  10                  15

Glu Met Arg Ile Leu Ile Leu Gly Leu Asp Gly Ala Gly Lys Thr Thr
            20                  25                  30

Ile Leu Tyr Arg Leu Gln Val Gly Glu Val Val Thr Thr Ile Pro Thr
            35                  40                  45

Ile Gly Phe Asn Val Glu Thr Val Thr Tyr Lys Asn Leu Lys Phe Gln
        50                  55                  60

Val Trp Asp Leu Gly Gly Gln Thr Ser Ile Arg Pro Tyr Trp Arg Cys
 65                  70                  75                  80

Tyr Tyr Ser Asn Thr Asp Ala Val Ile Tyr Val Val Asp Ser Cys Asp
                85                  90                  95

Arg Asp Arg Ile Gly Ile Ser Lys Ser Glu Leu Val Ala Met Leu Glu
            100                 105                 110

Glu Glu Glu Leu Arg Lys Ala Ile Leu Val Val Phe Ala Asn Lys Gln
            115                 120                 125

Asp Met Glu Gln Ala Met Thr Ser Ser Glu Met Ala Asn Ser Leu Gly
        130                 135                 140

Leu Pro Ala Leu Lys Asp Arg Lys Trp Gln Ile Phe Lys Thr Ser Ala
145                 150                 155                 160

Thr Lys Gly Thr Gly Leu Asp Glu Ala Met Glu Trp Leu Val Glu Thr
                165                 170                 175

Leu Lys Ser Arg Gln
            180
```

```
<210> SEQ ID NO 54
<211> LENGTH: 229
<212> TYPE: PRT
<213> ORGANISM: Homo sapiens

<400> SEQUENCE: 54

Met Asp Pro Asn Gln Asn Val Lys Cys Lys Ile Val Val Gly Asp
1               5                   10                  15

Ser Gln Cys Gly Lys Thr Ala Leu Leu His Val Phe Ala Lys Asp Cys
            20                  25                  30

Phe Pro Glu Asn Tyr Val Pro Thr Val Phe Glu Asn Tyr Thr Ala Ser
                35                  40                  45

Phe Glu Ile Asp Thr Gln Arg Ile Glu Leu Ser Leu Trp Asp Thr Ser
        50                  55                  60

Gly Ser Pro Tyr Tyr Asp Asn Val Arg Pro Leu Ser Tyr Pro Asp Ser
65                  70                  75                  80

Asp Ala Val Leu Ile Cys Phe Asp Ile Ser Arg Pro Glu Thr Leu Asp
                85                  90                  95

Ser Val Leu Lys Lys Trp Lys Gly Glu Ile Gln Glu Phe Cys Pro Asn
            100                 105                 110

Thr Lys Met Leu Leu Val Gly Cys Lys Ser Asp Leu Arg Thr Asp Val
                115                 120                 125

Ser Thr Leu Val Glu Leu Ser Asn His Arg Gln Thr Pro Val Ser Tyr
        130                 135                 140

Asp Gln Gly Ala Asn Met Ala Lys Gln Ile Gly Ala Ala Thr Tyr Ile
145                 150                 155                 160

Glu Cys Ser Ala Leu Gln Ser Glu Asn Ser Val Arg Asp Ile Phe His
                165                 170                 175

Val Ala Thr Leu Ala Cys Val Asn Lys Thr Asn Lys Asn Val Lys Arg
            180                 185                 190

Asn Lys Ser Gln Arg Ala Thr Lys Arg Ile Ser His Met Pro Ser Arg
        195                 200                 205

Pro Glu Leu Ser Ala Val Ala Thr Asp Leu Arg Lys Asp Lys Ala Lys
    210                 215                 220

Ser Cys Thr Val Met
225

<210> SEQ ID NO 55
<211> LENGTH: 16
<212> TYPE: PRT
<213> ORGANISM: Homo sapiens

<400> SEQUENCE: 55

Lys Ile Val Val Gly Asp Ser Gln Cys Gly Lys Thr Ala Leu Leu
1               5                   10                  15

<210> SEQ ID NO 56
<211> LENGTH: 16
<212> TYPE: PRT
<213> ORGANISM: Homo sapiens

<400> SEQUENCE: 56

Lys Ile Val Val Val Gly Asp Ala Glu Cys Gly Lys Thr Ala Leu Leu
1               5                   10                  15

<210> SEQ ID NO 57
<211> LENGTH: 16
<212> TYPE: PRT
<213> ORGANISM: Homo sapiens
```

```
<400> SEQUENCE: 57

Lys Leu Val Leu Val Gly Asp Val Gln Cys Gly Lys Thr Ala Met Leu
1               5                  10                  15

<210> SEQ ID NO 58
<211> LENGTH: 16
<212> TYPE: PRT
<213> ORGANISM: Homo sapiens

<400> SEQUENCE: 58

Lys Leu Val Ile Val Gly Asp Gly Ala Cys Gly Lys Thr Cys Leu Leu
1               5                  10                  15

<210> SEQ ID NO 59
<211> LENGTH: 16
<212> TYPE: PRT
<213> ORGANISM: Homo sapiens

<400> SEQUENCE: 59

Lys Leu Val Val Val Gly Asp Gly Ala Cys Gly Lys Thr Cys Leu Leu
1               5                  10                  15

<210> SEQ ID NO 60
<211> LENGTH: 16
<212> TYPE: PRT
<213> ORGANISM: Homo sapiens

<400> SEQUENCE: 60

Lys Cys Val Val Val Gly Asp Gly Ala Val Gly Lys Thr Cys Leu Leu
1               5                  10                  15

<210> SEQ ID NO 61
<211> LENGTH: 16
<212> TYPE: PRT
<213> ORGANISM: Homo sapiens

<400> SEQUENCE: 61

Lys Cys Val Val Val Gly Asp Gly Ala Val Gly Lys Thr Cys Leu Leu
1               5                  10                  15

<210> SEQ ID NO 62
<211> LENGTH: 16
<212> TYPE: PRT
<213> ORGANISM: Homo sapiens

<400> SEQUENCE: 62

Lys Leu Val Val Val Gly Ala Gly Gly Val Gly Lys Ser Ala Leu Thr
1               5                  10                  15

<210> SEQ ID NO 63
<211> LENGTH: 16
<212> TYPE: PRT
<213> ORGANISM: Homo sapiens

<400> SEQUENCE: 63

Arg Met Val Ile Leu Gly Ser Ser Lys Val Gly Lys Thr Ala Ile Val
1               5                  10                  15

<210> SEQ ID NO 64
<211> LENGTH: 13
<212> TYPE: PRT
<213> ORGANISM: Homo sapiens

<400> SEQUENCE: 64
```

Leu Ser Leu Trp Asp Thr Ser Gly Ser Pro Tyr Tyr Asp
1               5                   10

<210> SEQ ID NO 65
<211> LENGTH: 13
<212> TYPE: PRT
<213> ORGANISM: Homo sapiens

<400> SEQUENCE: 65

Leu Asn Met Trp Asp Thr Ser Gly Ser Ser Tyr Tyr Asp
1               5                   10

<210> SEQ ID NO 66
<211> LENGTH: 13
<212> TYPE: PRT
<213> ORGANISM: Homo sapiens

<400> SEQUENCE: 66

Leu Ser Leu Trp Asp Thr Ser Gly Ser Pro Tyr Tyr Asp
1               5                   10

<210> SEQ ID NO 67
<211> LENGTH: 13
<212> TYPE: PRT
<213> ORGANISM: Homo sapiens

<400> SEQUENCE: 67

Leu Ala Leu Trp Asp Thr Ala Gly Gln Glu Asp Tyr Asp
1               5                   10

<210> SEQ ID NO 68
<211> LENGTH: 13
<212> TYPE: PRT
<213> ORGANISM: Homo sapiens

<400> SEQUENCE: 68

Leu Ala Leu Trp Asp Thr Ala Gly Gln Glu Asp Tyr Asp
1               5                   10

<210> SEQ ID NO 69
<211> LENGTH: 13
<212> TYPE: PRT
<213> ORGANISM: Homo sapiens

<400> SEQUENCE: 69

Leu Gly Leu Phe Asp Thr Ala Gly Gln Glu Asp Tyr Asp
1               5                   10

<210> SEQ ID NO 70
<211> LENGTH: 13
<212> TYPE: PRT
<213> ORGANISM: Homo sapiens

<400> SEQUENCE: 70

Leu Gly Leu Trp Asp Thr Ala Gly Gln Glu Asp Tyr Asp
1               5                   10

<210> SEQ ID NO 71
<211> LENGTH: 13
<212> TYPE: PRT
<213> ORGANISM: Homo sapiens

<400> SEQUENCE: 71

Leu Asp Ile Leu Asp Thr Ala Gly Gln Glu Glu Tyr Asp

-continued

```
1               5                   10
```

<210> SEQ ID NO 72
<211> LENGTH: 13
<212> TYPE: PRT
<213> ORGANISM: Homo sapiens

<400> SEQUENCE: 72

Leu Asp Ile Leu Asp Thr Ser Gly Asn His Pro Phe Pro
1               5                   10

<210> SEQ ID NO 73
<211> LENGTH: 4990
<212> TYPE: DNA
<213> ORGANISM: Homo sapiens

<400> SEQUENCE: 73

| | | | | |
|---|---|---|---|---|
| ggatccacgg | ggcggatggt | tctgtgagtt | gcgagttgtt | cctgtttgtc | ttccagcccc | 60 |
| cagtcctccc | cggccactct | gattagccag | cctagggtag | ggcctggcat | aaagtcacac | 120 |
| aggcaaaccc | cagaagaagg | aaaaagggca | cctgcatgaa | caaagagctg | ggtggcagag | 180 |
| gctgcaccgg | ggtaagactt | ccttcatgca | gttgggagtc | cgcccatgtg | gggacatcag | 240 |
| gagatgccac | cccacagaat | tggtggctag | gctgtcctgg | gtgtggccga | gagaggcctg | 300 |
| atcccagtgc | ttctttcatt | ctggtccttt | ctgaaatggc | ttggattttt | aaaaaaccat | 360 |
| gagcatttat | tactttttgta | ataaaaggaa | agagatgccc | ttttaaaaga | aaagacgagg | 420 |
| gcggaaacaa | ggaagttggc | ttgctgcttg | aggagtaaag | tcccagaggc | cacctccttg | 480 |
| acaggaggcg | ctctggggca | ttcagaatgg | gaatggcagg | tgggcctggg | tcttcacaac | 540 |
| ccagcatccg | tagggcagac | ggccatgcac | agatggtacc | aggaatcact | gtggctgagg | 600 |
| acacaggcta | gatcagtgcc | tgccagtgtc | atgttcctga | tttaagggggc | cagcctggac | 660 |
| actgaccagg | ggagagctgg | gctgtgatcc | ttgaccctcg | ggccctccac | tcatatcaaa | 720 |
| tggaccctct | tgggactaga | gccccaggag | gcaatggctg | tgtggggtcc | accttcacta | 780 |
| tagccctggc | catcagtcat | cccaagttag | agcccggctg | cccatgcagt | gccgctgtgg | 840 |
| gaggcacagg | aaggcggtgc | tcagtctgaa | ggtggttcag | gtccgtacct | taactgagcc | 900 |
| cccccatgta | ccctcaactg | gctcctttat | gcagtgaaca | ccctgcacca | ctgcagccct | 960 |
| atatccaggg | ctgcgactca | gttccttctc | cccttctccc | agactctggc | agacatacct | 1020 |
| cagatggggg | caggaaccaa | gaatggcggg | gctccagccc | cagctagcct | gtcggataac | 1080 |
| tgctgcataa | gtgacaccag | gaatcagagc | caggccaggg | ccactgatga | gcccttggat | 1140 |
| gctcactgtg | tgatgcgtgc | atttgaaata | tctgacagta | agagtgaggc | ctgggagaga | 1200 |
| tgcagggact | ctgaggatgg | gggccaagct | gggctgagaa | acaagttagt | ggtgtcctgc | 1260 |
| agcagcccct | acagcaagtg | ccagcgtggg | agggaggtgg | gtaggcatgg | ggtgggtggt | 1320 |
| atggcactca | cagcactgcc | tgcagaccac | caccacctga | cagctgggcc | ggtggtgcca | 1380 |
| gctaatggct | ccctagtttt | ctcgtaagtc | agacgtggcc | aaagcaaaac | actgagcaca | 1440 |
| caggttgcct | tgaggagcag | tgactgcctc | aagagctcag | ggctgaggag | ctggctccag | 1500 |
| acagcctgtt | gccaatgttc | agcaacatca | ccccactcct | ggttactgat | cgacctggtg | 1560 |
| tgctcttgag | agtacccccca | ccaggcctca | tgggtcaata | ctactgttat | tgttgctatt | 1620 |
| gttattacca | ggccccgccc | tcctaaagca | tttgcatatt | ttcatcctta | atcacagaac | 1680 |
| cagaatcagt | atcttccaga | agagaaaact | gaggcccagg | agaaagcaag | aggctgtgct | 1740 |

-continued

| | | | | | |
|---|---|---|---|---|---|
| gtgctcccag | ggccttcctg | ggctcgctgt | ggctttgagc | tccaggtctc | tcagctagac | 1800 |
| aatgagaacg | tcggcccacg | cgcggcacag | taaaagccca | aaatgctatg | atggacgggg | 1860 |
| tgggccgctg | gctgcagagc | cctccatacc | acagagcatc | tctggctggg | agaaaggagc | 1920 |
| aggctgaggc | ctgcagcaga | gcgcggggtt | ggggaccgct | cctgttgggc | cccagcaagg | 1980 |
| cgccctgaga | cccctgctcc | atccctgccg | ctccccaccc | gctgctcct | agcctctgtt | 2040 |
| ctagctctgc | ccgcggcggc | cacagcctcc | ccgagccgcc | ggccgggccc | tctgctgccc | 2100 |
| tctggcggcc | cgagcgcgcg | gtgccgagct | ccgcgcctga | ggccctgaaa | ccccgcgtcc | 2160 |
| gcccggcggt | cgcctcccgg | gaacaagagc | ccggctgggg | accggagcgg | aagggggctg | 2220 |
| gggctggggc | tgtgctctga | ggactgcaat | atacggtccg | cgcaagcact | cagcaaacgc | 2280 |
| tgctgcgctt | actgggttac | ttactagatt | cctattctct | ggggaaactg | agaaccaaag | 2340 |
| aaaataagag | tacgcgcgcg | ggaggtgcag | gaatgggggt | ccttgcccga | agtcgcagag | 2400 |
| ggacaggggc | accgccggga | ccagaaccc | gacgcccctg | cggccgccga | gcccgcggca | 2460 |
| gtggaaaagc | ggagtccgag | cgcctccagc | ctcagcccga | ccctggactg | ctcccccag | 2520 |
| cccccgcgcc | cagagagcag | gagcccggca | gcgggtgacg | aggtcgccgg | gactgggagc | 2580 |
| cggtgcgggg | gaggcgggcc | ccgcggggcg | tgacgcaccg | agctgggagg | gccggggcgg | 2640 |
| ggcagccgag | caggctgcat | ataagggcgg | cggccgggcg | ccaaagccag | agcaagcggc | 2700 |
| ctgtgcccag | atcctgggag | aaccccagcc | gagcccagcc | tagcccgagc | ccagcccgag | 2760 |
| cggagccgga | gccccaagcc | cgagccgcgc | ccagcccgag | cagagccctc | cagccgctca | 2820 |
| ccccgcgtgc | cacccagcg | accctcagcc | gctctctgcc | cttctctcgg | ccccgcgccc | 2880 |
| gccctcgcgg | ccctctgcc | caatgaaact | ggccgcgatg | atcaagaaga | tgtgcccgag | 2940 |
| cgactcggag | ctgagtatcc | cggccaagaa | ctgctatcgc | atggtcatcc | tcggctcgtc | 3000 |
| caaggtgggc | aagacggcca | tcgtgtcgcg | cttcctcacc | ggccgcttcg | aggacgccta | 3060 |
| cacgcctacc | atcgaggact | tccaccgcaa | gttctactcc | atccgcggcg | aggtctacca | 3120 |
| gctcgacatc | ctcgacacgt | ccggcaacca | cccgttcccc | gccatgcggc | gcctctccat | 3180 |
| cctcacaggt | gagccggggg | ccgggcaggt | gcgggaggga | agggcgggga | accctcggcc | 3240 |
| agggcgcccc | gcgagcgccg | gtccggctgc | cgcgcgccga | gtagtgcgct | tcgcgcttag | 3300 |
| agaggctagc | gcgccccgcg | cggcctcaaa | gtcagcccga | cttgtcccct | gggcggccac | 3360 |
| cctcaccttc | tccttttctg | ctctctgtgc | ccctctagg | agacgttttc | atcctggtgt | 3420 |
| tcagtctgga | caaccgcgac | tccttcgagg | aggtgcagcg | gctcaggcag | cagatcctcg | 3480 |
| acaccaagtc | ttgcctcaag | aacaaaacca | aggagaacgt | ggacgtgccc | ctggtcatct | 3540 |
| gcggcaacaa | gggtgaccgc | gacttctacc | gcgaggtgga | ccagcgcgag | atcgagcagc | 3600 |
| tggtgggcga | cgaccccag | cgctgcgcct | acttcgagat | ctcggccaag | aagaacagca | 3660 |
| gcctggacca | gatgttccgc | gcgctcttcg | ccatggccaa | gctgcccagc | gagatgagcc | 3720 |
| cagacctgca | ccgcaaggtc | tcggtgcagt | actgcgacgt | gctgcacaag | aaggcgctgc | 3780 |
| ggaacaagaa | gctgctgcgg | gccggcagcg | gcggcggcg | cggcgacccg | ggcgacgcct | 3840 |
| ttggcatcgt | ggcaccctc | gcgcgccggc | ccagcgtaca | cagcgacctc | atgtacatcc | 3900 |
| gcgagaaggc | cagcgccggc | agccaggcca | aggacaagga | gcgctgcgtc | atcagctagg | 3960 |
| agccccgccg | cgctggcgac | acaacctaag | gaggaccttt | ttgttaagtc | aaatccaacg | 4020 |
| gcccggtgcg | cccagggccg | ggagcgcgcg | cggactggcg | tctcccctcc | cggcgatccg | 4080 |
| cccccagcac | tggggaggcg | ccactgaacc | gagaagggac | ggtcatctgc | tccggaagga | 4140 |

-continued

```
aagagaacgg gccaagactg ggactattcc ccaccccggg tccccattg aggcccgcca    4200 cccccataac tttgggagcg agggcccagc cgagggtgga tttatcttct caaagaccta    4260
agagtgagcg cggggtgggg gagggatgtg aagttatcca gcctctgcta ggcttcaaga    4320
aaccgtcatg cccgcttgag ggtcaggacc cacggggcat tatcttgtct gtgattccgg    4380
gttgctgtga cagccggtag agcctctgcc ctcccgaaac taagcggggg ggcgtgggtc    4440
aaatcatagc caagtgactt gtttacatgt gagtgaaact gcacaaagga acacaaaaca    4500
aaacttgcac tttaacggta gttccggtgt caacatggac acgaacaaaa ccttacccag    4560
gtgtttatac tgtgtgtgtg tgaggtcttt aaagttattg ctttatttgg ttttttaata    4620
tacaataaaa taatttaaaa tggaaaaccg gtttttttt ttttttttt tttttttgc       4680 ttttagagat ggctggagtg gggaagggtg gggagaagga aagggctggg ctttgactta    4740
ggtggaacta gaacttacct tccccagaac tggaaaataa ccctggcctt ctgaaggcag    4800
cttcagctgc cagaaaagcc ccagatgcct ggggcatcta tgtagggat ggttccctag     4860 aaaaccggga agaatataaa ggatttcagg gtctcccctg gagatgaact ctttctagcc    4920
atccacccgc ttaattttct ttgggttaga tgacaaaagg cctcattttc tgagagaatg    4980
ttctgaattc                                                         4990
```

<210> SEQ ID NO 74
<211> LENGTH: 39
<212> TYPE: PRT
<213> ORGANISM: Homo sapiens

<400> SEQUENCE: 74

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser
        35
```

<210> SEQ ID NO 75
<211> LENGTH: 50
<212> TYPE: PRT
<213> ORGANISM: Homo sapiens

<400> SEQUENCE: 75

```
Met Ala Ala Asn Lys Pro Lys Gly Gln Asn Ser Leu Ala Leu His Lys
1               5                   10                  15

Val Ile Met Val Gly Ser Gly Gly Val Gly Lys Ser Ala Leu Thr Leu
            20                  25                  30

Gln Phe Met Tyr Asp Glu Phe Val Glu Asp Tyr Glu Pro Thr Lys Ala
        35                  40                  45

Asp Ser
    50
```

<210> SEQ ID NO 76
<211> LENGTH: 46
<212> TYPE: PRT
<213> ORGANISM: Homo sapiens

<400> SEQUENCE: 76

```
Met Ser Ser Met Asn Pro Glu Tyr Asp Tyr Leu Phe Lys Leu Leu Leu
1               5                   10                  15
```

-continued

Ile Gly Asp Ser Gly Val Gly Lys Cys Leu Leu Arg Phe Ala Asp
            20                  25                  30

Asp Thr Tyr Thr Glu Ser Tyr Ile Ser Thr Ile Gly Val Asp
        35                  40                  45

<210> SEQ ID NO 77
<211> LENGTH: 53
<212> TYPE: PRT
<213> ORGANISM: Homo sapiens

<400> SEQUENCE: 77

Met Thr Ala Ala Gln Ala Ala Gly Glu Glu Ala Pro Pro Gly Val Arg
1               5                   10                  15

Ser Val Lys Val Val Leu Val Gly Asp Gly Gly Cys Gly Lys Thr Ser
            20                  25                  30

Leu Leu Met Val Phe Ala Asp Gly Ala Phe Pro Glu Ser Tyr Thr Pro
        35                  40                  45

Thr Val Phe Glu Arg
    50

<210> SEQ ID NO 78
<211> LENGTH: 39
<212> TYPE: PRT
<213> ORGANISM: Homo sapiens

<400> SEQUENCE: 78

Met Gln Thr Ile Lys Cys Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn
        35

<210> SEQ ID NO 79
<211> LENGTH: 39
<212> TYPE: PRT
<213> ORGANISM: Homo sapiens

<400> SEQUENCE: 79

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn
        35

<210> SEQ ID NO 80
<211> LENGTH: 52
<212> TYPE: PRT
<213> ORGANISM: Homo sapiens

<400> SEQUENCE: 80

Met Gly Gly Phe Phe Ser Ser Ile Phe Ser Ser Leu Phe Gly Thr Arg
1               5                   10                  15

Glu Met Arg Ile Leu Ile Leu Gly Leu Asp Gly Ala Gly Lys Thr Thr
            20                  25                  30

Ile Leu Tyr Arg Leu Gln Val Gly Glu Val Val Thr Thr Ile Pro Thr
        35                  40                  45

Ile Gly Phe Asn
    50

<210> SEQ ID NO 81
<211> LENGTH: 44
<212> TYPE: PRT
<213> ORGANISM: Homo sapiens

<400> SEQUENCE: 81

Met Asp Pro Asn Gln Asn Val Lys Cys Lys Ile Val Val Gly Asp
1               5                   10                  15

Ser Gln Cys Gly Lys Thr Ala Leu Leu His Val Phe Ala Lys Asp Cys
            20                  25                  30

Phe Pro Glu Asn Tyr Val Pro Thr Val Phe Glu Asn
            35                  40

<210> SEQ ID NO 82
<211> LENGTH: 60
<212> TYPE: PRT
<213> ORGANISM: Homo sapiens

<400> SEQUENCE: 82

Met Lys Leu Ala Ala Met Ile Lys Lys Met Cys Pro Ser Asp Ser Glu
1               5                   10                  15

Leu Ser Ile Pro Ala Lys Asn Cys Tyr Arg Met Val Ile Leu Gly Ser
            20                  25                  30

Ser Lys Val Gly Lys Thr Ala Ile Val Ser Arg Phe Leu Thr Gly Arg
        35                  40                  45

Phe Glu Asp Ala Tyr Thr Pro Thr Ile Glu Asp Phe
    50                  55                  60

<210> SEQ ID NO 83
<211> LENGTH: 59
<212> TYPE: PRT
<213> ORGANISM: Homo sapiens

<400> SEQUENCE: 83

Tyr Arg Lys Gln Val Val Ile Asp Gly Glu Thr Cys Leu Leu Asp Ile
1               5                   10                  15

Leu Asp Thr Ala Gly Gln Glu Glu Tyr Ser Ala Met Arg Asp Gln Tyr
            20                  25                  30

Met Arg Thr Gly Glu Gly Phe Leu Cys Val Phe Ala Ile Asn Asn Thr
        35                  40                  45

Lys Ser Phe Glu Asp Ile His Gln Tyr Arg Glu
    50                  55

<210> SEQ ID NO 84
<211> LENGTH: 59
<212> TYPE: PRT
<213> ORGANISM: Homo sapiens

<400> SEQUENCE: 84

Tyr Arg Lys Lys Val Val Leu Asp Gly Glu Glu Val Gln Ile Asp Ile
1               5                   10                  15

Leu Asp Thr Ala Gly Gln Glu Asp Tyr Ala Ala Ile Arg Asp Asn Tyr
            20                  25                  30

Phe Arg Ser Gly Glu Gly Phe Leu Cys Val Phe Ser Ile Thr Glu Met
        35                  40                  45

Glu Ser Phe Ala Ala Thr Ala Asp Phe Arg Glu
    50                  55

```
<210> SEQ ID NO 85
<211> LENGTH: 59
<212> TYPE: PRT
<213> ORGANISM: Homo sapiens

<400> SEQUENCE: 85

Phe Lys Ile Arg Thr Ile Glu Leu Asp Gly Lys Thr Ile Lys Leu Gln
1               5                   10                  15

Ile Trp Asp Thr Ala Gly Gln Glu Arg Phe Arg Thr Ile Thr Ser Ser
            20                  25                  30

Tyr Tyr Arg Gly Ala His Gly Ile Ile Val Val Tyr Asp Val Thr Asp
        35                  40                  45

Gln Glu Ser Phe Asn Asn Val Lys Gln Trp Leu
    50                  55

<210> SEQ ID NO 86
<211> LENGTH: 59
<212> TYPE: PRT
<213> ORGANISM: Homo sapiens

<400> SEQUENCE: 86

Tyr Met Val Asn Leu Gln Val Lys Gly Lys Pro Val His Leu His Ile
1               5                   10                  15

Trp Asp Thr Ala Gly Gln Asp Asp Tyr Asp Arg Leu Arg Pro Leu Phe
            20                  25                  30

Tyr Pro Asp Ala Ser Val Leu Leu Leu Cys Phe Asp Val Thr Ser Pro
        35                  40                  45

Asn Ser Phe Asp Asn Ile Phe Asn Arg Trp Tyr
    50                  55

<210> SEQ ID NO 87
<211> LENGTH: 59
<212> TYPE: PRT
<213> ORGANISM: Homo sapiens

<400> SEQUENCE: 87

Tyr Ala Val Thr Val Met Ile Gly Gly Glu Pro Tyr Thr Leu Gly Leu
1               5                   10                  15

Phe Asp Thr Ala Gly Gln Glu Asp Tyr Asp Arg Leu Arg Pro Leu Ser
            20                  25                  30

Tyr Pro Gln Thr Asp Val Phe Leu Val Cys Phe Ser Val Val Ser Pro
        35                  40                  45

Ser Ser Phe Glu Asn Val Lys Glu Lys Trp Val
    50                  55

<210> SEQ ID NO 88
<211> LENGTH: 59
<212> TYPE: PRT
<213> ORGANISM: Homo sapiens

<400> SEQUENCE: 88

Tyr Ser Ala Asn Val Met Val Asp Ser Lys Pro Val Asn Leu Gly Leu
1               5                   10                  15

Trp Asp Thr Ala Gly Gln Glu Asp Tyr Asp Arg Leu Arg Pro Leu Ser
            20                  25                  30

Tyr Pro Gln Thr Asp Val Phe Leu Ile Cys Phe Ser Leu Val Ser Pro
        35                  40                  45

Ala Ser Tyr Glu Asn Val Arg Ala Lys Trp Phe
    50                  55
```

```
<210> SEQ ID NO 89
<211> LENGTH: 56
<212> TYPE: PRT
<213> ORGANISM: Homo sapiens

<400> SEQUENCE: 89

Val Glu Thr Val Thr Tyr Lys Asn Leu Lys Phe Gln Val Trp Asp Leu
1               5                   10                  15

Gly Gly Gln Thr Ser Ile Arg Pro Tyr Trp Arg Cys Tyr Tyr Ser Asn
            20                  25                  30

Thr Asp Ala Val Ile Tyr Val Val Asp Ser Cys Asp Arg Asp Arg Ile
        35                  40                  45

Gly Ile Ser Lys Ser Glu Leu Val
    50                  55

<210> SEQ ID NO 90
<211> LENGTH: 59
<212> TYPE: PRT
<213> ORGANISM: Homo sapiens

<400> SEQUENCE: 90

Tyr Thr Ala Ser Phe Glu Ile Asp Thr Gln Arg Ile Glu Leu Ser Leu
1               5                   10                  15

Trp Asp Thr Ser Gly Ser Pro Tyr Tyr Asp Asn Val Arg Pro Leu Ser
            20                  25                  30

Tyr Pro Asp Ser Asp Ala Val Leu Ile Cys Phe Asp Ile Ser Arg Pro
        35                  40                  45

Glu Thr Leu Asp Ser Val Leu Lys Lys Trp Lys
    50                  55

<210> SEQ ID NO 91
<211> LENGTH: 59
<212> TYPE: PRT
<213> ORGANISM: Homo sapiens

<400> SEQUENCE: 91

His Arg Lys Phe Tyr Ser Ile Arg Gly Glu Val Tyr Gln Leu Asp Ile
1               5                   10                  15

Leu Asp Thr Ser Gly Asn His Pro Phe Pro Ala Met Arg Arg Leu Ser
            20                  25                  30

Ile Leu Thr Gly Asp Val Phe Ile Leu Val Phe Ser Leu Asp Asn Arg
        35                  40                  45

Asp Ser Phe Glu Glu Val Gln Arg Leu Arg Gln
    50                  55

<210> SEQ ID NO 92
<211> LENGTH: 38
<212> TYPE: PRT
<213> ORGANISM: Homo sapiens

<400> SEQUENCE: 92

Gln Ile Lys Arg Val Lys Asp Ser Asp Asp Val Pro Met Val Leu Val
1               5                   10                  15

Gly Asn Lys Cys Asp Leu Ala Ala Arg Thr Val Glu Ser Arg Gln Ala
            20                  25                  30

Gln Asp Leu Ala Arg Ser
        35

<210> SEQ ID NO 93
```

```
<211> LENGTH: 39
<212> TYPE: PRT
<213> ORGANISM: Homo sapiens

<400> SEQUENCE: 93

Gln Ile Leu Arg Val Lys Glu Asp Glu Asn Val Pro Phe Leu Leu Val
1               5                   10                  15

Gly Asn Lys Ser Asp Leu Glu Asp Lys Arg Gln Val Ser Val Glu Glu
            20                  25                  30

Ala Lys Asn Arg Ala Glu Gln
        35

<210> SEQ ID NO 94
<211> LENGTH: 39
<212> TYPE: PRT
<213> ORGANISM: Homo sapiens

<400> SEQUENCE: 94

Gln Glu Ile Asp Arg Tyr Ala Ser Glu Asn Val Asn Lys Leu Leu Val
1               5                   10                  15

Gly Asn Lys Cys Asp Leu Thr Thr Lys Lys Val Val Asp Tyr Thr Thr
            20                  25                  30

Ala Lys Glu Phe Ala Asp Ser
        35

<210> SEQ ID NO 95
<211> LENGTH: 51
<212> TYPE: PRT
<213> ORGANISM: Homo sapiens

<400> SEQUENCE: 95

Pro Glu Val Asn His Phe Cys Lys Lys Val Pro Ile Ile Val Val Gly
1               5                   10                  15

Cys Lys Thr Asp Leu Arg Lys Asp Lys Ser Leu Val Asn Lys Leu Arg
            20                  25                  30

Arg Asn Gly Leu Glu Pro Val Thr Tyr His Arg Gly Gln Glu Met Ala
        35                  40                  45

Arg Ser Val
    50

<210> SEQ ID NO 96
<211> LENGTH: 51
<212> TYPE: PRT
<213> ORGANISM: Homo sapiens

<400> SEQUENCE: 96

Pro Glu Ile Thr His His Cys Pro Lys Thr Pro Phe Leu Leu Val Gly
1               5                   10                  15

Thr Gln Ile Asp Leu Arg Asp Asp Pro Ser Thr Ile Glu Lys Leu Ala
            20                  25                  30

Lys Asn Lys Gln Lys Pro Ile Thr Pro Glu Thr Ala Glu Lys Leu Ala
        35                  40                  45

Arg Asp Leu
    50

<210> SEQ ID NO 97
<211> LENGTH: 51
<212> TYPE: PRT
<213> ORGANISM: Homo sapiens
```

-continued

```
<400> SEQUENCE: 97

Pro Glu Val Arg His His Cys Pro Ser Thr Pro Ile Ile Leu Val Gly
1               5                   10                  15

Thr Lys Leu Asp Leu Arg Asp Asp Lys Asp Thr Ile Glu Lys Leu Lys
            20                  25                  30

Glu Lys Lys Leu Ala Pro Ile Thr Tyr Pro Gln Gly Leu Ala Leu Ala
        35                  40                  45

Lys Glu Ile
    50

<210> SEQ ID NO 98
<211> LENGTH: 44
<212> TYPE: PRT
<213> ORGANISM: Homo sapiens

<400> SEQUENCE: 98

Ala Met Leu Glu Glu Glu Leu Arg Lys Ala Ile Leu Val Val Phe
1               5                   10                  15

Ala Asn Lys Gln Asp Met Glu Gln Ala Met Thr Ser Ser Glu Met Ala
            20                  25                  30

Asn Ser Leu Gly Leu Pro Ala Leu Lys Asp Arg Lys
        35                  40

<210> SEQ ID NO 99
<211> LENGTH: 51
<212> TYPE: PRT
<213> ORGANISM: Homo sapiens

<400> SEQUENCE: 99

Gly Glu Ile Gln Glu Phe Cys Pro Asn Thr Lys Met Leu Leu Val Gly
1               5                   10                  15

Cys Lys Ser Asp Leu Arg Thr Asp Val Ser Thr Leu Val Glu Leu Ser
            20                  25                  30

Asn His Arg Gln Thr Pro Val Ser Tyr Asp Gln Gly Ala Asn Met Ala
        35                  40                  45

Lys Gln Ile
    50

<210> SEQ ID NO 100
<211> LENGTH: 47
<212> TYPE: PRT
<213> ORGANISM: Homo sapiens

<400> SEQUENCE: 100

Gln Ile Leu Asp Thr Lys Ser Cys Leu Lys Asn Lys Thr Lys Glu Asn
1               5                   10                  15

Val Asp Val Pro Leu Val Ile Cys Gly Asn Lys Gly Asp Arg Asp Phe
            20                  25                  30

Tyr Arg Glu Val Asp Gln Arg Glu Ile Glu Gln Leu Val Gly Asp
        35                  40                  45

<210> SEQ ID NO 101
<211> LENGTH: 28
<212> TYPE: PRT
<213> ORGANISM: Homo sapiens

<400> SEQUENCE: 101

Tyr Gly Ile Pro Tyr Ile Glu Thr Ser Ala Lys Thr Arg Gln Gly Val
1               5                   10                  15
```

Glu Asp Ala Phe Tyr Thr Leu Val Arg Glu Ile Arg
            20                  25

<210> SEQ ID NO 102
<211> LENGTH: 28
<212> TYPE: PRT
<213> ORGANISM: Homo sapiens

<400> SEQUENCE: 102

Trp Asn Val Asn Tyr Val Glu Thr Ser Ala Lys Thr Arg Ala Asn Val
1               5                   10                  15

Asp Lys Val Phe Phe Asp Leu Met Arg Glu Ile Arg
            20                  25

<210> SEQ ID NO 103
<211> LENGTH: 28
<212> TYPE: PRT
<213> ORGANISM: Homo sapiens

<400> SEQUENCE: 103

Leu Gly Ile Pro Phe Leu Glu Thr Ser Ala Lys Asn Ala Thr Asn Val
1               5                   10                  15

Glu Gln Ser Phe Met Thr Met Ala Ala Glu Ile Lys
            20                  25

<210> SEQ ID NO 104
<211> LENGTH: 28
<212> TYPE: PRT
<213> ORGANISM: Homo sapiens

<400> SEQUENCE: 104

Gly Ala Val Ala Tyr Leu Glu Cys Ser Ala Arg Leu His Asp Asn Val
1               5                   10                  15

His Ala Val Phe Gln Glu Ala Ala Glu Val Ala Leu
            20                  25

<210> SEQ ID NO 105
<211> LENGTH: 28
<212> TYPE: PRT
<213> ORGANISM: Homo sapiens

<400> SEQUENCE: 105

Lys Ala Val Lys Tyr Val Glu Cys Ser Ala Leu Thr Gln Arg Gly Leu
1               5                   10                  15

Lys Asn Val Phe Asp Glu Ala Ile Leu Ala Ala Leu
            20                  25

<210> SEQ ID NO 106
<211> LENGTH: 28
<212> TYPE: PRT
<213> ORGANISM: Homo sapiens

<400> SEQUENCE: 106

Asp Ser Val Lys Tyr Leu Glu Cys Ser Ala Leu Thr Gln Arg Gly Leu
1               5                   10                  15

Lys Thr Val Phe Asp Glu Ala Ile Arg Ala Val Leu
            20                  25

<210> SEQ ID NO 107
<211> LENGTH: 29
<212> TYPE: PRT
<213> ORGANISM: Homo sapiens

<400> SEQUENCE: 107

Trp Gln Ile Phe Lys Thr Ser Ala Thr Lys Gly Thr Gly Leu Asp Glu
1               5                   10                  15

Ala Met Glu Trp Leu Val Glu Thr Leu Lys Ser Arg Gln
            20                  25

<210> SEQ ID NO 108
<211> LENGTH: 40
<212> TYPE: PRT
<213> ORGANISM: Homo sapiens

<400> SEQUENCE: 108

Gly Ala Ala Thr Tyr Ile Glu Cys Ser Ala Leu Gln Ser Glu Asn Ser
1               5                   10                  15

Val Arg Asp Ile Phe His Val Ala Thr Leu Ala Cys Val Asn Lys Thr
            20                  25                  30

Asn Lys Asn Val Lys Arg Asn Lys
        35                  40

<210> SEQ ID NO 109
<211> LENGTH: 60
<212> TYPE: PRT
<213> ORGANISM: Homo sapiens

<400> SEQUENCE: 109

Asp Pro Gln Arg Cys Ala Tyr Phe Glu Ile Ser Ala Lys Lys Asn Ser
1               5                   10                  15

Ser Leu Asp Gln Met Phe Arg Ala Leu Phe Ala Met Ala Lys Leu Pro
            20                  25                  30

Ser Glu Met Ser Pro Asp Leu His Arg Lys Val Ser Val Gln Tyr Cys
        35                  40                  45

Asp Val Leu His Lys Lys Ala Leu Arg Asn Lys Lys
    50                  55                  60

<210> SEQ ID NO 110
<211> LENGTH: 25
<212> TYPE: PRT
<213> ORGANISM: Homo sapiens

<400> SEQUENCE: 110

Gln His Lys Leu Arg Lys Leu Asn Pro Pro Asp Glu Ser Gly Pro Gly
1               5                   10                  15

Cys Met Ser Cys Lys Cys Val Leu Ser
            20                  25

<210> SEQ ID NO 111
<211> LENGTH: 30
<212> TYPE: PRT
<213> ORGANISM: Homo sapiens

<400> SEQUENCE: 111

Ala Arg Lys Met Glu Asp Ser Lys Glu Lys Asn Gly Lys Lys Lys Arg
1               5                   10                  15

Lys Ser Leu Ala Lys Arg Ile Arg Glu Arg Cys Cys Ile Leu
            20                  25                  30

<210> SEQ ID NO 112
<211> LENGTH: 32
<212> TYPE: PRT
<213> ORGANISM: Homo sapiens

```
<400> SEQUENCE: 112

Lys Arg Met Gly Pro Ala Thr Ala Gly Ala Glu Lys Ser Asn
1               5                   10                  15

Val Lys Ile Gln Ser Thr Pro Val Lys Gln Ala Gly Gly Cys Cys
            20                  25                  30

<210> SEQ ID NO 113
<211> LENGTH: 19
<212> TYPE: PRT
<213> ORGANISM: Homo sapiens

<400> SEQUENCE: 113

Ser Ser Arg Gly Arg Asn Phe Trp Arg Arg Ile Thr Gln Gly Phe Cys
1               5                   10                  15

Val Val Thr

<210> SEQ ID NO 114
<211> LENGTH: 14
<212> TYPE: PRT
<213> ORGANISM: Homo sapiens

<400> SEQUENCE: 114

Glu Pro Pro Glu Thr Gln Pro Lys Arg Lys Cys Cys Ile Phe
1               5                   10

<210> SEQ ID NO 115
<211> LENGTH: 15
<212> TYPE: PRT
<213> ORGANISM: Homo sapiens

<400> SEQUENCE: 115

Cys Pro Gln Pro Thr Arg Gln Gln Lys Arg Ala Cys Ser Leu Leu
1               5                   10                  15

<210> SEQ ID NO 116
<211> LENGTH: 35
<212> TYPE: PRT
<213> ORGANISM: Homo sapiens

<400> SEQUENCE: 116

Ser Gln Arg Ala Thr Lys Arg Ile Ser His Met Pro Ser Arg Pro Glu
1               5                   10                  15

Leu Ser Ala Val Ala Thr Asp Leu Arg Lys Asp Lys Ala Lys Ser Cys
            20                  25                  30

Thr Val Met
        35

<210> SEQ ID NO 117
<211> LENGTH: 55
<212> TYPE: PRT
<213> ORGANISM: Homo sapiens

<400> SEQUENCE: 117

Leu Leu Arg Ala Gly Ser Gly Gly Gly Gly Asp Pro Gly Asp Ala
1               5                   10                  15

Phe Gly Ile Val Ala Pro Phe Ala Arg Arg Pro Ser Val His Ser Asp
            20                  25                  30

Leu Met Tyr Ile Arg Glu Lys Ala Ser Ala Gly Ser Gln Ala Lys Asp
        35                  40                  45

Lys Glu Arg Cys Val Ile Ser
    50                  55
```

```
<210> SEQ ID NO 118
<211> LENGTH: 34
<212> TYPE: DNA
<213> ORGANISM: Artificial Sequence
<220> FEATURE:
<223> OTHER INFORMATION: Probe/Primer

<400> SEQUENCE: 118
ctcatggagc tcaaactgtt actattaggt gccg                                    34
```